(12) United States Patent
Mao

(10) Patent No.: US 8,979,534 B2
(45) Date of Patent: Mar. 17, 2015

(54) TOOTH SCAFFOLDS

(75) Inventor: Jeremy J. Mao, Closter, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 13/378,789

(22) PCT Filed: Jun. 17, 2010

(86) PCT No.: PCT/US2010/039035
§ 371 (c)(1),
(2), (4) Date: Jul. 26, 2012

(87) PCT Pub. No.: WO2010/148229
PCT Pub. Date: Dec. 23, 2010

(65) Prior Publication Data
US 2012/0282573 A1 Nov. 8, 2012

Related U.S. Application Data

(60) Provisional application No. 61/187,875, filed on Jun. 17, 2009, provisional application No. 61/354,164, filed on Jun. 11, 2010.

(51) Int. Cl.
*A61C 13/08* (2006.01)
*A61L 27/48* (2006.01)
(Continued)

(52) U.S. Cl.
CPC ............... *A61L 27/48* (2013.01); *A61L 27/46* (2013.01); *A61L 27/54* (2013.01); *A61L 27/56* (2013.01);
(Continued)

(58) Field of Classification Search
USPC ........ 433/167, 201.1, 202.1, 204, 212.1, 215, 433/218, 223, 226, 175; 623/17.17, 901, 623/902; 424/422–426, 435
See application file for complete search history.

(56) References Cited

U.S. PATENT DOCUMENTS 6,899,915 B2 * 5/2005 Yelick et al. ................. 427/2.26
7,074,412 B2 7/2006 Weber
(Continued)

FOREIGN PATENT DOCUMENTS

CN        1658914 A     8/2005
CN      101264341 A     9/2008
(Continued)

OTHER PUBLICATIONS

Kim, H. Biomedical nanocomposites of hydroxyapatite-polycaprolactone obtained by surfactant mediation. Journal of Biomedical Materials Research Part A, (2007) vol. 83A, Issue 1, [> serial < online], [retrieved on Sep. 10, 2013]. Retrieved from the Internet: http://onlinelibrary.wiley.com/doi/10.1002/jbm.a.31247/full.*
(Continued)

*Primary Examiner* — Cris L Rodriguez
*Assistant Examiner* — Justin O'Donnell
(74) *Attorney, Agent, or Firm* — Dentons US LLP

(57) ABSTRACT

Provided is an acellular mammalian tooth-shaped scaffold including a compound that is chemotactic, osteogenic, dentinogenic, amelogenic, or cementogenic. Also provided is a method of replacing a tooth in the mouth of a mammal, where the tooth is absent and a tooth socket is present in the mouth at the position of the absent tooth. The method includes implanting an acellular scaffold having the shape of the missing tooth into the tooth socket. Additionally, a method of making a tooth scaffold is provided. The method includes synthesizing an acellular scaffold in the shape of a mammalian tooth and adding at least one compound that is chemotactic, osteogenic, dentinogenic, amelogenic, or cementogenic.

15 Claims, 20 Drawing Sheets

(51) Int. Cl.
A61L 27/46 (2006.01)
A61L 27/54 (2006.01)
A61L 27/56 (2006.01)
C12N 5/077 (2010.01)
A61C 8/00 (2006.01)
A61K 35/12 (2006.01)

(52) U.S. Cl.
CPC ............. *C12N 5/0654* (2013.01); *A61C 8/0036* (2013.01); *A61K 35/12* (2013.01); *A61L 2300/252* (2013.01); *A61L 2300/414* (2013.01); *A61L 2300/426* (2013.01); *A61L 2300/45* (2013.01); *A61L 2300/622* (2013.01); *C12N 2501/155* (2013.01); *C12N 2501/21* (2013.01); *C12N 2533/18* (2013.01); *C12N 2533/40* (2013.01); *C12N 2533/54* (2013.01); *A61L 2430/12* (2013.01)
USPC ......................... 433/202.1; 424/423; 424/435

(56) References Cited

U.S. PATENT DOCUMENTS

| | | | |
|---|---|---|---|
| 7,101,708 B1* | 9/2006 | Lapidot et al. | 435/377 |
| 7,309,232 B2* | 12/2007 | Rutherford et al. | 433/226 |
| 2004/0083006 A1* | 4/2004 | Ellingsen et al. | 623/23.57 |
| 2005/0070782 A1 | 3/2005 | Brodkin | |
| 2006/0024249 A1* | 2/2006 | Yelick et al. | 424/50 |
| 2006/0069435 A1* | 3/2006 | Brown et al. | 623/11.11 |
| 2007/0172101 A1 | 7/2007 | Kriveshko et al. | |
| 2007/0202145 A1* | 8/2007 | Ghabrial et al. | 424/423 |

FOREIGN PATENT DOCUMENTS

| | | | | |
|---|---|---|---|---|
| WO | WO 2008013900 A2 * | 1/2008 | | A61K 38/06 |
| WO | WO2009/006558 | 1/2009 | | |

OTHER PUBLICATIONS

Laflamme, C.; Mahmoud, R. Effect of BMP-2 and BMP-7 homodimers and a mixture of BMP-2/BMP-7 homodimers on osteoblast adhesion and growth following culture on a collagen scaffold. Journal of Biomedical Materials, (2008) vol. 3, [> serial < online], [retrieved on Sep. 10, 2013]. Retrieved from the Internet: http://iopscience.iop.org/1748-605X/.*
Schantz, J; Chim, H; Whiteman, M. Cell Homing in Tissue Engineering: SDF-1 Mediates Site-Directed Homing of Mesenchymal Stem Cells within Three-Dimensional Polycaprolactone Scaffolds. Tissue Engineering, (2007) vol. 13, Issue 11, [> serial < online], [retrieved on Sep. 10, 2013]. Retrieved from the Internet: http://online.liebertpub.com/doi/a.*
Albrektsson et al., Osteoinduction, osteoconduction and osseointegration, Eur Spine J, 2001, pp. S96-S101, vol. 10, Suppl. 2.
Alhadlaq et al., Adult stem cell driven genesis of human shaped articular condyle, Ann Biomed Eng., 2004, pp. 911-923, vol. 32, No. 7.
Alhadlaq et al., Mesenchymal stem cells: isolation and therapeutics, Stem Cells Dev., 2004, pp. 436-448, vol. 13.
Alhadlaq et al., Tissue-engineered osteochondral constructs in the shape of an articular condyle, J Bone Joint Surg Am., 2005, pp. 936-944, vol. 87, No. 5.
Alpaslan et al., Long-term evaluation of recombinant human bone morphogenetic protein-2 induced bone formation with a biologic and synthetic delivery system, Br J of Oral Maxillofac Surg., 1996, pp. 414-418, vol. 34.
Amar et al., Implications of cellular and molecular biology advances in periodontal regeneration, Anat Rec., 1996, pp. 361-373, vol. 245.
Amar et al., The impact of periodontal infection on systemic diseases, Med Sci Monit, 2003, pp. RA291-RA299, vol. 9, No. 12.

Aoki et al., Synergistic effects of different bone morphogenetic protein type I receptors on alkaline phosphatase induction, J. Cell. Sci., 2001, pp. 1483-1489, vol. 114.
Aono et al., Potent Ectopic Bone-Inducing Activity of Bone Morphogenetic Protein-4/7 Heterodimer, Biochemical and Biophysical Res. Commun., 1995, pp. 670-677, vol. 210, No. 3.
Arceo et al., Human periodontal cells initiate mineral like nodules in vitro, J Periodontol, 1991, pp. 499-503, vol. 62.
Artico et al., Bone autografting of the calvaria and craniofacial skeleton: historical background, surgical results in a series of 15 patients, and review of the literature, Surg. Neurol., 2003, pp. 71-79, vol. 60.
Arzate et al., Human cementum protein extract promotes chondrogenesis and mineralization in mesenchymal cells, J Periodontal Res., 1996, pp. 144-148, vol. 31.
Arzate et al., Production of a monoclonal antibody to an attachment protein derived from human cementum, FASEB J.,1992, pp. 2990-2995, vol. 6.
Ashman et al., Ridge augmentation for immediate postextraction implants: eight year retrospective study, Pract. Periodontics Aesthet Dent., 1995, pp. 85-94, vol. 7.
Ashman et al., Placement of Implants Into Ridges Grafted with Bioplant HTR Synthetic Bone: Histological Long-Term Case History Reports, J. Oral Implantology, 2000, pp. 276-290, vol. 26 No. 4.
Astrand et al., Changes in the alveolar process after extractions in the white rat. A histologic and fluorescence microscopic study, Acta Odontol. Scand., 1969, pp. 113-127, vol. 27, No. 1.
Atala et al., Tissue-engineered autologous bladders for patients needing cystoplasty, Lancet., 2006, pp. 1241-1246, vol. 367.
Balic et al., Analysis of developmental potentials of dental pulp in vitro using GFP transgenes, Orthod Craniofac Res., 2005, pp. 252-258, vol. 8.
Bartold et al., Molecular and cell biology of healthy and diseased periodontal tissues., Periodontol 2000, 2006, pp. 29-49, vol. 40.
Bartold et al., Periodontal Regeneration. In: Biology of the periodontal connective tissues, Chapter 11, 1998, Chicago: Quintessence Publishing, pp. 241-260.
Bartold et al., Tissue engineering: a new paradigm for periodontal regeneration based on molecular and cell biology., Periodontol 2000, 2000,pp. 253-269, vol. 24.
Bax et al., Bone Morphogenetic Protein-2 Increases the Rate of Callus Formation after Fracture of the Rabbit Tibia., Calcified Tissue Int., 1999, pp. 83-89, vol. 65.
Becker et al., Periodontal regeneration: a contemporary evaluation., Periodontol 2000, 1999, pp. 104-114, vol. 19.
Berkovitz et al., Microscopic anatomy of oro-dental tissues. In: Berkovitz BKB, Holland GR, Moxham BJ, eds. Color Atlas and Textbook of Oral Anatomy, Histology and Embryology, 1992, pp. 109-228, London: Mosby-Wolfe.
Berry et al., Exploring the origins of cementoblasts and their trigger factors, Connect Tissue Res., 2003, pp. 97-102, vol. 44, Suppl. 1.
Bleul et al., A highly efficacious lymphocyte chemoattractant, stromal cell-derived factor 1 (SDF-1), J. Exp. Med., 1996, pp. 1101-1109, vol. 184.
Bohl et al., Role of synthetic extracellular matrix in development of engineered dental pulp., Biomater Sci Polymer Ed., 1998, pp. 749-764, vol. 9.
Bosshardt et al., Developmental appearance and distribution of bone sialoprotein and osteopontin in human and rat cementum, Anat Rec., 1998, pp. 13-33, vol. 250.
Bosshardt, Are cementoblasts a subpopulation of osteoblasts or a unique phenotype?, J Dent Res, 2005, pp. 390-406, vol. 84, No. 5.
Boyne, Application of bone morphogenetic proteins in the treatment of clinical oral and maxillofacial osseous defects, J. Bone Joint Surg. Am., 2001, pp. S146-S150, vol. 83, No. A.
Braut et al., Analysis of the odontogenic and osteogenic potentials of dental pulp in vivo using a collal-2.3-GFP transgene, Int J Dev Biol., 2003, pp. 281-292, vol. 47.
Brown et al., Osteogenic protein-1: a review of its utility in spinal applications Biodrugs, 2006, pp. 243-251, vol. 20.
Burns et al., Tumorigenic heterogeneity in cancer stem cells evolved from long-term cultures of telomeraseimmortalized human mesenchymal stem cells, Cancer Res., 2005, pp. 3126-3135, vol. 65.

(56) References Cited

OTHER PUBLICATIONS

Carlisle et al., Bone morphogenetic proteins for spinal fusion, Spine J., 2005, pp. 240S-249S, vol. 55.
Carlson, Platelet-rich plasma: clinical applications in dentistry, J Am Dent Assoc., 2002, pp. 1383-1386, vol. 133.
Castro-Malaspina et al., Characterization of human bone marrow fibroblast colonyforming cells (CFU-F) and their progeny, Blood, 1980, pp. 289-301, vol. 56.
Castro-Malaspina et al., Human megakaryocyte stimulation of proliferation of bone marrow fibroblasts, Blood, 1981, pp. 781-787, vol. 57.
Causa et al., Poly-E-caprolactone / hydroxyapatite composites for bone regeneration: In vitro characterization and human osteoblast response, Journal of Biomedical Materials Research Part A, 2005, pp. 151-162, vol. 76, No. A(1).
Chai et al., Fate of the mammalian cranial neural crest during tooth and mandibular morphogenesis, Development, 2000, pp. 1671-1679, vol. 127.
Chai, Prospects for tooth regeneration in the 21st century: a perspective, Microsc Res Tech, 2003, pp. 469-479, vol. 60.
Chen et al., Bone morphogenetic protein 2 (BMP-2) enhances BMP-3, BMP-4, and bone cell differentiation marker gene expression during the induction of mineralized bone matrix formation in cultures of fetal rat calvarial osteoblasts, Calcif. Tissue Int., 1997, pp. 283-290, vol. 60.
Chen et al., Bone Morphogenetic Proteins, Growth Factors, 2004, pp. 233-241, vol. 22, No. 4.
Cheng et al., Osteogenic Activity of the Fourteen Types of Human Bone Morphogenetic Proteins (BMPs), J. Bone. Joint. Surg. Am., 2003, pp. 1544-1552, vol. 85, No. A.
Chim et al., A comparative analysis of scaffold material modifications for load-bearing applications in bone tissue engineering, Int. J. Oral Maxillofac. Surg., 2006, pp. 928-934, vol. 35.
Chim et al., Efficacy of glow discharge gas plasma treatment as a surface modification process for three-dimensional poly (D/L-lactide) scaffolds, J. Biomed. Mater. Res. A., 2003, pp. 327-335, vol. 65A.
Chim et al., Human Circulating Peripheral Blood Mononuclear Cells for Calvarial Bone Tissue Engineering, Plast. Reconstr. Surg., 2006, pp. 468-478, vol. 116.
Chinese Office Action in related Chinese Patent Application Serial No. 201080037027 dated Apr. 3, 2014, in Chinese, 10 pages.
Chinese Office Action in related Chinese Patent Application Serial No. 201080037027 dated Apr. 3, 2014, in English, 16 pages.
CN1658914 published Aug. 24, 2005, English abstract, downloaded from Espacenet, 1 page.
CN101264341 published Sep. 17, 2008, English abstract, downloaded from Espacenet, 1 page.
Cho et al., In Vitro Formation of Mineralized Nodules by Periodontal Ligament Cells from the Rat, Calcif Tissue Int., 1992, pp. 459-467, vol. 50.
Choi et al., Studies of Brush Border Enzymes, Basement Membrane Components, and Electrophysiology of Tissue-Engineered Neointestine, J. of Ped. Surg., 1998, pp. 991-997, vol. 33, No. 7.
Chopp et al., Spinal cord injury in rat: treatment with bone marrow stromal cell transplantation, Neuroreport, 2000, pp. 3001-3005, vol. 11.
Claveau et al., Basement membrane protein and matrix metalloproteinase deregulation in engineered human oral mucosa following infection with Candida albicans, Matrix Biol., 2004, pp. 477-486, vol. 23.
Crane et al., Bone tissue engineering, Nat. Med., 1995, pp. 1322-1324, vol. 1, No. 12.
D'Errico et al., Immortalized Cementoblasts and Periodontal Ligament Cells in Culture, Bone, 1999, pp. 39-47, vol. 25, No. 1.
De Wynter et al., Properties of peripheral blood and cord blood stem cells, Baillieres Clinical Haematology,1999, pp. 1-17, vol. 12, No. 1/2.
Deans et al., Mesenchymal stem cells: Biology and potential clinical uses, Exp Hematology, 2000, pp. 875-884, vol. 28.
Denizot et al., Rapid colorimetric assay for cell growth and survival, Modifications to the tetrazolium dye procedure giving improved sensitivity and reliability, J. Immunol. Methods, 1986, pp. 271-277, vol. 89.
Desbois et al., Osteocalcin Cluster: Implications for Functional Studies, J. Cell. Biochemistry, 1995, pp. 379-383, vol. 57.
Deville et al., Freeze casting of hydroxyapatite scaffolds for bone tissue engineering, Biomaterials,2006, pp. 5480-5489, vol. 27. (originally listed as Sylvain-can move in alpha order).
Dua et al., Limbal Stem Cells of the Corneal Epithelium, Survey of Ophthalmology, 2000, pp. 415-425, vol. 44, No. 5.
Duailibi et al., Bioengineered Teeth from Cultured Rat Tooth Bud Cells, J Dent Res., 2004, pp. 523-528, vol. 83.
Duailibi et al., Prospects for tooth regeneration, Periodontology 2000, 2006, pp. 177-187, vol. 41.
Elsubeihi et al., Quantitative assessment of post-extraction healing and alveolar ridge remodelling of the mandible in female rats, Archives of Oral Biology, 2004, pp. 401-412, vol. 49.
Eppley et al., Allograft and Alloplastic Bone Substitutes: A Review of Science and Technology for the Craniomaxillofacial Surgeon, J. Craniofac. Surg., 2005, pp. 981-989, vol. 16.
Fenton et al., Overdenture oversights, Dent Clin North Am, 1979, pp. 117-130, vol. 23.
Fibbe et al., The Role of Metalloproteinases and Adhesion Molecules in Interlukin-8-Induced Stem Cell Mobilization, Seminar in Hematology,2000, pp. 19-24, vol. 37, No. 1, Suppl. 2.
Fiedler et al., VEGF-A and P1GF-1 stimulate chemotactic migration of human mesenchymal progenitor cells, Biochem. Biophys. Res. Commun., 2005, pp. 561-568, vol. 334.
Fong et al., The Crowning Achievement: Getting to the Root of the Problem, J Dental Education, 2005, pp. 555-570, vol. 69, No. 5.
Friedenstein et al., Origin of Bone Marrow Stromal Mechanocytes in Radiochimeras and Heterotopic Transplants, 1978, Exp Hemat., pp. 440-444, vol. 6.
Friedenstein et al., Precursor cells of mechanocytes, Int Rev Cytol, 1976, pp. 327-359, vol. 47.
Fuchs et al., Fetal Tracheal Augmentation with Cartilage Engineered from Bone Marrow-Derived Mesenchymal Progenitor Cells, J Pediatric Surg., 2003, pp. 984-987, vol. 38., No. 6.
Fujiwara et al., Insulin-like growth factor I stimulates cell proliferation in the outer layer of Hertwig's epithelial root sheath and elongation of the tooth root in mouse molars in vitro, Cell Tissue Res., 2005, pp. 69-75, vol. 320.
Gazdag et al., Alternatives to Autogenous Bone Graft: Efficacy and Indications, J American Academy of Orthopaedic Surgeons, 1995, pp. 1-8, vol. 3.
Gazzerro et al., Skeletal Bone Morphogenetic Proteins Suppress the Expression of Collagenase-3 by Rat Osteoblasts, Endocrinology, 1999, pp. 562-567, vol. 140.
Geiger et al., Collagen sponges for bone regeneration with rhBMP-2, Adv. Drug Deliv. Rev., 2003,pp. 1613-1629, vol. 55.
Giannobile et al., Platelet-Derived Growth Factor (PDGF) Gene Delivery for Application in Periodontal Tissue Engineering, 2001, J Periodontol, pp. 815-823, vol. 72.
Giannobile, Periodontal Tissue Engineering by Growth Factors, Bone, 1996, pp. 23S-37S, vol. 19., No. 1, Supplement.
Giannoudis et al., Bone substitutes: An Update, Injury, 2005, pp. S20-S27, vol. 36, Suppl. 3.
Giannoudis et al., Clinical applications of BMP-7: The UK perspective, 2005, Injury, pp. S47-S50, vol. 36S, Suppl. 3.
Gojo et al., In vivo cardiovasculogenesis by direct injection of isolated adult mesenchymal stem cells, Exp Cell Res, 2003, pp. 51-59, vol. 288.
Griffith et al., Tissue engineering—current challenges and expanding opportunities, Science, 2002, 5 Pages, vol. 295.
Groeneveld et al., Bone morphogenetic proteins in human bone regeneration, Eur. J. Endocrinol, 2000, pp. 9-21, vol. 142.
Gronthos et al., Differential cell surface expression of the STRO-1 and alkaline phosphatase antigens on discrete developmental stages in primary cultures of human bone cells, J Bone Miner Res, 1999, pp. 47-56, vol. 14.

(56) References Cited

OTHER PUBLICATIONS

Gronthos et al., Molecular and cellular characterization of highly purified stromal stem cells derived from human bone marrow, J Cell Sci, 2003, pp. 1827-1835, vol. 116.
Gronthos et al., Postnatal human dental pulp stem cells (DPSCs) in vitro and in vivo, Proc. Natl. Acad. Sci. USA, 2000, pp. 13625-13630, vol. 97.
Gronthos et al., Telomerase accelerates osteogenesis of bone marrow stromal stem cells by upregulation of CBFA1, osterix, and osteocalcin, J Bone Miner Res, 2003, pp. 716-722, vol. 18, No. 4.
Gronthos et al., The STRO-1+ fraction of adult human bone marrow contains the osteogenic precursors, Blood, 1994, pp. 4164-4173, vol. 84.
Guglielmotti et al., Alveolar wound healing and ridge remodeling after tooth extraction in the rat: a histologic, radiographic, and histometric study, J. Oral Maxillofac. Surg., 1985, pp. 359-364, vol. 43, No. 5.
Harada et al., Epithelial stem cells in teeth, 2002, Odontology, pp. 1-6, vol. 90.
Harada et al., New perspectives on tooth development and the dental stem cell niche, Arch Histol Cytol, 2004, pp. 1-11, vol. 67, No. 1.
Hawkins et al., Asymmetric cell division: from A to Z, Genes Dev, 1998, pp. 3625-3638, vol. 12.
Heijl et al., Enamel matrix derivative (EMDOGAIN) in the treatment of intrabony periodontal pockets, J Clin Periodontol, 1997, pp. 705-714, vol. 24.
Herodin et al., Short-term injection of antiapoptotic cytokine combinations soon after lethal gamma-irradiation promotes survival, Blood, 2003, pp. 2609-2616, vol. 101.
Hirooka, The biologic concept for the use of enamel matrix protein: true periodontal regeneration, Quintessence Int, 1998, pp. 621-630, vol. 29.
Brigid Hogan, Bone morphogenetic proteins: multifunctional regulators of vertebrate development, Genes & Dev., 1996, pp. 1580-1594, vol. 10.
Honda et al., Histological and immunohistochemical studies of tissue engineered odontogenesis, Arch Histol Cytol, 2005, pp. 89-101, vol. 68.
Horwitz et al., Clinical responses to bone marrow transplantation in children with severe osteogenesis imperfect, Blood, 2001, pp. 1227-1231, vol. 97.
Horwitz et al., Isolated allogenic bone marrow-derived messenchymal cells engraft and stimulate growth in children with osteogenesis imperfect: implications for cell therapy of bone, Proc. Natl. Acad. Sci., 2002, pp. 8932-8937, vol. 99.
Howell et al., A phase I/II clinical trial to evaluate a combination of recombinant human plateletderived growth factor-BB and recombinant insulin-like growth factor in patients with periodontal disease, J Periodontol, 1997, pp. 1186-1193, vol. 68.
Hu et al., Bone marrow cells can give rise to ameloblast-like cells, J Dent Res, 2006, pp. 416-420, vol. 85 No. 5.
Hu et al., Dental epithelial histomorphogenesis in vitro, J Dent Res, 2005, pp. 521-525, vol. 84.
Hu et al., Tissue engineering of tooth crown, root, and periodontium, 2006, Tissue Eng, pp. 2069-2075, vol. 12.
Hutmacher et al., An introduction to biodegradable materials for tissue engineering applications, Ann Acad Med Singapore, 2001, pp. 183-191, vol. 30.
Hutmacher et al., Mechanical Properties and Cell Cultural Response of Polycaprolactone Scaffolds Designed and Fabricated via Fused Deposition Modeling, 2001, J Biomed Mat Res, pp. 203-216, vol. 55.
Huysseune et al., Early development of the zebrafish (*Danio rerio*) pharyngeal dentition (Teleostei, Cyprinidae), Anat Embryol, 1998, pp. 289-305, vol. 198.
Ikada, Tissue engineering research trends at Kyoto University. In: Ikada Y, ed. Tissue Engineering for Therapeutic Use 1, 1998, Tokyo, Elsevier, pp. 1-14.
International Search Report and Written Opinion dated Aug. 30, 2010 in related Application No. PCT/US2010/039035 filed Jun. 17, 2010, 9 pages.
Isobe et al., Bone Regeneration Produced in Rat Femur Defects by Polymer Capsules Containing Recombinant Human Bone Morphogenetic Protein-2, J Oral Maxillofac Surg, 1999, pp. 695-698, vol. 57.
Israel et al., Heterodimeric bone morphogenetic proteins show enhanced activity in vitro and in vivo, Growth Factors, 1996, pp. 291-300, vol. 13.
Ivanovski et al., Expression of bone matrix protein mRNAs by primary and cloned cultures of the regenerative phenotype of human periodontal fibroblasts, J Dent Res, 2001, pp. 1665-1671, vol. 80.
Jackman et al., FGF signaling is required for zebrafish tooth development, Dev Biol, 2004, pp. 139-157, vol. 274.
Jernvall et al., Reiterative signaling and patterning during mammalian tooth morphogenesis, Mech Dev, 2000, pp. 19-29, vol. 92.
Jin et al., Cementum engineering with threedimensional polymer scaffolds, J Biomed Mater Res A, 2003, pp. 54-60, vol. 67.
Jin et al., Engineering of tooth supporting structures by delivery of PDGF gene therapy vectors, Mol Ther, 2004, pp. 519-526, vol. 9.
Jin et al., Gene therapy of bone morphogenetic protein for periodontal tissue engineering, J Periodontol, 2003, pp. 202-213, vol. 74.
Jorgensen et al., Tissue engineering through autologous mesenchymal stem cells, Current Opin Biotechnol, 2004, pp. 406-410, vol. 15.
Kaigler et al., Tissue engineering impact on dentistry, J Dent Educ, 2001, pp. 456-462, vol. 65.
Kang et al., Characterization of the distinct orthotopic bone-forming activity of 14 BMPs using recombinant adenovirus-mediated gene delivery, Gene Therapy, 2004, pp. 1312-1320, vol. 11.
Karring et al., Development of the biological concept of guided tissue regeneration-animal and human studies, Periodontol 2000, 1993, pp. 26-35, vol. 1.
Katchburian et al., Histologia e Embriologia Oral, $2^{nd}$ edn., Brazil: Editorial Medica Panamericana. Guanabara Koogan, 2005, pp. 151-179.
Kato et al., Optimized use of a biodegradable polymer as a carrier material for the local delivery of recombinant human bone morphogenetic protein-2 (rhBMP-2), Biomaterials, 2006, pp. 2035-2041, vol. 27.
Kawano et al., Characterization of dental epithelial progenitor cells derived from cervical-loop epithelium in a rat lower incisor, J Dent Res, 2004, pp. 129-133, vol. 83.
Kenley et al., Biotechnology and bone graft substitutes, Pharm. Res, 1993, pp. 1393-1401, vol. 10.
Kim et al., Hydroxyapatite/poly(ε-caprolactone) composite coatings on hydroxyapatite porous bone scaffold for drug delivery, Biomaterials, 2004, pp. 1279-1287, vol. 25.
Kim et al., In vitro behavior of hematopoietic progenitor cells under the influence of chemoattractants: stromal cell-derived factor-1, steel factor, and the bone marrow environment, Blood, 1998, pp. 100, vol. 91.
Kim et al., Periodontal disease and systemic conditions: a bidirectional relationship, Odontology, 2006, pp. 10-21, vol. 94.
Kim et al., Survival and function of hepatocytes on a novel three dimensional synthetic biodegradable polymer scaffold with an intrinsic network of channels, Ann Surgery, 1998, pp. 8-13, vol. 28.
Kim et al., The current status of tissue engineering as potential therapy, Seminar Pediatric Surg, 1998, pp. 119-123, vol. 8.
Kim, Development of biocompatible synthetic extracellular matrices for tissue engineering, TIBTECH, 1998, pp. 224-230, vol. 16.
Koempel et al., The effect of recombinant human bone morphogenetic protein-2 on the integration of porous hydroxyapatite implants with bone, J Biomed Mater Res, 1998, pp. 359-363, vol. 41.
Koh et al., Fabrication of poly ε-caprolactone/hydroxyapatite scaffold using rapid direct deposition, Materials Letters, 2006, pp. 1184-1187, vol. 60, No. s 9-10.
Kollet et al., HGF, SDF-1 and MMP-9 are involved in stress-induced CD34+ stem cell recruitment to the liver, J. Clin. Invest., 2003, pp. 160-169, vol. 112, No. 2.
Kong et al., A study on the bioactivity of chitosan/nano-hydroxyapatite composite scaffolds for bone tissue engineering, Eur Polym J, 2006, pp. 3171-3179, vol. 42.

(56) References Cited

OTHER PUBLICATIONS

Kortesidis et al., Stromal-derived factor-1 promotes the growth, survival, and development of human bone marrow stromal stem cells, Blood, 2005, pp. 3793-3801, vol. 105 No. 10.

Krebsbach et al., Repair of craniotomy defects using bone marrow stromal cells, Transplantation, 1998, pp. 1272-1278, vol. 66.

Kuboki et al., Two Distinctive BMP-Carriers Induce Zonal Chondrogenesis and Membranous Ossification, Respectively; Geometrical Factors of Matrices for Cell-Differentiation, Connective Tissue Research, 1995, pp. 219-226, vol. 32 Nos. 1-4.

Kucia et al., Trafficking of normal stem cells and metastasis of cancer stem cells involve similar mechanisms: pivotal role of the SDF-i-CXCR4 axis, Stem Cells, 2005, pp. 879, vol. 23.

Landers et al. Rapid prototyping of scaffolds derived from thermoreversible hydrogels and tailored for applications in tissue engineering, Biomaterials, 2002, pp. 4437-4447, vol. 23.

Landers et al., Rapid prototyping in medicine, Internal Report, EnvisionTec, Germany 2005.

Lang et al., Attachment formation following replantation of cultured cells into periodontal defects, J Dent Res, 1998, pp. 393-405, vol. 77 No. 2.

Langer et al., Tissue Engineering, Science, 1993, pp. 920-926, vol. 260.

Lapidot et al., Current understanding of stem cell mobilization: the roles of chemokines, proteolytic enzymes, adhesion molecules, cytokines, and stromal cells, Exp. Hematology, 2002, pp. 973-981, vol. 30.

Laurell et al., Guided tissue regeneration update, Int Dental Journal, 1998, pp. 386-398, vol. 48.

Lekic et al., Periodontal ligament cell population: the central role of fibroblasts in creating a unique tissue, Anat Rec, 1996, pp. 327-341, vol. 245.

Leong, Solid freeform fabrication of three-dimensional scaffolds for engineering replacement tissues and organs, Biomaterials, 2003, pp. 2363-2378, vol. 24.

L. Kong et al., A study on the bioactivity of chitosan/nano-hydroxyapatite composite scaffolds for bone tissue engineering, European Polymer J, 2006, pp. 3171-3179, vol. 42.

Lin, The self-renewing mechanism of stem cells in the germ line, Curr Opin Cell Biol, 1998, pp. 687-693, vol. 10.

Lindskog, Formation of intermediate Cementum I: Early Mineralization of Aprismatic enamel and intermediate cementum in monkey, J Craniofacial Genetics Dev. Biology, 1982, pp. 147-160, vol. 2.

Liu et al., Targeted delivery system for juxtacrine signaling growth factor based on rhBMP-2-mediated carrier-protein conjugation, Bone, 2006, pp. 825-836, vol. 39.

Lu et al., Controlled release of transforming growth factor β1 from biodegradable polymer microparticles, J. of Biomedical Materials Res, 1999, pp. 440-451, vol. 50, No. 3, Part A.

Lu et al., The importance of new processing techniques in tissue engineering, MRS Bulletin, 1996, pp. 28-32, vol. 21, No. 11.

Lyons et al., Colocalization of BMP-7 and BMP-2 RNAs suggests that these factors cooperatively mediate tissue interactions during murine development, Mechanisms of Dev., 1995, pp. 71-83, vol. 50.

Ma et al., Biodegradable Polymer Scaffolds with Well Defined Interconnected Spherical Pore Network, Tissue Engineering, 2001, pp. 23-33, vol. 7.

Malekzadeh et al., Isolation of Human Osteoblast-Like Cells and in Vitro Amplification for Tissue Engineering, J Periodontol, 1998, pp. 1256-1262, vol. 69.

Mano et al., Bioinert, biodegradable and injectable polymeric matrix composites for hard tissue replacement: state of the art and recent developments, Composites Science Technology, 2004, pp. 789-817, vol. 64.

Manolagas et al., The Role of IL-6 Type Cytokines and Their Receptors in Bone, Ann. NY Acad. Sci., 1998, pp. 194-204, vol. 840.

Marion et al., Mesenchymal Stem Cells and Tissue Engineering, Methods Enzymol, 2006, pp. 339-361, vol. 420.

Mayer et al., Subtle differences in the mitogenic effects of recombinant human bone morphogenetic proteins -2 to -7 on DNA synthesis on primary bone-forming cells and identification of BMP-2/4 receptor, Calcif. Tissue Int., 1996, pp. 249-255, vol. 58.

McCulloch et al., Paravascular cells in endosteal spaces of alveolar bone contribute to periodontal ligament cell populations, Anat Rec, 1987, pp. 233-242, vol. 219.

McCulloch, Origins and functions of cells essential for periodontal repair: the role of fibroblasts in tissue homeostasis, Oral Dis, 1995, pp. 271-278, vol. 1.

McCulloch, Progenitor cell populations in the periodontal ligament of mice, Anat Rec, 1985, pp. 258-262, vol. 211.

Meinel et al., Silk implants for the healing of critical size bone defects, Bone, 2005, pp. 688-698, vol. 37.

Melcher, Cells of periodontium: their role in the healing of wounds, Ann R Coll Surg. Engl., 1985, pp. 130-131, vol. 67.

Mikos et al., Laminated three dimensional biodegradable foams for use in tissue engineering, Biomaterials, 1993, pp. 323-330, vol. 14.

Mikos et al., Wetting of poly (L-lactic acid) and poly (Dl-lactic-co-glycolic acid) foams for tissue culture, Biomaterials, 1994, pp. 55-58, vol. 15.

Mikos, Preparation and characterization of poly L-lactic acid foam, Polymer, 1994, pp. 1068-1077, vol. 35.

Miletich et al., Neural crest contribution to mammalian tooth formation, Birth Defects Res C Embryo Today, 2004, pp. 200-12, vol. 72.

Mina et al., New Insight into Progenitor/Stem Cells in Dental Pulp Using Col 1a1-GFP Transgenes, Cells Tissues Organs, 2004, pp. 120-133, vol. 176.

Miura et al., SHED: Stem cells from human exfoliated deciduous teeth, Proc Natl Acad Sci USA, 2003, pp. 5807-5812, vol. 100.

Modino et al., Tissue engineering of teeth using adult stem cells, Arch Oral Biol., 2005, pp. 255-258, vol. 50.

Moioli et al., Chondrogenesis of mesenchymal stem cells by controlled delivery of transforming growth factor-beta3, Conf Proc IEEE Eng Med Biol Soc., 2006, pp. 2647-50, vol. 1.

Mooney et al., Engineering dental pulp-like tissue in vitro, Biotechnol. Prog., 1996, pp. 865-868, vol. 12.

Mooney et al., Growing new organs, Sci Am, 1999, pp. 60-65, vol. 280.

Mooney, Novel approach to fabrication porous sponge of poly D,L-lactic-co glycolic acid without the use of organic solvents, Biomaterials, 1996, pp. 1417-1422, vol. 17.

Moradian-Oldak, Amelogenins: assembly, processing and control of crystal morphology, Matrix Biol., 2001, pp. 293-305, vol. 20.

Moroni et al., 3D fiber-deposited scaffolds for tissue engineering: Influence of pores geometry and architecture on dynamic mechanical properties, Biomaterials, 2006, pp. 974-985, vol. 27.

Moss, Studies on dentin. I. Mantle dentin, Acta Anat (Basel), 1999, pp. 481-507, vol. 87.

Moule et al., Donor variability in the proliferation of human dental pulp fibroblasts, Aust Dent J, 1995, pp. 110-114, vol. 40.

Murata et al., Carrier-dependency of cellular differentiation induced by bone morphogenetic protein in ectopic sites, Int. J Oral Maxillofacial Surg., 1998, pp. 391-396, vol. 27.

Murphy et al., Bone Regeneration via a Mineral Substrate and Induced Angiogenesis, Journal of Dental Research, 2004, pp. 204-210, vol. 83.

Murphy et al., Controlled delivery of inductive proteins, plasmid DNA and cells from tissue engineering matrices, J Periodontal Res, 1999, pp. 413-419, vol. 34.

Muschler et al., Engineering Principles of Clinical Cell Based Tissue Engineering, J Bone Joint Surg Am., 2004, pp. 1541-1558, vol. 86-A, No. 7.

Nakagawa et al., Ultrastructural study of direct bone formation induced by BMPs-collagen complex implanted into an ectopic site, Oral Diseases, 2000, pp. 172-179, vol. 6.

Nakahara et al., In situ tissue engineering of periodontal tissues by seeding with periodontal ligament-derived cells, Tissue Eng, 2004, pp. 537-544, vol. 10.

Nakahara et al., Novel approach to regeneration of periodontal tissues based on in situ tissue engineering: effects of controlled release of basic fibroblast growth factor from a sandwich membrane, Tissue Eng, 2003, pp. 153-162, vol. 9.

(56) References Cited

OTHER PUBLICATIONS

Nakahara, A review of new developments in tissue engineering therapy for periodontitis, Dent Clin North Am, 2006, pp. 265-276, vol. 50.
Nakao et al., The development of a bioengineered organ germ method, Nature Methods, 2007, pp. 227-230, vol. 4.
Nakashima et al., Stimulation of Reparative Dentin Formation by Ex Vivo Gene Therapy Using Dental Pulp Stem Cells Electrotransfected with Growth/Differentiation Factor 11 (Gdf11), Hum Gene Therapy, 2004, pp. 1045-1053, vol. 15.
Nakashima et al., The application of tissue engineering to regeneration of pulp and dentin in endodontics, J. Endod, 2005, pp. 711-718, vol. 31.
Nakashima, Bone morphogenetic proteins in dentin regeneration for potential use in endodontic therapy, Cytokine & Growth Factor Reviews, 2005, pp. 369-376, vol. 16, No. 3.
Nakashima, The application of bone morphogenic proteins to dental tissue engineering, Nature Biotechnology, 2003, pp. 1025-1032, vol. 21, No. 9.
Nakatomi et al., Sonic hedgehog signaling is important in tooth root development, J Dent Res, 2006, pp. 427-431, vol. 85.
Nakatsu et al., $VEGF_{121}$ and $VEGF_{165}$ Regulate Blood Vessel Diameter Through Vascular Endothelial Growth Factor Receptor 2 in an In Vitro Angiogenesis Model, Laboratory Invest., 2003, pp. 1873-1885, vol. 83, No. 12.
National Institute for Dental and Craniofacial Research, Strategic Plan-2003-2008, J Am Coll Dent, 2003, pp. 43-55, vol. 70.
Nebahat et al., Biocomposites of nanohydroxyapatite with collagen and poly vinyl alcohol, Coll Surf B, 2006, pp. 42-49, vol. 48.
Ohazama et al., Stem-cell based tissue engineering of murine teeth, J Dent Res, 2004, pp. 518-522, vol. 83, No. 7.
Ohazama et al., Stem-cell-based Tissue Engineering of Murine Teeth, J Dent Res, 2004, pp. 518-522, vol. 83 No. 7, Supplemental.
Onishi et al., Distinct and Overlapping Patterns of Localization of Bone Morphogenetic Protein (BMP) Family Members and a BMP Type II Receptor During Fracture Healing in Rats, Bone, 1998, pp. 605-612, vol. 22., No. 6.
Owen et al., Stromal stem cells: marrow-derived osteogenic precursors, Ciba Found. Symp, 1988, pp. 42-60, vol. 136.
Owen ME et al., Clonal analysis in vitro of osteogenic differentiation of marrow CFU-F., J Cell Sci,1987, pp. 731-738, vol. 87.
Payne et al., Regulation of tooth development by the novel type I TGFβ family member receptor Alk8, J Dent Res, 2001, pp. 1968-1973, vol. 80.
Peled et al., Dependence of Human Stem Cell Engraftment and Repopulation of NOD/SCID Mice on CXCR4, Science,1999, pp. 845-848, vol. 283.
Peled et al., The chemokine SDF-1 stimulates integrin-mediated arrest of CD34 cells on vascular endothelium under shear flow, J. Clin. Invest., 1999, pp. 1199, vol. 104.
Peng et al., Transcriptional characterization of bone morphogenetic proteins (BMPs)-mediated osteogenic signalling, J. Cell. Biochem., 2003, pp. 1149-1165, vol. 90.
Perez et al., Anti-cementoblastoma-derived protein antibody partially inhibits mineralization on a cementoblastic cell line, J Struct Biol, 2003, pp. 1-13, vol. 143.
Perkins et al., Stromal Cell Progeny of Murine Bone Marrow Fibroblast Colony-Forming Units are Clonal Endothelial-Like Cells That Express Collagen IV and Laminin, Blood,1990, pp. 620-625, vol. 75. No. 3.
Perrino et al., Immunolocalization of Alk8 during Replacement Tooth Development in Zebrafish, Cells Tissues Organs, 2004, pp. 17-27, vol. 176.
Persidis, Tissue engineering, Nature Biotechnol, 1999, pp. 508-510, vol. 17.
Pihlstrom et al., Periodontal Diseases, Lancet, 2005, pp. 1809-1820, vol. 366.
Pietrokovski et al., Ridge Remodeling after Tooth Extraction in Rats, J. Dent. Res.,1967, pp. 222-231, vol. 46, No. 1.

Pitaru et al., Cellular origins and differentiation control mechanisms during periodontal development and wound healing, J Periodontal Res,1994, pp. 81-94, vol. 29.
Plikus et al., Morphoregulation of teeth: modulating the number, size, shape and differentiation by tuning Bmp activity, Evolution and Development, 2005, pp. 440-457, vol. 7.
Qing et al., A novel porous cells scaffold made of polylactide-dextran blend by combining phase-separation and particle leaching techniques, 2002, Biomaterials, pp. 4483-4492, vol. 23.
Quesenberry et al., Phenotype of the Engrafting Stem Cell in Mice, Stem Cells, 1998, pp. 33-5, vol. 16, Suppl 1.
Quinones et al., Current status of guided tissue regeneration, Periodontology 2000, 1995, pp. 55-68, vol. 9.
Rahaman et al., Stem cell-based composite tissue constructs for regenerative medicine, Biotechnology and Bioengineering, 2005, pp. 261-284, vol. 91. No. 3.
Rao, Multipotent and Restricted Precursors in the Central Nervous System, Anatomical Record, 1999, pp. 137-148, vol. 257.
Rezwan et al., Biodegradable and bio active porous polymer/inorganic composite scaffolds for bone tissue engineering, Biomaterials, 2006, pp. 3413-3431, vol. 27.
Rich et al., In vitro evaluation of poly (ϵ-caprolactone-co-DL-lactide)/ bioactive glass composites, Biomaterials, 2002, pp. 2143-2150, vol. 23.
Ripamonti et al., Tissue engineering, morphogenesis, and regeneration of the periodontal tissues by bone morphogenetic proteins, Crit. Rev. Oral Biol. Med,1997, pp. 154-163, vol. 8.
Rouabhia et al., Interleukin-18 and Gamma Interferon Production by Oral Epithelial Cells in Response to Exposure to *Candida albicans* or Lipopolysaccharide Stimulation, Infection and Immunity, 2002, pp. 7073-7080, vol. 70.
Rubio et al., Spontaneous human adult stem cell transformation, 2005, Cancer Res, pp. 3035-3039, vol. 65. [2005, Erratum in Cancer Res, p. 4969, vol. 65].
Rutherford et al., Platelet derived growth factor and dexamethasone combined with a collagen matrix induce regeneration of the periodontium in monkeys, J Clin Periodontol, 1993, pp. 537-544, vol. 20.
Sainio et al., Mesonephric kidney—stem cell factory?, Int J Dev Biol, 1999, pp. 435-439, vol. 43.
Saito et al., New synthetic absorbable polymers as BMP carriers: Plastic properties of poly-D,L-lactic acid-polyethylene glycol block copolymers, J Biomed Mater Res, 1999, pp. 104-110, vol. 47.
Saito et al., New synthetic biodegradable polymers as BMP carriers for bone tissue engineering, Biomaterials, 2003, pp. 2287-2293, vol. 24.
Sampath et al., Bovine Osteogenic Protein is Composed of Dimers of OP-1 and BMP-2A, Two Members of the Transforming Growth Factor-beta Superfamily*, J. Biol. Chem., 1990, pp. 13198-13205, vol. 265. No. 22.
Santos et al., Si-Ca-P xerogels and bone morphogenetic protein act synergistically on rat stromal marrow cell differentiation in vitro, J Biomed Mater Res, 1998, pp. 87-94, vol. 41.
Schantz et al., Induction of Ectopic Bone Formation by Using Human Periosteal Cells in Combination With a Novel Scaffold Technology, 2002, Cell Transplantation, pp. 125-138, vol. 11.
Scott et al., Interactions of human prostatic epithelial cells with bone marrow endothelium: binding and invasion, Br. J. Cancer, 2001, pp. 1417, vol. 84.
Seale et al., A New Look at the Origin, Function, and Stem-Cell Status of Muscle Satellite Cells, Developmental Biology, 2000, pp. 115-124, vol. 218.
Seo et al., Investigation of multi-potent postnatal stem cells from human periodontal ligament, Lancet, 2004, pp. 149-155, vol. 364.
Sharpe et al., Test-Tube teeth, Scientific America, 2005, pp. 34-41, vol. 293.
Shi et al., Bone formation by human postnatal bone marrow stromal stem cells is enhanced by telomerase expression, Nature Biotechnology, Jun. 2002, pp. 587-591, vol. 20.
Shi et al., Comparison of Human Dental Pulp and Bone Marrow Stromal Stem Cells by cDNA Microarray Analysis, Bone, 2001, pp. 532-539, vol. 29. No. 6.

(56) References Cited

OTHER PUBLICATIONS

Shi et al., Perivascular Niche of Postnatal Mesenchymal Stem Cells in Human Bone Marrow and Dental Pulp, J Bone Miner Res, 2003, pp. 696-704, vol. 18. No. 4.
Shi et al., The efficacy of mesenchymal stem cells to regenerate and repair dental structures, Orthod Craniofacial Res., 2005, pp. 191-199, vol. 8.
Shieh et al., State-of-the-art tissue engineering: from tissue engineering to organ building, Surgery, 2005, pp. 1-7, vol. 137 No. 1.
Shimizu, Tissue engineering for soft tissues, In: Ikada Y, ed. Tissue Engineering for Therapeutic Use 2, 1998, pp. 119-122.
Shin et al., Biomimetic materials for tissue engineering, Biomaterials, 2003, pp. 4353-4364, vol. 24.
Simmons et al., Identification of Stromal Cell Precursors in Human Bone Marrow by a Novel Monoclonal Antibody, STRO-1, Blood, 1991, pp. 55-62, vol. 78 No. 1.
Simonsen et al., Telomerase expression extends the proliferative life-span and maintains the osteogenic potential of human bone marrow stromal cells, Nature Biotechnology, 2002, pp. 592-596, vol. 20.
Sittinger et al., Tissue engineering and autologous transplant formation: practical approaches with resorbable biomaterials and new cell culture techniques, Biomaterials, 1996, pp. 237-242, vol. 17.
Slavkin et al., Hertwig's epithelial root sheath differentiation and initial cementum and bone formation during long-term organ culture of mouse mandibular first molars using serumless, chemically defined medium, J Periodontal Res, 1989, pp. 28-40, vol. 24.
Smith et al., Transdentinal Stimulation of Tertiary Dentinogenesis, Adv. Dent Res, 2001, pp. 51-54, vol. 15.
Smith, Tooth Tissue Engineering and Regeneration—a Translational Vision!, J Dent Res, 2004, pp. 517, vol. 83 No. 7.
Sodek, A New Approach to Assessing Collagen Turnover by using a Micro-Assay A Highly Efficient and Rapid Turnover of Collagen in Rat Periodontal Tissues, Biochem J, 1976, pp. 243-246, vol. 160.
Sonoyama et al., Mesenchymal Stem Cell-Mediated Functional Tooth Regeneration in Swine, PLoS ONE, e79, 2006, pp. 1-8, vol. 1, No. 1.
Steele-Perkins et al., Essential role for NFI-C/CTF transcription-replication factor in tooth root development, Molecular and Cellular Biol., 2003, pp. 1075-1084, vol. 23. No. 3.
Sternlicht et al., How Matrix Metalloproteinases Regulate Cell Behavior, Annu. Rev. Cell Dev. Biol., 2001, pp. 463-516, vol. 17.
Stock et al., Tissue Engineering: Current State and Prospects, Annu. Rev Med, 2001, pp. 143-151, vol. 52.
Stosich et al., Vascularized adipose tissue grafts from human mesenchymal stem cells with bioactive cues and microchannel conduits, Tissue Eng., 2007, pp. 2881-2890, vol. 13, No. 12.
Sumikawa et al., Microstructure of primary tooth dentin, Pediatric Dent, 1999, pp. 439-444, vol. 21.
Suzuki et al., Alginate hydrogel linked with synthetic oligopeptide derived from BMP-2 allows ectopic osteoinduction in vivo, J. Biomed. Mater. Res., 2000, pp. 405-409, vol. 50.
Sweeney et al., Repair of critical size rat calvarial defects using extracellular matrix protein gels, J Neurosurg, 1995, pp. 710-715, vol. 83.
Taba et al., Current concepts in periodontal bioengineering, Orthod Craniofac Res, 2005, pp. 292-302, vol. 8.
Tabata, Significance of release technology in tissue engineering, Drug Discovery Today, 2005, pp. 1639-1646, vol. 10.
Taguchi et al., Interleukin-6-type Cytokines Stimulate Mesenchymal Progenitor Differentiation toward the Osteoblastic Lineage, Proc. Assoc. Am. Physicians, 1998, pp. 559-574, vol. 110.
Tan et al., Scaffold development using selective laser sintering of polyetheretherketone-hydroxyapatite biocomposite blends, Biomaterials, 2003, pp. 3115-3123, vol. 24.
Tardif et al., Gingival and Dermal Fibroblasts Produce Interleukin-1 β Converting Enzyme and Interleukin-1 β But Not Interleukin-18 Even After Stimulation with Lipopolysaccharide, J. Cell. Physiol., 2004, pp. 125-132, vol. 198.

Thesleff et al., Enamel Knots as Signaling Centers Linking Tooth Morphogenesis and Odontoblast Differentiation, Adv. Dent Res, 2001, pp. 14-18, vol. 15.
Thesleff et al., Epithelial-Mesenchymal Signaling During Tooth Development, Connective Tissue Research, 1995, pp. 9-15, vol. 32. No. 1-4.
Thesleff et al., Molecular Regulation of Tooth Development, Bone, 1999, pp. 123-125, vol. 25. No. 1.
Thesleff et al., Signalling networks regulating dental development, Mechanisms of Development, 1997, pp. 111-123, vol. 67.
Thesleff, Epithelial-mesenchymal signalling regulating tooth morphogenesis, J Cell Science, 2003, pp. 1647-1648, vol. 116.
Thesleff, The Genetic Basis of Tooth Development and Dental Defects, Am J Med Genetics Part A, 2006, pp. 2530-2535, vol. 140A.
Thies et al., Recombinant Human Bone Morphogenetic Protein-2 Induces Osteoblastic Differentiation in W-20-17 Stromal Cells, Endocrinology, 1992, pp. 1318-1324, vol. 130 No. 3.
Toma et al., Human Mesenchymal Stem Cells Differentiate to a Cardiomyocyte Phenotype in the Adult Murine Heart, Circulation, 2002, pp. 93-98, vol. 105.
Tsuji et al., Expression of the PEBP2α A/AML3/CBFA1 Gene is Regulated by BMP4/7 Heterodimer and Its Overexpression Suppresses Type I Collagen and Osteocalcin Gene Expression in Osteoblastic and Nonosteoblastic Mesenchymal Cells, Bone, 1998, pp. 87-92, vol. 22 No. 2.
Tucker et al., The Cutting-Edge of Mammalian Development; How the Embryo Makes Teeth, Nat Rev Genet, 2004, pp. 499-508, vol. 5.
Tummers et al., Root or crown: a developmental choice orchestrated by the differential regulation of the epithelial stem cell niche in the tooth of two rodent species, Development, 2003, pp. 1049-1057, vol. 130.
Vacanti et al., Tissue-engineered spinal cord, Transplantation Proceedings, 2001, pp. 592-598, vol. 33.
Van Der Heyden et al., Dynamics of Tooth Formation and Replacement in the Zebrafish (*Danio rerio*) (Teleostei, Cyprinidae), Development Dynamics, 2005, pp. 486-496, vol. 219.
Van Der Heyden et al., Tooth development in vitro in two teleost fish, the cichlid *Hemichromis bimaculatus* and the cyprinid *Danio rerio*, Cell Tissue Res, 2005, pp. 375-389, vol. 321.
Van Der Heyden et al., Tooth succession in the zebrafish (*Danio rerio*), Arch Oral Biol., 2001, pp. 1051-1058, vol. 46.
Van Dijk et al., Cell seeding of periodontal ligament fibroblasts. A pilot study, J Clin Periodontol, 1991, pp. 196-199, vol. 18.
Vandervelde et al., Signaling factors in stem cell-mediated repair of infarcted myocardium, J Mol. Cell Cardiology, 2005, pp. 363-376, vol. 39, No. 2.
Varghese et al., Regulation of Collagenase-3 by Bone Morphogenetic Protein-2 in Bone Cell Cultures, Endocrinology, 1997, pp. 1035-1040, vol. 138.
Vavidovitch, Bone Metabolism Associated with Tooth Eruption and Orthodontic Tooth Movement, J Periodontol, 1979, pp. 22-29, vol. 50 (4 Spec No).
Viljanen et al., Low dosage of native allogeneic bone morphogenetic protein in repair of sheep calvarial defects, Int. J Oral Maxillofacial Surg., 1997, pp. 389-393, vol. 26.
Wei et al., A study on nano-composite of hydroxyapatite and polyamide, J Materials Science, 2003, pp. 3303-3306, vol. 38.
Winn et al., Sustained release emphasizing recombinant human bone morphogenetic protein-2, Adv. Drug Deliv. Rev., 1998, pp. 303-318, vol. 31.
Woodfield et al., Polymer Scaffolds Fabricated with Pore-size Gradients as a Model for Studying the Zonal Organization within Tissue-Engineered Cartilage Constructs, Tissue Eng, 2005, pp. 1297-1311, vol. 11, No. 9/10.
Wozney et al., Growth factors influencing bone development, J Cell Sci Suppl.,1990, pp. 149-156, vol. 13.
Wynn et al., A small proportion of mesenchymal stem cells strongly expresses functionality active CXCR4 receptor capable of promoting migration to bone marrow, Blood, 2004, pp. 2643-2645, vol. 104 No. 9.
Xiao et al., Tissue Engineering for Bone Regeneration using Differentiated Alveolar Bone Cells in Collagen Scaffolds, Tissue Engineering, 2003, pp. 1167-1177, vol. 9.

(56) References Cited

OTHER PUBLICATIONS

Yamada et al., Expression profile of active genes in human periodontal ligament and isolation of PLAP-1, a novel SLRP family gene, Gene, 2001, pp. 279-286, vol. 275.

Yamashiro et al., Expression of Bone Morphogenetic Proteins and Msx Genes during Root Formation, J Dent Res, 2003, pp. 172-176, vol. 82 No. 3.

Yelick et al., Bioengineered Teeth from Tooth Bud Cells, Dent Clin North Am, 2006, pp. 191-203, vol. 50.

Yelick et al., Molecular Dissection of Craniofacial Development using Zebrafish, Crit. Rev Oral Biol. Med, 2002, pp. 308-322, vol. 13.

Yeong et al., Rapid prototyping in tissue engineering: Challenges and potential Trends, 2004, Biotechnol, pp. 643-652, vol. 22.

Young et al., Developmental analysis and three-dimensional computer modeling of tooth crowns grown on biodegradable polymer scaffolds, Arch Oral Biol, 2005, pp. 259-265, vol. 50.

Young et al., Tissue engineering of complex tooth structure on biodegradable polymer scaffolds, 2002, J Dent Res, pp. 695-700, vol. 81.

Young et al., Tissue-engineered hybrid tooth and bone, Tissue Eng, 2005, pp. 1599-1610, vol. 11.

Zhang et al., Differentiation ability of rat postnatal dental pulp cells in vitro, Tissue Eng, 2005, pp. 357-368, vol. 11.

Zhao et al., Cementoblast delivery for periodontal tissue engineering, 2004, J Periodontol, pp. 154-161, vol. 75.

Zhao et al., Human bone marrow stem cells exhibit neural phenotypes and ameliorate neurological deficits after grafting into the ischemic brain of rats, Exp. Neurol., 2002, pp. 11-20, vol. 174.

Zhao et al., Preparation of bioactive porous HA/PCL composite scaffolds, Applied Surface Science, 2008, pp. 2942-2946, vol. 255, No. 5, Part 2.

Zhu et al., Combined bone morphogenetic protein-2 and -7 gene transfer enhances osteoblastic differentiation and spine fusion in a rodent model, 2004, J. Bone Miner. Res., pp. 2021-2032, vol. 19.

\* cited by examiner

TOOTH SCAFFOLDS

CROSS-REFERENCE TO RELATED APPLICATION

The present application claims the benefit of PCT International Application No. PCT/US10/39035, filed 17 Jun. 2010; which claims the benefit of U.S. Provisional Application Ser. No. 61/187,875, filed 17 Jun. 2009, and U.S. Provisional Application Ser. No. 61/354,164, filed 11 Jun. 2010; all of which are incorporated herein by reference in their entireties.

BACKGROUND

The present invention relates to tissue engineering scaffolds.

Biomedical Engineering and Tooth Regeneration.

Tooth loss often results from a variety of oral diseases and physiological causes, including dental caries, periodontal disease, trauma, genetic disorders and aging (Amar 2003, Philstrom 2005, Kim 2006). Tooth loss can lead to physical and mental suffering that can lower an individual's self-esteem and quality of life (Amar 2003, Philstrom 2005, Kim 2006). Many forms of dental disease and some medical conditions like uncontrolled diabetes increase the risk of tooth loss. For the treatment of edentulism, the current options have been limited to the use of dental implants and/or conventional fixed or removable prostheses.

Recently, the emergence and development of biomedical engineering tools have led to a new scope of patient care in the field of medicine. For example, preliminary human clinical trials have reported of improved levels of bone formation in children with osteogenesis imperfecta, following systemic infusions of bone marrow stromal stem cells (BMSSC) or bone marrow cells (Horwitz 2001, Horwitz 2002). Recent advances in the fields of dental tissue engineering, materials science and stem cell biology suggest that tooth regeneration will be possible (Duailibi 2006). Additionally, the recent identification of different mesenchymal stem cells (MSCs) residing in dental or craniofacial tissues expands the scope of potential clinical benefits in helping to regenerate the dental tissues such as dentin, cementum and periodontal ligament (PDL) (Shi 2005). Dental tissue progenitor cells present in the pulp tissue of deciduous and adult teeth can be used to regenerate dentin and alveolar bone (Shi 2005; Zhang 2005). Additionally, cells isolated from both rat and pig tooth buds can be used to bioengineer anatomically correct tooth crowns but with limited predictability (Duailibi 2004, Honda 2005, Young 2002, Young 2005).

The tooth/periodontal complexes are often referred to as an individual organ. Although this organ is considered relatively small, its structural and developmental complexity is well recognized. The tooth structure consists of three calcified tissue types—enamel, dentin and cementum, and dental pulp. Dentin occupies the bulk of the tooth, while enamel and cementum cover the coronal and apical portions, respectively. The periodontium has a supportive role to the teeth and consists of cementum, periodontal ligaments, alveolar bone and gingiva. Periodontal ligaments are connective tissues that attach the cementum to the alveolar bone via the Sharpey's fibers. Periodontal ligaments enable sensory perception and cushion mechanical forces during mastication.

Despite the tooth's structural complexity, the advancement of biomedical engineering techniques has given rise to two currently employed approaches for tooth regeneration. The first is based on tissue engineering, aiming to regenerate teeth by seeding stem cells in scaffolding biomaterials (Young 2002, Duailibi 2004, Honda 2005). This technique has shown promising results in regeneration of the periodontium (Nakahara 2006). The second approach attempts to reproduce or mimic the developmental processes of embryonic tooth formation (Nakahara 2006). This approach uses embryonic tissues (dental epithelium and dental mesenchyme) harvested from a mouse fetus and requires an understanding of the principles that regulate early tooth development in the embryo (Ohazama 2004, Hu 2006, Nakao 2007). Following these approaches, in many studies, biologically engineered tooth germs are transplanted into the bodies of animal hosts, usually rodents, where there is sufficient blood flow to provide the necessary nutrients and oxygen to optimize tissue formation (Nakahara 2006).

Use of Stem Cells in Tissue Regeneration and Challenges Encountered.

Stem cells are quiescent cell populations present in normal tissue, which exhibit the distinct characteristic of asymmetric cell division, the formation two daughter cells—a new progenitor/stem cell, and another daughter cell capable of forming differentiated tissue (Hawkins 1998, Lin 1998). Dental mesenchymal progenitor cells have been identified and characterized in the dental pulp of both deciduous and adult human teeth (Gronthos 2000, Mooney 1996, Shi 2005). As previously mentioned, these postnatal epithelial and mesenchymal dental stem/progenitor cells present in immature tooth buds have demonstrated the ability to generate bioengineered and anatomically correct, but miniature-sized tooth crowns containing enamel, dentin, pulp, and alveolar bone (Shi 2005; Zhang 2005).

Periodontal ligament cells are known for their regenerative potential to give rise to the formation of lamina propria, cementum, bone, and periodontal ligament (Melcher 1985, McCulloh 1985). The capacity of periodontal ligament stem cells to form mineralized deposits in vitro has been demonstrated for a subpopulation of cells derived from primary explants of periodontal ligament (Arceo 1991, Cho 1992). It is believed that periodontal ligament stem cells require a suitable scaffold to induce the formation of bone, dentin and cementum in vivo (Gronthos 2000, Krebsbach 1998). When periodontal ligament stem cells were incorporated into a hydroxyapatite/tricalcium phosphate scaffolds and ectopically implanted in the subcutaneous regions of the mouse dorsum, a typical cementum/periodontal ligament-like structure formed (Seo 2004). Moreover, a type I collagen-positive periodontal ligament-like tissue within the transplants connecting with the newly formed cementum that is morphologically similar to Sharpey's fibers has been demonstrated (Seo 2004).

Recent advances in dental stem cell biotechnology and cell-mediated murine tooth regeneration have encouraged researchers to explore the potential for regenerating living teeth with appropriate functional properties (Duailibi 2004, Ohazama 2004, Shi 2005). Murine teeth can be regenerated using many different stem cells to collaboratively form dental structures in vivo (Duailibi 2004, Ohazama 2004, Young 2005). In addition, dentin/pulp tissue and cementum/periodontal complex have been regenerated by human dental pulp stem cells (DPSCs) and periodontal ligament stem cells (PDLSCs) respectively, when transplanted into immune-compromised mice (Gronthos 2000, Seo 2004). However, owing to the complexity of human tooth growth and development, the regeneration of a whole tooth structure including enamel, dentin/pulp complex, and periodontal tissues as a functional entity in humans is a challenge with the currently available regenerative biotechnologies (Sonomaya 2006).

The challenges with the use of stem cells in regeneration of dental tissues have been reported in previous studies (Duailibi 2004, Young 2002, Young 2005). It is acknowledged that, while formation of multiple miniature tooth crowns in the bioengineered tooth constructs is possible, real-size whole-tooth regeneration encounters a number of challenges. These challenges are attributed, again, to the complex nature of tooth development (Duailibi 2006, Tummers 2003).

Concepts of Cell Homing.

As put forward, conventional approaches of stem cell-seeding within a scaffold aim to mimic cellular structure and recreate a functional tissue equivalent in vitro or in vivo. The cells are derived from end organs or from more undifferentiated sources such as the bone marrow (Schantz 2007). These approaches are limited by issues such as donor site morbidity from harvesting of cells and tissue formation of heterogeneous quality at the site of implantation of the cell-scaffold construct (Schantz 2007). Hence, the concept of cell homing is recently attracting more attention. Cell homing aims to induce the homing of desired cells to cytokine-impregnated scaffolds at specific anatomical sites (Schantz 2007). This approach attempts in vivo tissue regeneration without cell-seeding. Therefore, cell homing could provide enhancements in cellular methodology for tissue engineering and a novel, minimally invasive option for tissue regeneration (Schantz 2007).

Based on the above discussion, further development of tooth scaffolds is needed. The present invention address that need.

SUMMARY

In some embodiments, an acellular mammalian tooth-shaped scaffold is provided. The scaffold comprises a compound that is chemotactic, osteogenic, dentinogenic, amelogenic, or cementogenic.

In other embodiments, a method of replacing a tooth in the mouth of a mammal is provided. In these embodiments, the tooth is absent and a tooth socket is present in the mouth at the position of the absent tooth. The method comprises implanting an acellular scaffold having the shape of the missing tooth into the tooth socket.

Additionally, methods of making a tooth scaffold is provided. The methods comprise synthesizing an acellular scaffold in the shape of a mammalian tooth and adding at least one compound that is chemotactic, osteogenic, dentinogenic, amelogenic, or cementogenic.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Figure 1:
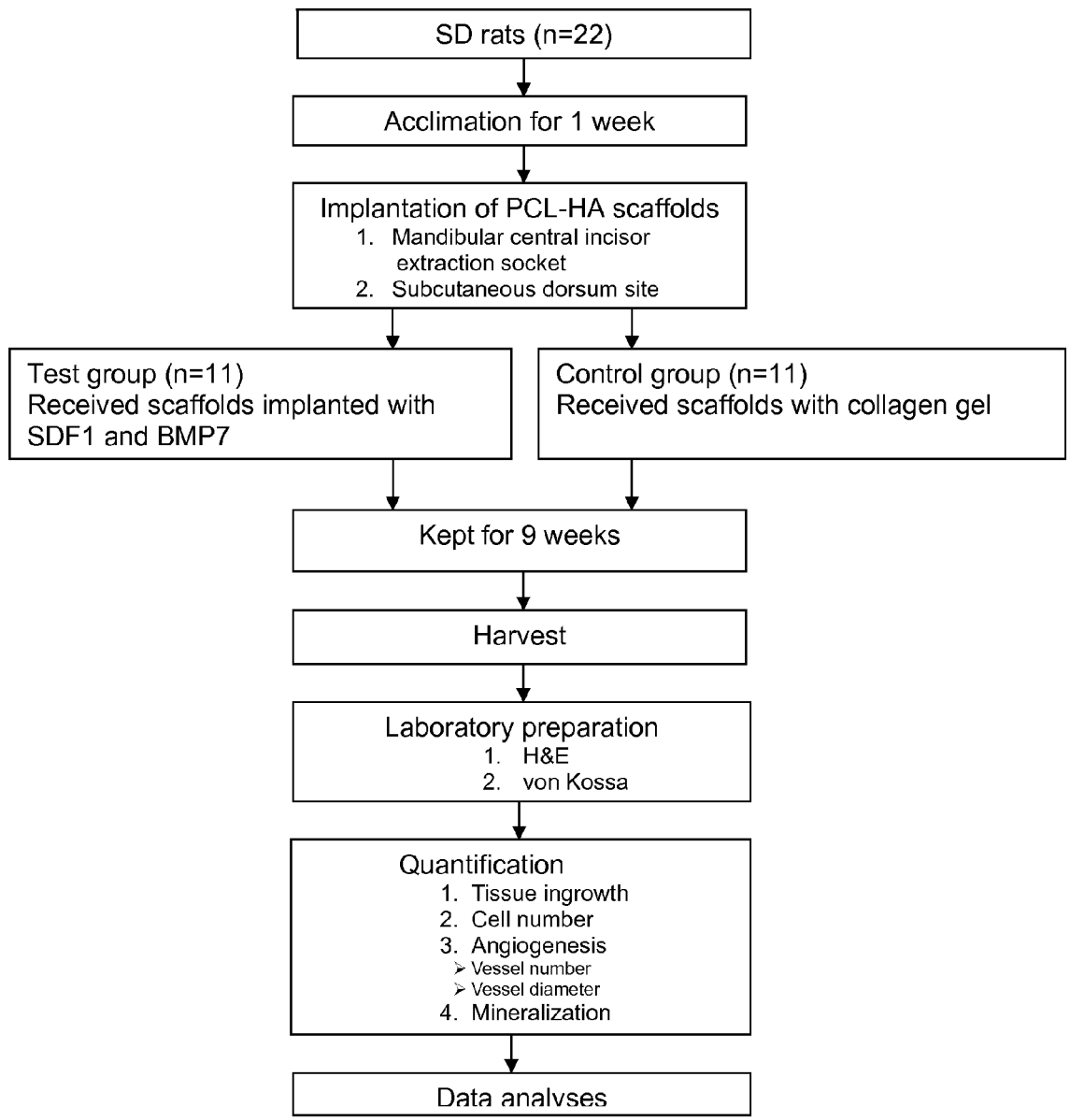
FIG. 1 is a flow chart showing the design of the study described in the Example.

The present invention is based in part on the surprising discovery that a tooth-shaped scaffold, when implanted into a tooth socket, will attract cells that colonize the scaffold to provide a living tooth, even without exogenously providing cells with the scaffold.

Thus, in some embodiments, an acellular mammalian tooth-shaped scaffold is provided. The scaffold comprises a compound that is chemotactic, osteogenic, dentinogenic, amelogenic, or cementogenic. These scaffolds are thus implanted without exogenously applied cells. As established in the Example, colonization of the implanted scaffolds proceeds adequately by native cells that migrate into the scaffold. The colonization is further encouraged by the chemotactic, osteogenic, dentinogenic, amelogenic, or cementogenic compound incorporated into the scaffold.

The compound can be of any structure including but not limited to a protein, oligopeptide, small organic molecule (i.e., less than about 2000 mw, or about 1000 mw or about 500 mw), metal ion-containing molecule, carbohydrate, or lipid. As used herein, a chemotactic compound is a compound that attracts cells. An osteogenic compound is a compound that encourages new bone synthesis. A dentinogenic compound is a compound that encourages new dentin synthesis. An amelogenic compound is a compound that encourages tooth enamel synthesis. A cementogenic compound is a compound that encourages cementum synthesis.

As used herein, a "scaffold" is a structure that provides a matrix for the growth of cells and/or the formation of tissue. Useful properties of a scaffold are porosity, biocompatibility and biodegradability, the ability to support cell growth, and its use as a controlled gene- and protein-delivery vehicle (Murphy 1999). The three-dimensional macromolecular structure provided by the scaffold is to guide the final shape of bioengineered tissues (Murphy 1999).

The scaffolds of these embodiments can have the shape of any mammalian tooth. In some of these embodiments, the scaffold has the shape of a human incisor, a human cuspid, a human bicuspid or a human molar.

The compound in these embodiments can be any compound that is chemotactic, osteogenic, dentinogenic, amelogenic, or cementogenic. Nonlimiting examples include platelet-derived growth factor (PDGF), endothelial cell growth factor (ECGF), transforming growth factor-β1 (TGF-β1), epidermal growth factor (EGF), hepatocyte growth factor (HGF), stromal cell-derived factor-1 (SDF1), a bone morphogenetic protein (BMP), a TGF-β, a growth and differentiation factor (GDF), insulin-like growth factor-1 (IGF1), vascular endothelial growth factor (VEGF), fibroblast growth factor (FGF), a dentin matrix protein, a dentin sialoprotein, a bone sialoprotein, amelogenin, or an integrin.

In some embodiments, the compound is SDF1, which has chemotactic properties. SDF1 is a chemokine that is believed to be essential in stem and progenitor cell recruitment for tissue repair after injury (Kollet 2003). SDF1 can also induce migration of hematopoietic progenitor cells within a chemotaxis chamber (Kim 1998). Additionally, SDF1 is important for the migration of marrow stromal cells to bone marrow, as shown by the dose-dependent migration of mesenchymal stem cells (MSCs) in response to stimulation with SDF1 (Win 2004). SDF1 also has anti-apoptotic properties, protecting hematopoietic stem cells directly from the apoptotic effects of γ-irradiation in the presence of other growth factors (Herodin 2003). Further, mesenchymal stem cells (MSCs) derived from bone marrow can be directed to migrate toward SDF1 (Schantz 2007).

In other embodiments, the compound is a BMP. BMP2, 6, and 9 are apparently the most potent agents for osteogenic differentiation of MSCs, while the rest of the BMPs are more effective in promoting the terminal differentiation of committed osteoblastic precursors and osteoblasts (Cheng 2003).

In some aspects of these embodiments, the BMP is BMP-7. BMP-7 plays a key role in the transformation of mesenchymal cells into bone and cartilage. BMP-7 treatment is sufficient to induce all of the genetic markers of osteoblast differentiation in various cell types (Chen 2004). It is noted that BMP-7 has received Food and Drug Administration (FDA) approval for human clinical uses.

Many studies have investigated the role and action of exogenous growth factors in a carrier to deliver the growth factor to an implantation site. Although the carrier may not contribute any additional factors necessary for tissue formation, it can still be an important component of the growth process (Wozney 1990). One of the carrier functions is to maintain the factor at the site of implantation and thus enhance its local concentration. The carrier also serves as an environment in which tissue can form and therefore helps to define the region in which new tissue can be formed (Whang 1998). Collagenous or synthetic carriers have been used as delivery vehicles, and their physicochemical properties, together with the microenvironment they create, play a role in the inductive outcome. Carriers can be solid xenogenic (e.g., hydroxyapatite) (Kuboki 1995, Murata 1998), solid alloplastic (polyethylene polymers) materials (Saito 1998, Isobe 1999), or gels of autogenous (Sweeney 1995, Schwartz 1998), allogenic (Bax 1999, Viljanen 1997), or alloplastic origin (Santos 1998), and combinations of the above (Alpaslan 1996).

One of the carrier functions is to maintain the factor at the site of implantation and thus enhance its local concentration. A collagen matrix retains up to 65% of BMPs during initial impregnation and releases it in two phases: an initial phase within hours of implantation and a second phase that depends on the nature of the carrier and its geometrical characteristics (Uludag 1999). It is believed that BMPs do not bind to the carrier (Uludag 1999), but rather become physically entrapped in its structure which makes certain designs more favorable for osteoinduction over others (Tsuruga 1997). In the case of collagen sponge carriers, mass, collagen cross-linking and sterilization methods affect BMP precipitation and subsequent resistance of sponge degradation by collagenase (Friess 1999). A collagen carrier can also result in increased bone density of the regenerate compared to the polymeric matrix (Cochran 1997).

BMP-7 plays a key role in the transformation of mesenchymal cells into bone and cartilage. BMP-7 treatment is sufficient to induce all of the genetic markers of osteoblast differentiation in various cell types (Chen 2004). It is also worthwhile to note that BMP-7 has received the Food and Drug Administration (FDA) approval for human clinical uses.

In some of these scaffolds, a chemotactic growth factor as well as a growth factor that is osteogenic, dentinogenic, amelogenic, or cementogenic is present. In particular embodiments, the chemotactic growth factor is SDF1 and the osteogenic, dentinogenic, amelogenic, or cementogenic growth factor is BMP-7.

The scaffolds of these embodiments can further comprise any other bioactive molecule, for example an antibiotic or an additional chemotactic growth factor or another osteogenic, dentinogenic, amelogenic, or cementogenic growth factor. In some embodiments, the scaffold is strengthened, through the addition of, e.g., human serum albumin (HSA), hydroxyethyl starch, dextran, or combinations thereof. Suitable concentrations of these compounds for use in the compositions of the application are known to those of skill in the art, or can be readily ascertained without undue experimentation.

The concentration of compound in the scaffold will vary with the nature of the compound, its physiological role, and desired therapeutic or diagnostic effect. A therapeutically effective amount is generally a sufficient concentration of therapeutic agent to display the desired effect without undue toxicity. In some embodiments, The scaffold comprises BMP-7 in the scaffold at about 10 ng/g to 1000 μg/g scaffold and SDF1 in the scaffold at about 10 ng/g to 1000 μg/g scaffold. In more specific embodiments, the BMP-7 is in the scaffold at about 100 μg/g scaffold and the SDF1 is in the scaffold at about 100 μg/g scaffold.

The compound can be incorporated into the scaffold by any known method. In some embodiments, the compound is imbedded in a gel, e.g., a collagen gel incorporated into the pores of the scaffold, as described in the Example.

Alternatively, chemical modification methods may be used to covalently link the compound on the surface of the scaffold. The surface functional groups of the scaffold can be coupled with reactive functional groups of the compound to form covalent bonds using coupling agents well known in the art such as aldehyde compounds, carbodiimides, and the like. Additionally, a spacer molecule can be used to gap the surface reactive groups and the reactive groups of the biomolecules to allow more flexibility of such molecules on the surface of the matrix. Other similar methods of attaching biomolecules to the interior or exterior of a matrix will be known to one of skill in the art.

The compound can alternatively be introduced into or onto the matrix via a carrier based system, such as an encapsulation vehicle. Such vehicles are useful as slow release compositions. For example, growth factors can be micro-encapsulated to provide for enhanced stability and/or prolonged delivery. Encapsulation vehicles include, but are not limited to, microparticles, liposomes, microspheres, or the like, or a combination of any of the above to provide the desired release profile in varying proportions. Other methods of controlled-release delivery of agents will be known to the skilled artisan. Moreover, these and other systems can be combined and/or modified to optimize the integration/release of agents within the matrix.

Polymeric microspheres can be produced using naturally occurring or synthetic polymers and are particulate systems in the size range of 0.1 to 500 μm. Polymeric micelles and polymeromes are polymeric delivery vehicles with similar characteristics to microspheres and can also facilitate encapsulation and matrix integration of the compounds described herein. Fabrication, encapsulation, and stabilization of microspheres for a variety of payloads are within the skill of the art (see e.g., Varde & Pack (2004) Expert Opin. Biol. 4(1) 35-51). The release rate of the microspheres can be tailored by type of polymer, polymer molecular weight, copolymer composition, excipients added to the microsphere formulation, and microsphere size. Polymer materials useful for forming microspheres include PLA, PLGA, PLGA coated with DPPC, DPPC, DSPC, EVAc, gelatin, albumin, chitosan, dextran, DL-PLG, SDLMs, PEG (e.g., ProMaxx), sodium hyaluronate, diketopiperazine derivatives (e.g., Technosphere), calcium phosphate-PEG particles, and/or oligosaccharide derivative DPPG (e.g., Solidose). Encapsulation can be accomplished, for example, using a water/oil single emulsion method, a water-oil-water double emulsion method, or lyophilization. Several commercial encapsulation technologies are available (e.g., ProLease®, Alkerme).

Liposomes can also be used to integrate compounds with the scaffolds. The agent carrying capacity and release rate of liposomes can depend on the lipid composition, size, charge, drug/lipid ratio, and method of delivery. Conventional liposomes are composed of neutral or anionic lipids (natural or synthetic). Commonly used lipids are lecithins such as phosphatidylcholines, phosphatidylethanolamines, sphingomyelins, phosphatidylserines, phosphatidylglycerols, and phosphatidylinositols. Liposome encapsulation methods are commonly known in the arts (Galovic et al. (2002) Eur. J. Pharm. Sci. 15, 441-448; Wagner et al. (2002) J. Liposome Res. 12, 259-270). Targeted liposomes and reactive liposomes can also be used in combination with the agents and matrix. Targeted liposomes have targeting ligands, such as monoclonal antibodies or lectins, attached to their surface, allowing interaction with specific receptors and/or cell types. Reactive or polymorphic liposomes include a wide range of liposomes, the common property of which is their tendency to change their phase and structure upon a particular interaction (e.g., pH-sensitive liposomes). See, e.g., Lasic (1997) Liposomes in Gene Delivery, CRC Press, FL).

The scaffolds of these embodiments can be fabricated with any material recognized as useful by the skilled artisan. Suitable matrix materials are discussed in, for example, Ma and Elisseeff, ed. (2005) Scaffolding in Tissue Engineering, CRC, ISBN 1574445219; Saltzman (2004) Tissue Engineering: Engineering Principles for the Design of Replacement Organs and Tissues, Oxford ISBN 019514130X. Nonlimiting examples of potentially useful materials for all or part of the scaffold include poly(ethylene) glycol, poly(lactide), poly (glycolic acid), poly(lactide-co-glycolide), poly(caprolactone), polyanhydride, polyglactin, polycarbonates, polyamides, polyanhydrides, polyamino acids, polyortho esters, polyacetals, polycyanoacrylates), polyphosphazene, degradable polyurethanes, polyacrylates, ethylene-vinyl acetate polymers and other acyl substituted cellulose acetates and derivatives thereof, polyurethanes, polystyrenes, polyvinyl chloride, polyvinyl fluoride, polyvinyl pyrrolidone, poly(vinylimidazole), chlorosulphonated polyolifins, polyethylene oxide, polyvinyl alcohol, Teflon®, nylon, agarose, alginate (e.g., calcium alginate gel), fibrin, fibrinogen, fibronectin, collagen (e.g., a collagen gel), gelatin, hyaluronic acid, chitin, and other suitable polymers and biopolymers, or analogs, mixtures, combinations, and derivatives of the above.

In some embodiments, the scaffold is fabricated from a composition that comprises an osteoconductive material. A nonlimiting example of an osteoconductive material is hydroxyapatite (HA). HA has been used as a bone substitute for many years because of its excellent biocompatibility and high bioactivity (Liao 2006, Nebahat 2006, Lijun 2006, Wei 2003).

Although HA has good bioactivity and osteoconductivity, it is very brittle and has poor inherent tensile properties. Therefore, in some embodiments, the HA is combined with ε-polycaprolactone (PCL). PCL is a good bone scaffold material because it takes several years to degrade in vivo and is biocompatible, relatively inexpensive, and available in large quantities (Rich 2002, Kim 2004). The combination of PCL and HA (PCL-HA) provides a desirable combination of bioactivity, biodegradability, and strength (Patcharaporn 2005, Rezwan 2006, Landis 1995, Ziv 1994). The material of composite PCL-HA has been deemed to possesses the optimal scaffold properties of biocompatibility, cell-adhesion, proliferation, and differentiation (Zhao 2008). In some embodiments, the scaffold comprises a mixture of about 80 wt % polycaprolactone and about 20 wt % hydroxyapatite. In other embodiments, the scaffold comprises anywhere from about 60 wt % polycaprolactone and about 40 wt % hydroxyapatite to about 95 wt % polycaprolactone and about 5 wt % hydroxyapatite. For example, the scaffold can comprise about 70 wt % polycaprolactone and about 30 wt % hydroxyapatite. As another example, the scaffold can comprise about 90 wt % polycaprolactone and about 10 wt % hydroxyapatite.

In some embodiments, the scaffold has a high porosity. Such a porous structure provides space for cell migration, adhesion, and the ingrowth of new bone tissue (Gazdag 1995, Rezwan 2006, Mano 2004, Shin 2003, Kim 2001, Leong 2003).

Pores and channels of the scaffold can be engineered to be of various diameters. For example, the pores of the scaffold can have a diameter range from micrometers to millimeters. In some embodiments, the pores of the matrix material include microchannels. Microchannels generally have an average diameter of about 0.1 µm to about 1,000 µm, e.g., about 50 µm to about 500 µm (for example about 100 µm, 150 µm, about 200 µm, about 250 µm, about 300 µm, about 350 µm, about 400 µm, about 450 µm, about 500 µm, or about 550 µm). One skilled in the art will understand that the distribution of microchannel diameters can have any distribution including a normal distribution or a non-normal distribution. In some embodiments, microchannels are a naturally occurring feature of the matrix material(s). In other embodiments, microchannels are engineered to occur in the matrix materials.

In some embodiments, the compound is imbedded in a gel in the microchannels. Any gel can be used for this purpose. In some embodiments, the gel is a collagen gel.

In various embodiments, the scaffold further comprises a nonporous cap. Such a cap provides further strength to the scaffold and prevents infection. The nonporous cap can be simply the same material of the rest of the scaffold except without pores. Alternatively, the nonporous cap can be a different material, e.g., typical dental cap material, such as porcelain or gold.

Methods of replacing a tooth in the mouth of a mammal is also provided herein. In these embodiments, the tooth is absent and a tooth socket is present in the mouth at the position of the absent tooth. The methods comprise implanting an acellular scaffold having the shape of the missing tooth into the tooth socket.

Several methods are used for fabrication of porous scaffolds, including particulate leaching, gas foaming, electrospinning, freeze drying, foaming of ceramic from slurry, and the formation of polymeric sponge (Mikos 1994, Mooney 1996, Qing 2002, Sylvain 2006). However, scaffolds prepared by using these methods have some shortcomings in controlling the structure and interconnectivity of pores, which may limit their application in terms of cell penetration in tissue engineering (Yeong 2004, Tan 2003).

In some embodiments, the methods further comprise making a model of the absent tooth by computer aided design (CAD) and synthesizing the scaffold with a bioplotter. Such methods can provide scaffolds with high porosity and good interconnectivity. As described in the Example, three-dimensional (3D) scaffolds with controllable and reproducible porosity and well-defined 3D microstructures can be made. Rapid prototyping (RP) methods such as fused deposition modeling, selective laser sintering, 3D printing, multiphase jet solidification, and 3D plotting have been proposed (Hutmacher 2001, Moroni 2006).

A key feature of rapid prototyping is the solid freeform fabrication (SFF) process: 3D computer models are cut into sequences of layers which are used to construct complex objects layer-by-layer. The layers are produced via solidification of melts, layer photopolymerization or bonding of particles using either laser beam induced sintering (selective laser sintering) or special binders (Landers 2002). Recently, a specialized rapid prototyping system (Bioplotter™, EnvisionTec, Germany) has been introduced, enabling the design and fabrication of anatomically shaped scaffolds with varying internal architectures, thereby allowing precise control over pore size, porosity, permeability, and stiffness (Landers 2002; Landers 2005). The prototyping process using the Bioplotter™ for fabricating a tissue-specific PCL-HA scaffold requires 3D morphological information of the target tissue or tissue defect, which can be obtained by computer tomography (CT) or magnetic resonance imaging (MRI). When an absent tooth has a counterpart on the other side of the mouth, that counterpart can be used as a model to design the scaffold for the missing tooth.

Information obtained above is then used to design a functional scaffold by CAD and is transferred to the Bioplotter™ system. In that system, the Bioplotter™ machine melts and dispenses the scaffold material (e.g., PCL-HA) in layer-by-layer on a collecting plate. Pores, for example microchannels, can be created as part of the design. The fabricated 3D scaffolds through the RP system result in significant cell penetration, and thus possess the properties of ideal scaffolds (Heo 2007). These 3D scaffolds may have potential for clinical application by providing patient tissue-specific anatomical shape as well as an optimized internal microstructure for the nutrient transportation and vascularization. Further details of these methods are provided in PCT Publication WO2009006558, incorporated by reference.

A method of making a tooth scaffold is additionally provided. The method comprises synthesizing an acellular scaffold in the shape of a mammalian tooth and adding at least one compound that is chemotactic, osteogenic, dentinogenic, amelogenic, or cementogenic. In some embodiments of these methods, the tooth is shaped like a tooth that is absent in a mammal, and the method further comprises making a model of an absent tooth by computer aided design (CAD), and synthesizing the scaffold with a bioplotter. Where the absent tooth has a counterpart in the mouth, e.g., a molar, the method further comprises making a CT scan of the analogous molar, for example on the other side of the mouth, where the CAD utilizes CT scan data of the second molar to design the scaffold.

In some embodiments of these methods, the compound is platelet-derived growth factor (PDGF), endothelial cell growth factor (ECGF), transforming growth factor-β1 (TGF-β1), epidermal growth factor (EGF), hepatocyte growth factor (HGF), stromal cell-derived factor-1 (SDF1), a bone morphogenetic protein (BMP), a TGF-β, a growth and differentiation factor (GDF), insulin-like growth factor-1 (IGF1), vascular endothelial growth factor (VEGF), fibroblast growth factor (FGF), a dentin matrix protein, a dentin sialoprotein, a bone sialoprotein, amelogenin, or an integrin.

In other embodiments, the scaffold is fabricated from a composition that comprises an osteoconductive material. As discussed above, an example of a useful osteoconductive material is hydroxyapatite. A further example is a mixture of ε-polycaprolactone and hydroxyapatite as discussed above. In various embodiments of these methods, the scaffold comprises microchannels having a diameter of between 50 and 500 μm. In additional embodiments, the scaffold further comprises a nonporous cap.

In some embodiments, numbers expressing quantities of ingredients, properties such as molecular weight, reaction conditions, and so forth, used to describe and claim certain embodiments of the invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Regeneration of Anatomically Correct Tooth by Cell Homing

One of the fundamental missions of dentistry is the restoration of diseased, missing and lost dental structures. Currently, conventional treatment of tooth loss includes prosthodontic management with or without surgically placed dental implants. Dental implants, despite their reported high success rates, are not without complications such as loosening, infection, and bone loss. Recently, there has been a common aspiration among practitioners and scientists that separate tooth structures or an entire tooth can be regenerated using biomedical engineering cues. This emerging area, however, has encountered several obstacles, not the least of which is the complexity of regeneration and the morphology of tooth structures. The present study proposes to establish the regeneration of an entire tooth organ with bioengineered tooth scaffolds and by delivery of growth factors known to be important in tooth development. Full size human tooth scaffolds were first fabricated by rapid prototyping with layer deposition of hybrid of ε-polycaprolactone and hydroxyapatite (PCL-HA) using the Bioplotter™ machine. In parallel, scaffolds in the shape of mandibular central incisor root of Sprague Dawley rats were also constructed in 3D. The scaffolds were then infused with stromal cell derived factor-1 (SDF1) and bone morphogenetic protein 7 (BMP-7). There were 22 Sprague Dawley rats—11 each in the test and control groups. In each of the rats, a human mandibular molar shaped scaffold was subcutaneously implanted in the dorsum site, and a rat mandibular incisor root shaped scaffold was implanted into the extraction socket after surgical extraction of one of the two mandibular central incisors. The test group scaffolds were impregnated with SDF1 and BMP-7 while the control group scaffolds contained no growth factors. All implanted scaffolds were harvested at 9-week post-implantation and histologically evaluated for tissue ingrowth, cellular penetration, angiogenesis and mineralization.

Materials and Methods.

Approval from Columbia University Institutional Animal Care and Use Committee (IACUC) was obtained prior to the commencement of this study. This study used the mandibular central incisor extraction sockets and subcutaneous dorsum sites of twelve-week old male Sprague Dawley rats (Charles River, N.Y.). All sites received PCL-HA scaffolds. There were a total of twenty-two SD rats randomly divided into two groups of eleven rats in each of two groups: a test group and a control group. As shown in FIG. 1, each rat was given an identification number—#1 to #11, and #12 to #22—test and control groups, respectively. The rats were maintained in pairs during the one-week acclimation period after purchase, in a twelve-hour light/dark cycle and were fed rat chow (Rodent Laboratory Chow 5001, Ormond Veterinary Supply, Ontario, Canada) and water ad labium before the surgical procedures for scaffold implantation. Table 1 summarizes the study groups and number of scaffolds implanted.

TABLE 1

Study groups and number of scaffolds implanted.

|  | Test | | Control | |
|---|---|---|---|---|
|  |  |  |  |  |
| Total Subject Number | 11 | | 11 | |
| Implantation Sites | E | D | E | D |
|  | n = 11 | n = 11 | n = 11 | n = 11 |

E = extraction socket site implantation;
D = subcutaneous dorsum implantation.

Each experimental site per rat—mandibular central incisor extraction socket and subcutaneous dorsum—surgically received one PCL-HA scaffold. The extraction socket site received a scaffold that resembled the root of the mandibular central incisor. The dorsum site received a scaffold that was in the shape of the human mandibular molar. The scaffolds implanted in the test group rats were impregnated with SDF1 and BMP-7, while the control group received the scaffolds with collagen gel only. All rats were kept for nine weeks post-surgery prior to the harvest of scaffolds for laboratory analyses and quantification.

Scaffold Preparation.

Figure 2:
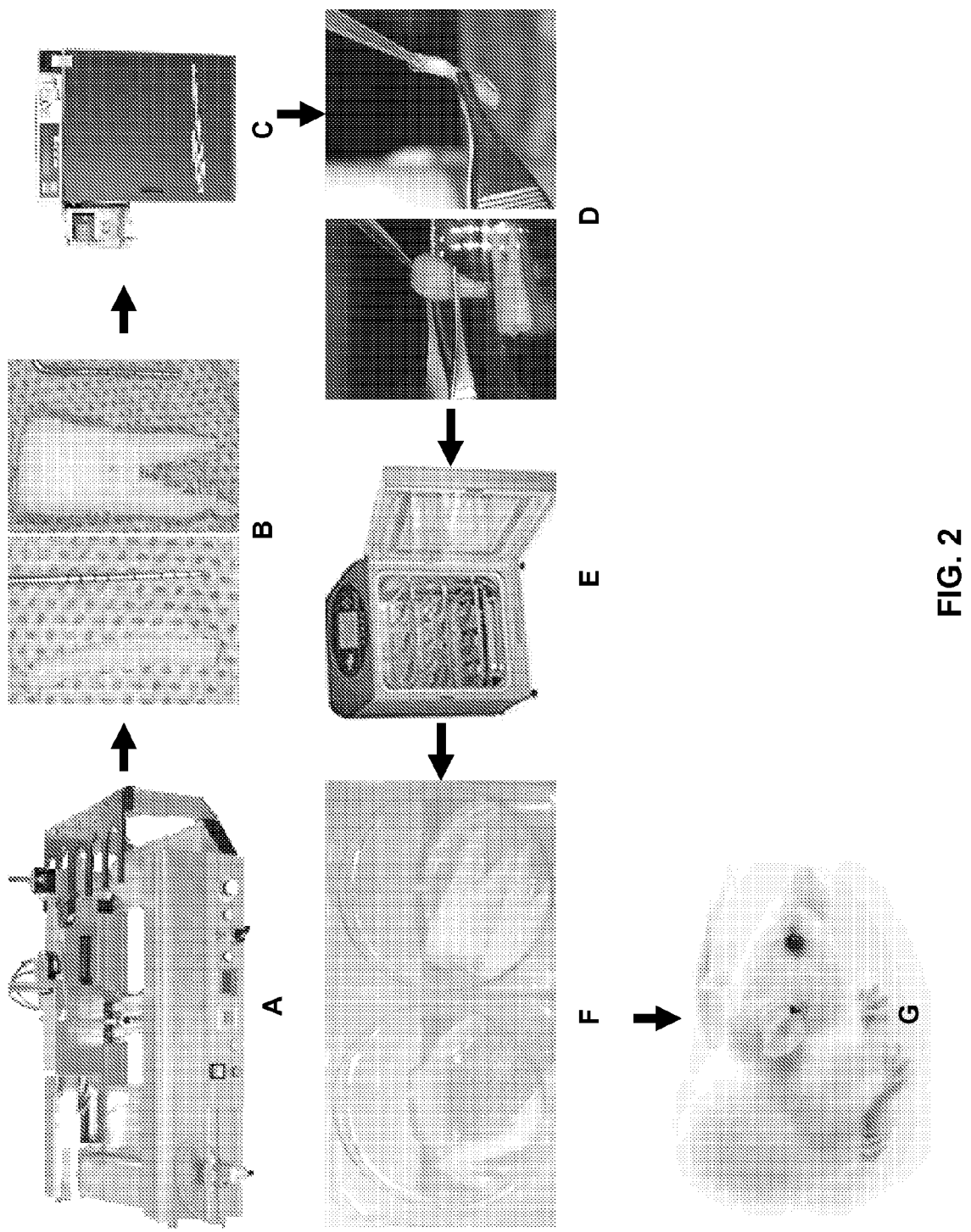
FIG. 2 is photographs showing scaffold fabrication using a 3D printing system (Bioplotter™). Panel A shows the Bioplotter™ used to create the scaffolds; Panel B shows a fabricated rat mandibular central incisor root (left) and human molar-shaped PCL-HA scaffold (right); Panel C shows the ethylene oxide sterilizer used to sterilize the scaffolds; Panel D shows scaffolds being treated with growth factors (SDF1 and BMP-7); Panel E shows the scaffold incubated for collagen cross-linking in the scaffolds prior to implantation; Panel F shows scaffolds being loaded by the growth factors and collagen gel; Panel G show scaffolds implanted in rats at the extraction socket and dorsum sites.
Figure 3:
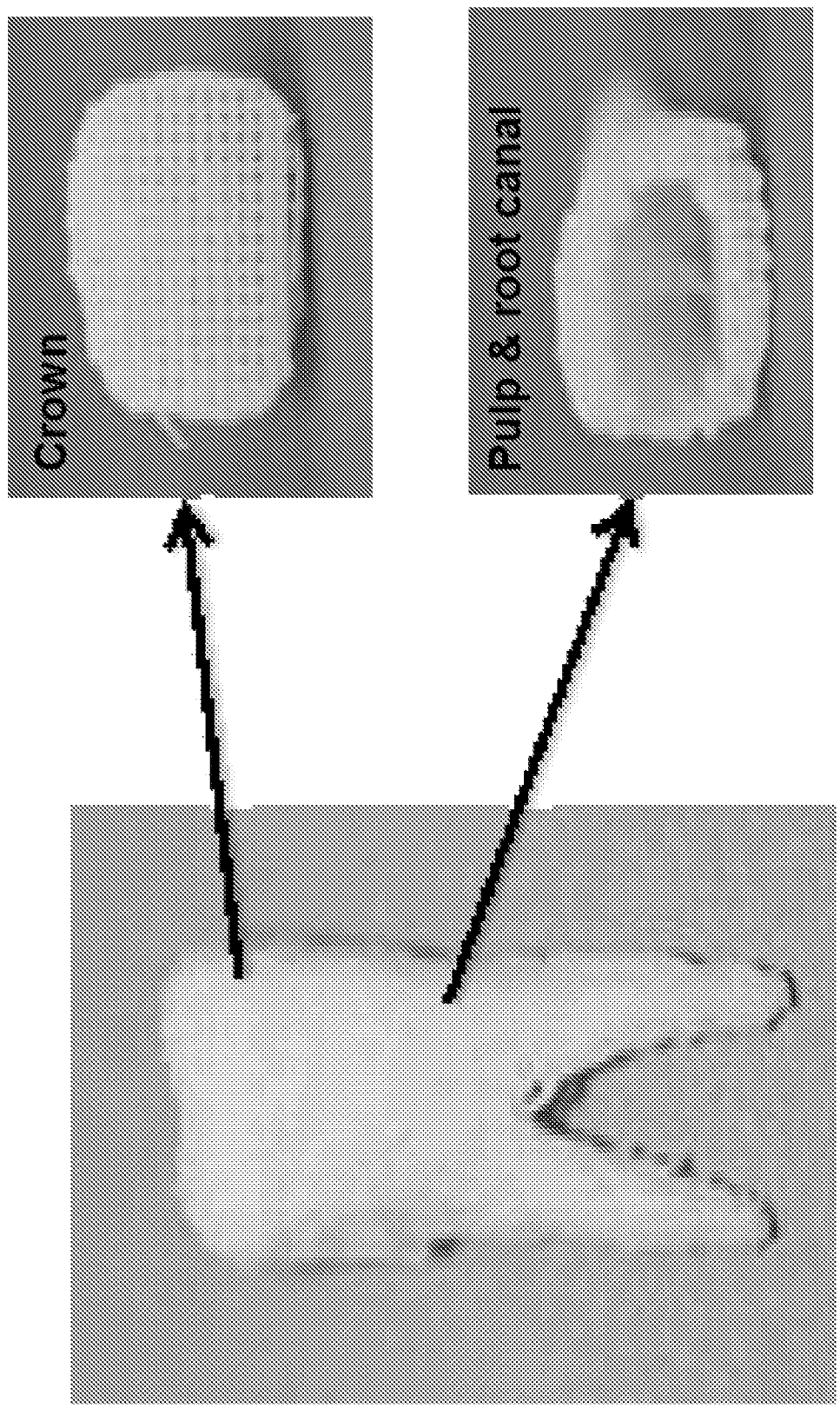
FIG. 3 is photographs of fabricated human mandibular molar-shaped scaffold for implantation in a rat dorsum. The crown and root were fabricated separately and fused later. The microchannels are evident.

The rat mandibular central incisor root shaped and human mandibular molar shaped PCL-HA scaffolds were fabricated by layer-by-layer deposition using a 3D printing system (Bioplotter™, Envision TEC, Gladbeck, Germany) (FIG. 2A, B). The composite consisted of 80 wt % polycaprolactone (PCL) (Mw ~65,000, Sigma, St. Louis, Mo.) and 20 wt % of hydroxyapatite (HA) (Sigma, St. Louis, Mo.). PCL-HA was molten in the chamber at 120° C. and dispensed through a 27-gauge metal needle (DL technology, Haverhill, Mass.) to create interlaid strands and interconnected microchannels (FIG. 3). The crown and root structures of the human mandibular molar-shaped scaffolds were produced individually and later fused to form the whole tooth due to difficulties encountered in its continuous fabrication as a one piece (FIG. 3). All scaffolds included microchannels of 200 μm in diameter created by the interlocking structure of the PCL-HA strands of 200 μm in diameter (FIG. 3). The macromolecular 3D structure of the scaffold was meant to contribute to formation of the outer morphology of the final outcome while the internal architecture with microchannels aimed to provide room for cellular occupation and tissue ingrowth. All fabricated scaffolds were sterilized in an ethylene oxide sterilizer for twenty-four hours prior to treatment with collagen gel containing SDF1 and BMP-7 (test group), and collagen gel without a growth factor (control group) (FIG. 2C). The treatment of the scaffolds was performed in a laminar flow hood using sterile laboratory techniques.

For the test group, 100 ng/ml stromal cell-derived factor-1 (SDF1) (R&D systems, MN) and 100 ng/ml bone morphogenic protein-7 (BMP-7) (R&D systems, MN) were combined in 2 mg/ml neutralized bovine type I collagen (Cultrex®, R&D Systems, Minneapolis, Minn.). The growth factor-collagen solution was then infused into microchannels in the PCL-HA scaffold and cross-linked for 1 hr in a humidified incubator at 37° C. Collagen gel loaded with SDF1 and BMP-7 was prepared in the mixture of PBS, 10×PBS, NaOH as summarized in Table 2. The dose of SDF1 and BMP-7 were selected based on previous works. Chemotaxis assays have shown that mesenchymal stem cells grow toward an SDF1 stimulus with maximal chemotaxis at a concentration of 100 ng/ml (Schantz 2007). The BMP-7 concentration of 100 ng/ml has been shown to be effective in promoting osteoblast growth on the collagen carrier (Laflamme 2008). The control group scaffolds were not loaded with any growth factor after sterilization. Rather, empty collagen gel was infused into the microchannels in the same manner as described for the test group prior to the surgery.

TABLE 2

Details of the growth factor solution delivered into the test group scaffolds.

| Contents | Amount (ml) |
|---|---|
| 10X PBS | 1 |
| 1N NaOH | 0.14 |
| PBS | 4.86 |
| Collagen I | 2 (5 mg/ml) |
| BMP7 | 1 (100 ng/ml) |
| SDF1 | 1 (100 ng/ml) |
| Total Volume | 10 |

Surgical Procedures.

Twelve-week old Sprague Dawley rats (Charles River, N.Y.) were purchased and were allowed to acclimate for approximately one week. All rats were anesthetized with the cocktail of ketamine (80 mg/kg, IP) and xylazine (5 mg/kg, IP). Depth of anesthesia was monitored during the procedure by toe-pinch; and when required, ketamine (⅓ of full dose: 25 mg/kg, IP) alone was given to maintain anesthesia depth as necessary. A pulse-oximeter device was used during the surgery to monitor the pulse rate and the oxygen saturation level.

Figure 4:
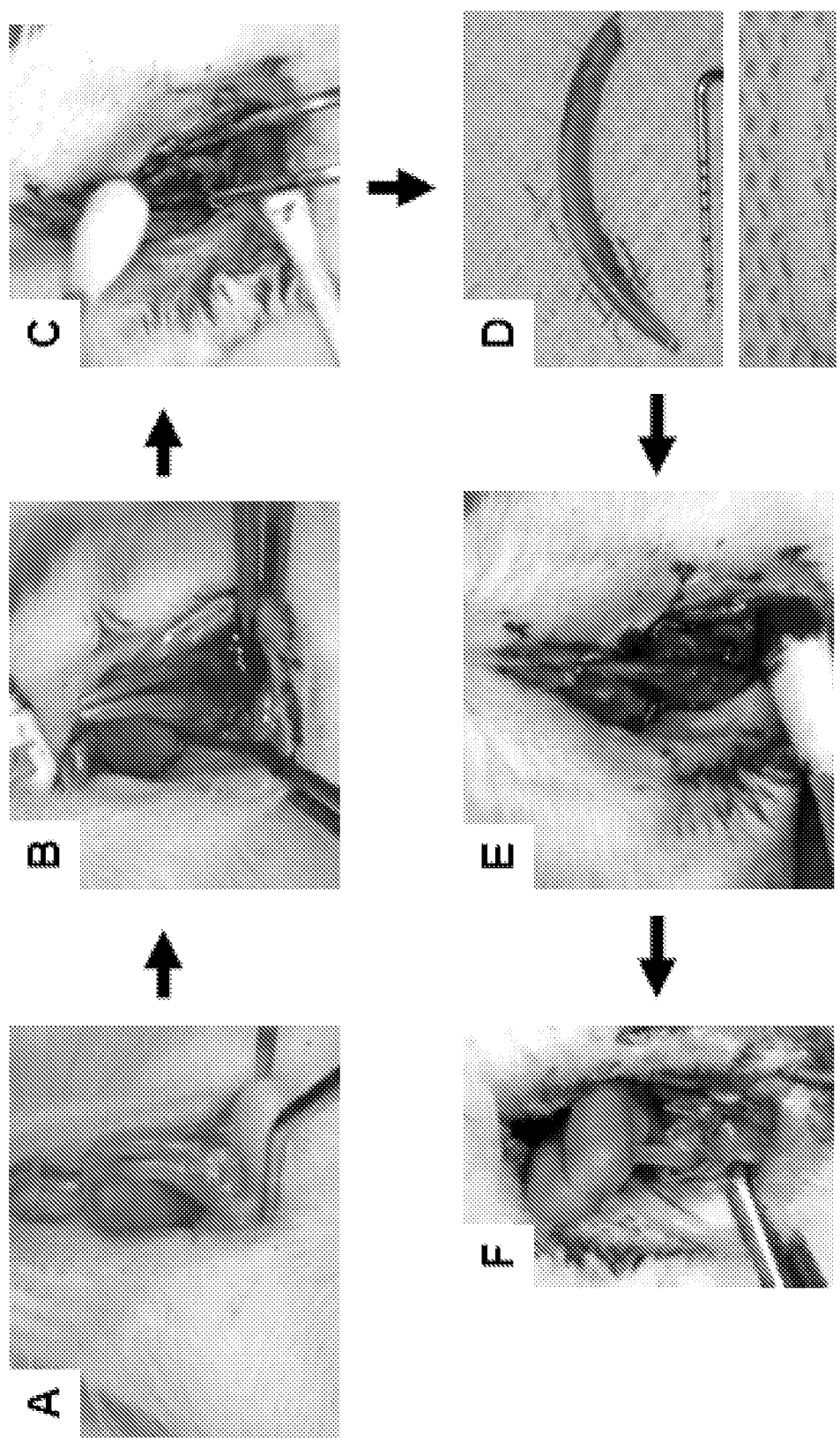
FIG. 4 is photographs of the extraction of a mandibular central incisor followed by implantation of a root-form scaffold in the socket. Panel A shows the retraction of the lower lip; Panel B shows incision and reflection of the gingival flap; Panel C shows atraumatic extraction of the left mandibular central incisor showing preserved bony walls of the socket; Panel D shows the extracted incisor and root-form scaffold in comparison; Panel E shows the scaffold implanted in the extraction socket; Panel F shows the gingival flap sutured and primarily closed.
Figure 5:
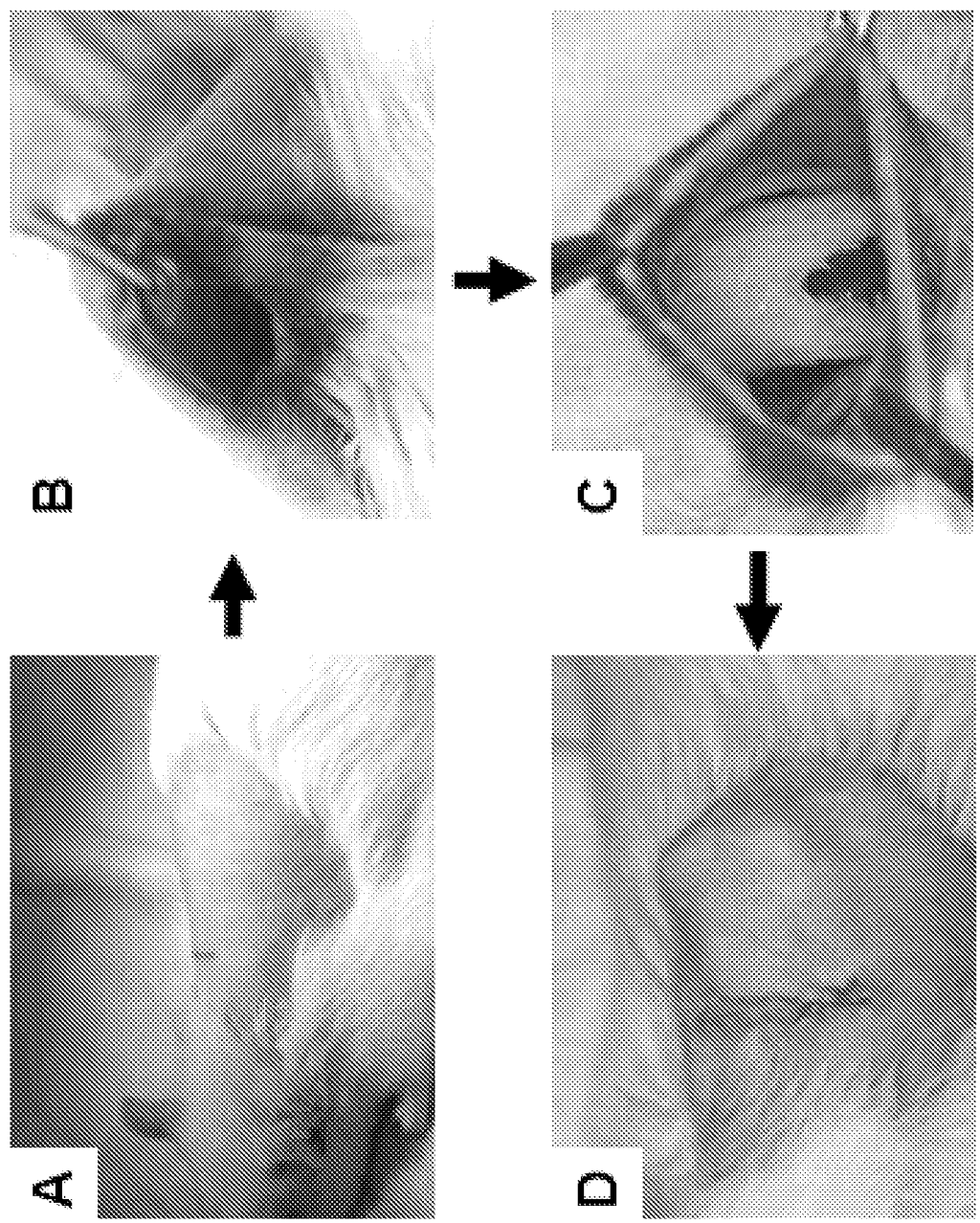
FIG. 5 is photographs of the subcutaneous implantation of a human mandibular molar-shaped scaffold in a rat dorsum site. Panel A shows a 2-cm incision being made; Panel B shows the creation of a subcutaneous pouch; Panel C shows the implantation of a scaffold into the pouch; Panel D shows the primary closure.

The surgical techniques were identical between the two groups (FIGS. 4, 5). Careful, atraumatic surgical extraction of a mandibular central incisor was performed followed by immediate implantation of the root-form scaffold into the extraction socket (FIG. 4C, D, E). The extraction procedure was done as atraumatically as possible using periotomes, taking care to preserve the bony walls of the socket (FIG. 4C). During the implantation of the construct, care was taken to preserve the labial walls by passive fitting of the construct (FIG. 4E). After implantation, the flap was advanced for primary closure and each socket was closed with one or two single-interrupted sutures, using the polyglylactin suture material (Vicryl 5-0, Johnson and Johnson, NJ) (FIG. 4F).

At the dorsum site of the same rat, subcutaneous implantation of the prepared human mandibular molar-shaped scaffold was performed (FIG. 5). A 2-cm long horizontal incision was placed and the subcutaneous area was relieved and pouched using a sharp surgical scissor (FIG. 5B). A human mandibular molar-shaped scaffold was implanted in the pouch created subcutaneously (FIG. 5C). The site was closed with polyglylactin suture material (Vicryl 5-0, Johnson and Johnson, NJ) making sure that there was no entrapped air bubble before closure (FIG. 5D). Multiple single-interrupted sutures were placed for primary closure.

Upon completion of the implantation procedures, buprenorphine (0.05 mg/kg, IP) was given for analgesia prior to relocating to the animal intensive care unit. The rats were monitored closely by veterinary technicians during the recovery period of three to five days and kept in single occupancy cages in a twelve-hour light/dark cycle and fed rat chow (Rodent Laboratory Chow 5001, Ormond Veterinary Supply, Ontario, Canada) and water ad libitum for nine weeks before being euthanized. During the nine-week period, the rats were closely monitored on a regular basis for any sign of infection or illness. Proper management was carried out when such a sign was observed. The remaining incisors were monitored for their continual growth to avoid malocclusion and resultant malnutrition. When indicated, the teeth were clipped for ease of mastication. At the ninth week post-surgery, each rat was humanely euthanized immediately before the harvest using overdose of pentobarbital injection IP.

Harvest and Laboratory Procedures.

Prior to the harvest, it was evident that the gingival tissues over the mandibular central incisor extraction socket had been maintained without exposure of the scaffolds (FIG. 6A). The dorsum sites also showed its optimal wound healing (FIG. 7A).

Figure 6:
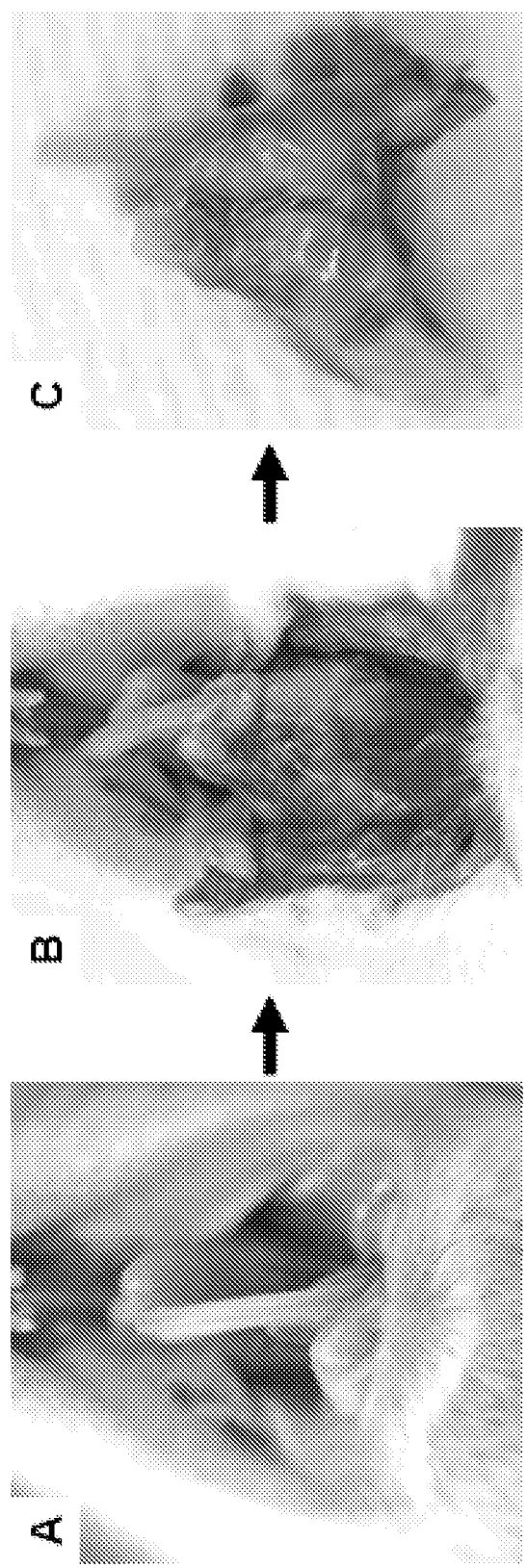
FIG. 6 is photographs showing en bloc harvest of the mandibular central incisor scaffold. Panel A shows complete wound healing which was evident before the harvest; Panel B shows an incision made to access the scaffold; Panel C shows the en bloc harvest of the scaffold (right) and the adjacent incisor (left).
Figure 7:
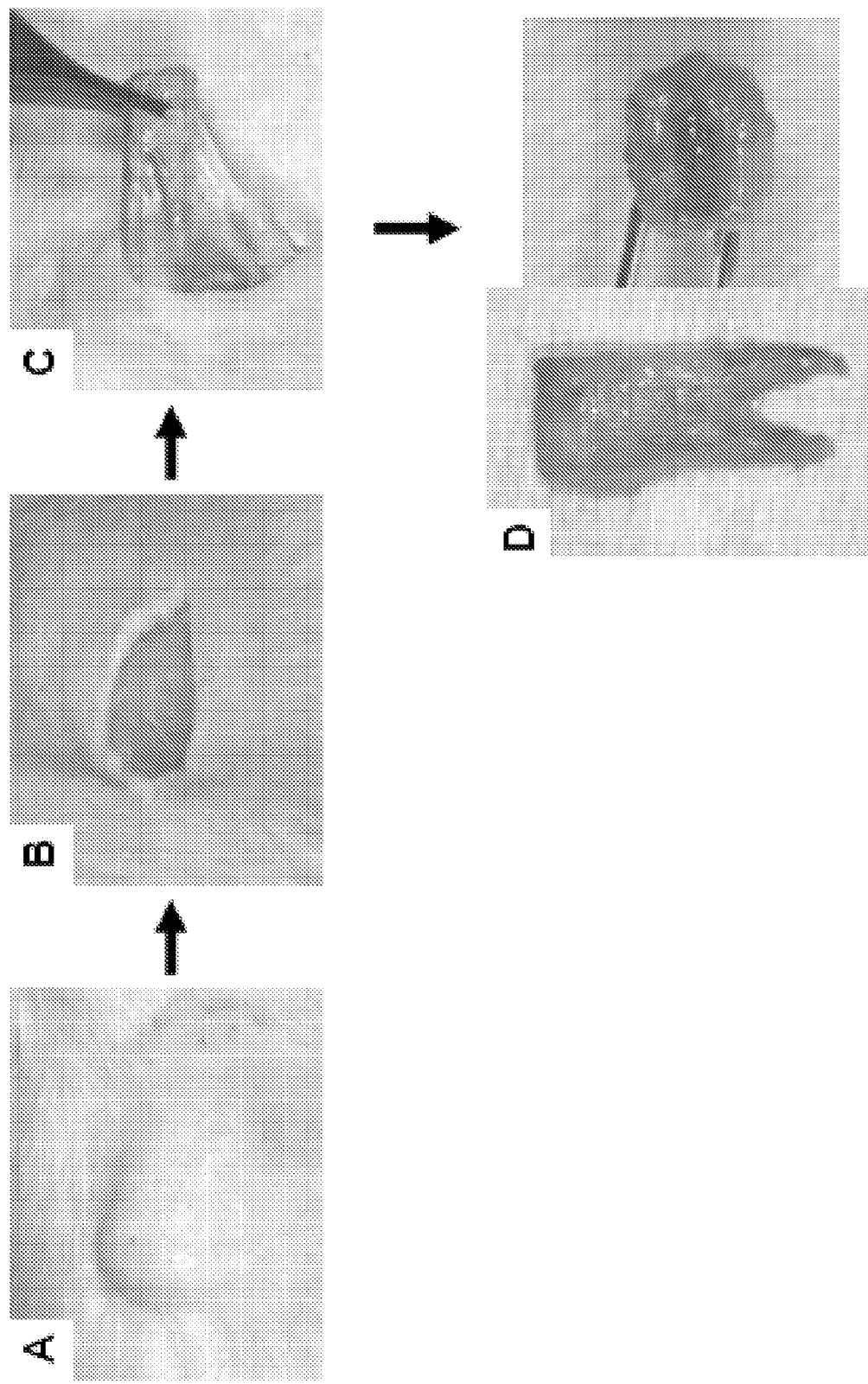
FIG. 7 is photographs showing the procedure for implanted scaffold harvest at the dorsum site. Panel A shows complete wound healing prior to the harvest; Panel B shows the incision made to access the scaffold; Panel C shows fascial encapsulation of the scaffold; Panel D shows retrieved scaffolds.

The scaffolds in the mandible were harvested en bloc including the remaining adjacent central incisor and alveolar bone (FIG. 6). The dorsum scaffolds were retrieved with the surrounding fascia encapsulating the scaffolds (FIG. 7). All harvested constructs were stored in 10% formalin prior to transportation to the histology lab for 5 μm-thick slide preparations and hematoxylin and eosin (H&E) and von Kossa (VK) staining of each specimen.

Quantification of Cell Homing, Vascularization and Mineralization.

Quantification of cell homing, vascularization and mineralization was based on any observed differences in cellular density, angiogenesis (blood vessel number and diameter), and presence of mineralization between the study groups and implantation sites.

Figure 8:
FIG. 8 is micrographs of stained scaffold sections showing the regions selected for histological analyses. Panel A shows three regions selected in the mandibular central incisor scaffold; Panel B shows four regions selected in the human mandibular molar scaffold.
Figure 8:
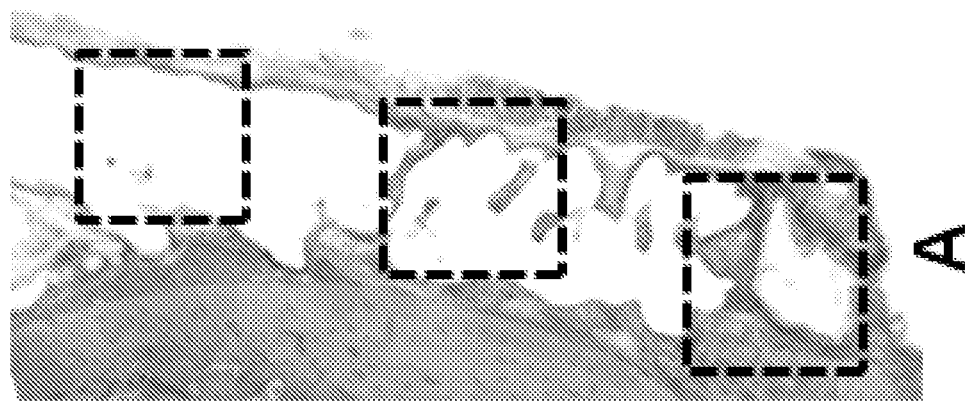

The quantification procedures were performed by a blinded examiner who was not aware which rat belonged to which group. Prior to examining the slides of each scaffold, a decision was made as to which areas would contribute to the histological data analysis. It was agreed to look at the mid-regions of coronal third, middle third, and apical third of the scaffolds prepared on the slides as shown in FIG. 8. Hence, the scaffold harvested from the extraction socket had three regions evaluated (FIG. 8A), while the scaffold from the dorsum site had four regions evaluated due to the presence of the two roots (FIG. 8B). Each slide was examined thoroughly using a digital research microscope (Leica DM6000, Leica, Switzerland) at 100× magnification. The slide photos were taken digitally. The software program provided with the microscope, Leica Application Suite (LAS), was used to carry out quantification of cells and blood vessels within the agreed regions. The counts were later converted into number/$mm^2$. The blood vessel diameter was measured using a computer software program (Photoshop CS) and converted into millimeters (mm). Presence or absence of mineralization was evaluated also.

Statistical Analyses.

All statistical analyses were carried out using a computer program (Microsoft Office Excel 2007). For each variable previously mentioned, mean average and standard deviation values were calculated. Student t-tests were carried out to determine the level of significance between the two experimental groups and between the implantation sites. A p-value <0.05 was considered significant.

Results

Tissue Integration with the PCL-HA Scaffolds.

Figure 9:
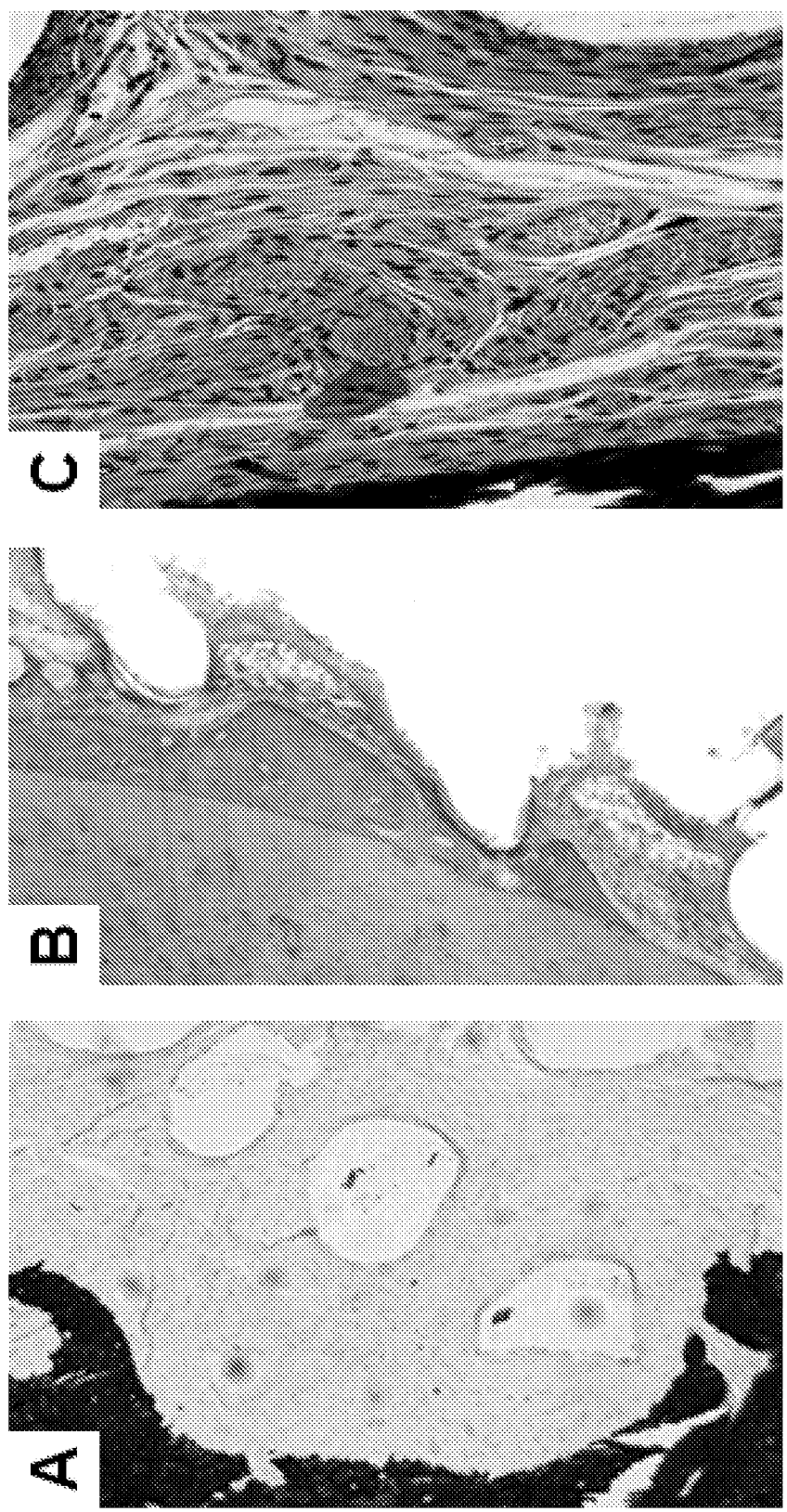
FIG. 9 is micrographs of stained scaffold sections showing the tissue-scaffold interface of an incisor root-form scaffold within the extraction socket (test and control groups). Panel A shows a von Kossa (VK)-stained slide depicting bony ingrowth at the interface; Panel B shows a hematoxylin and eosin (H&E)-stained section showing close adaptation and integration of the scaffold to the socket wall; Panel C shows a higher magnification view demonstrating evident angiogenesis and soft tissue ingrowth between the PCL-HA strands.
Figure 10:
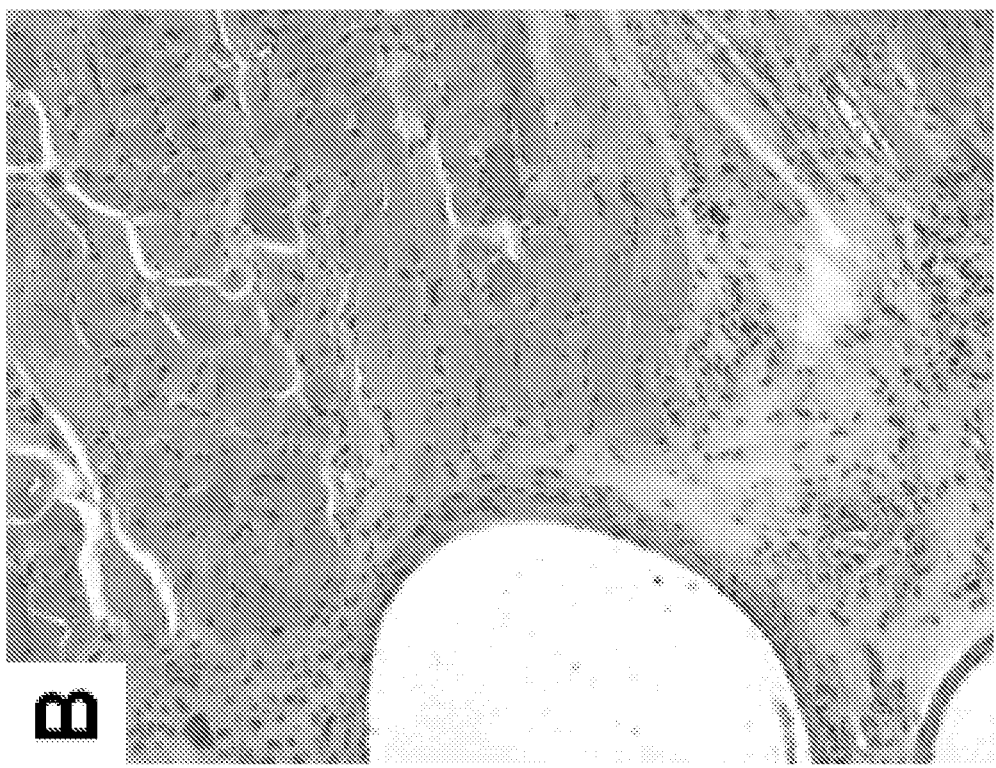
FIG. 10 is micrographs of stained scaffold sections showing the tissue-scaffold interface of a human mandibular molar-shaped scaffold from a dorsum site (test and control groups). Panel A shows angiogenesis and ingrowth of tissues around and between the strands; Panel B shows a higher magnification view showing integration between the scaffold and the encapsulating tissues.
Figure 10:
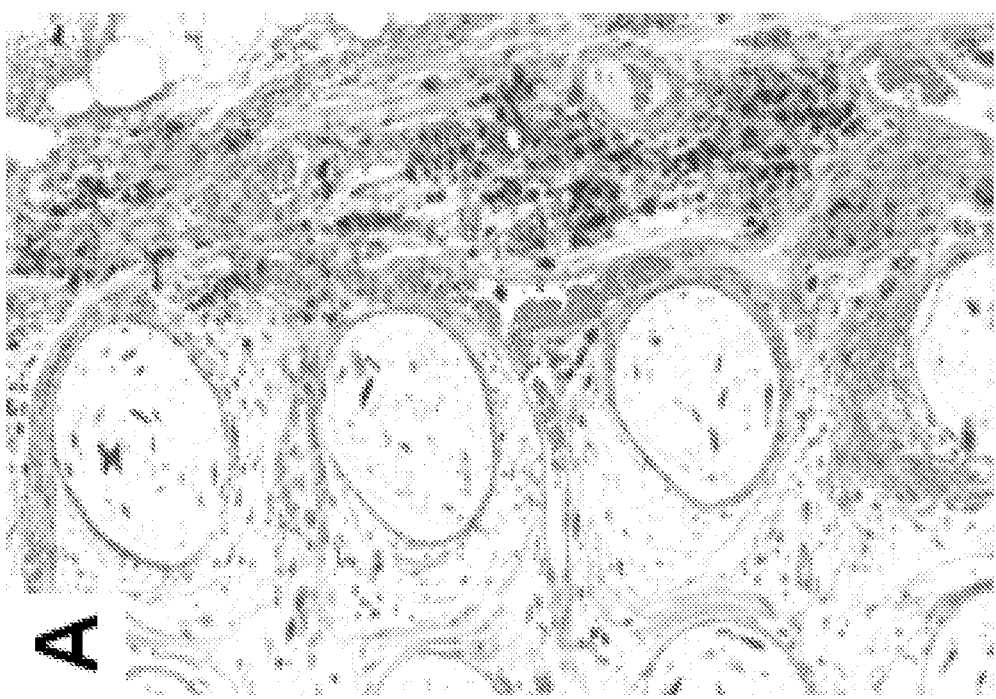

As evident in FIGS. 9 and 10, all scaffolds from both implantation sites of both groups showed that the tissue-scaffold interface regions demonstrated comparably tight tissue-to-scaffold adaptation. It did not appear that there was any noticeable difference between the two groups regardless of the implantation sites. However, the microscopic characteristics of integration appeared to be different between the two implantation sites. With the scaffolds within the extraction sockets, the interface was characterized by noticeable bone-to-scaffold adaptation, possibly with fibrous lining. Some interfaces exhibited bony ingrowth between the strands of the scaffold (FIG. 9A, B). Also, there was a definite evidence of angiogenesis and soft tissue ingrowth at the interface of the scaffold and the socket wall (FIG. 9C). It appeared that the tissue grew around and between the PCL-HA strands (FIG. 9C). Tissue was also along the bony socket walls (FIG. 9C). The dorsum sites showed that the interface had soft tissue ingrowth well into the internal areas of the scaffolds (FIG. 10A, B).

Cell Penetration and Density.

Figure 11:
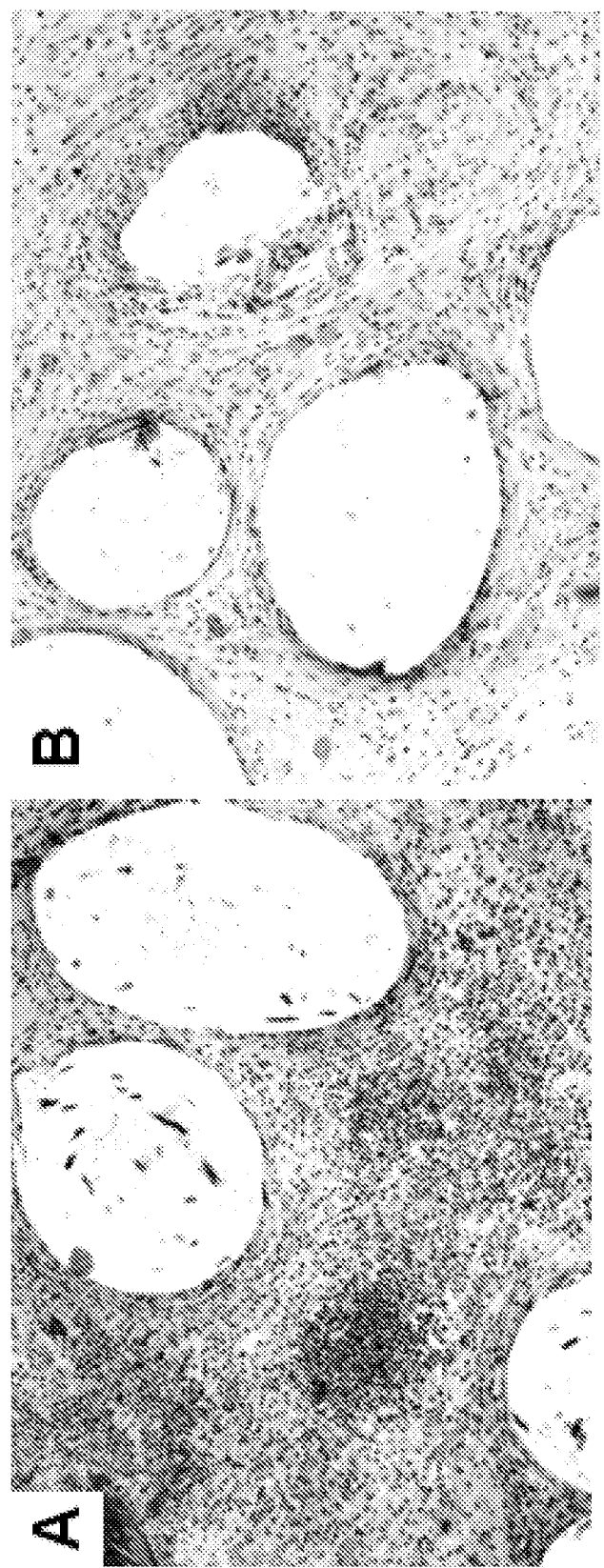
FIG. 11 is micrographs of stained scaffold sections showing representative views of scaffolds from extraction sockets showing differences in cellular density of a test scaffold (Panel A) vs. a control scaffold without growth factors (Panel B).
Figure 12:
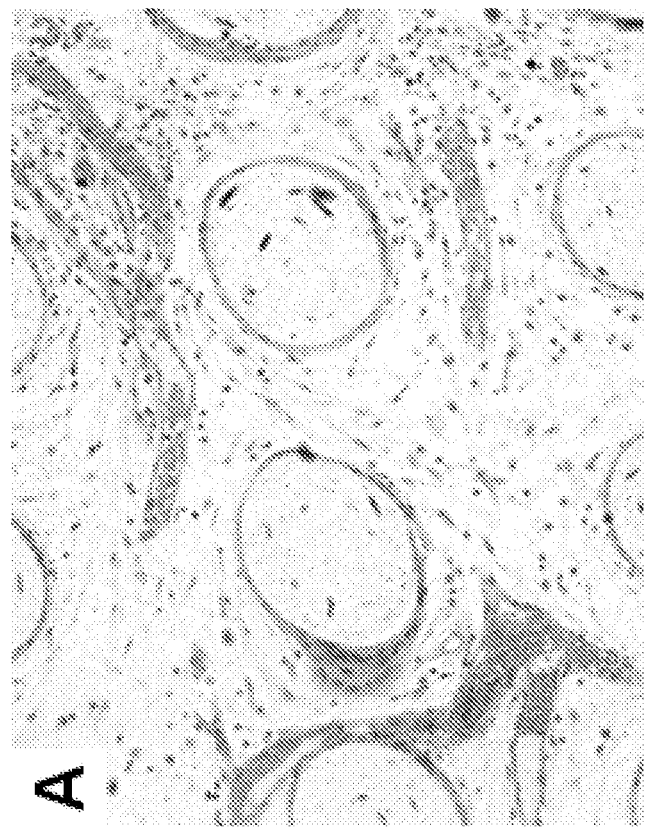
FIG. 12 is micrographs of stained scaffold sections showing representative views of scaffolds from dorsum sites showing differences in cellular density of a test scaffold (Panel A) vs. a control scaffold without growth factors (Panel B).
Figure 12:
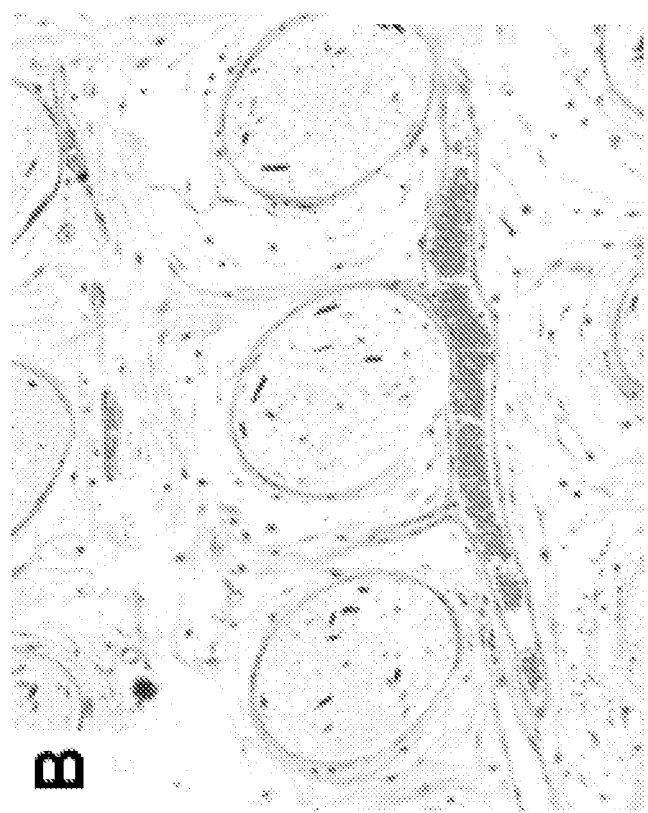
Figure 13:
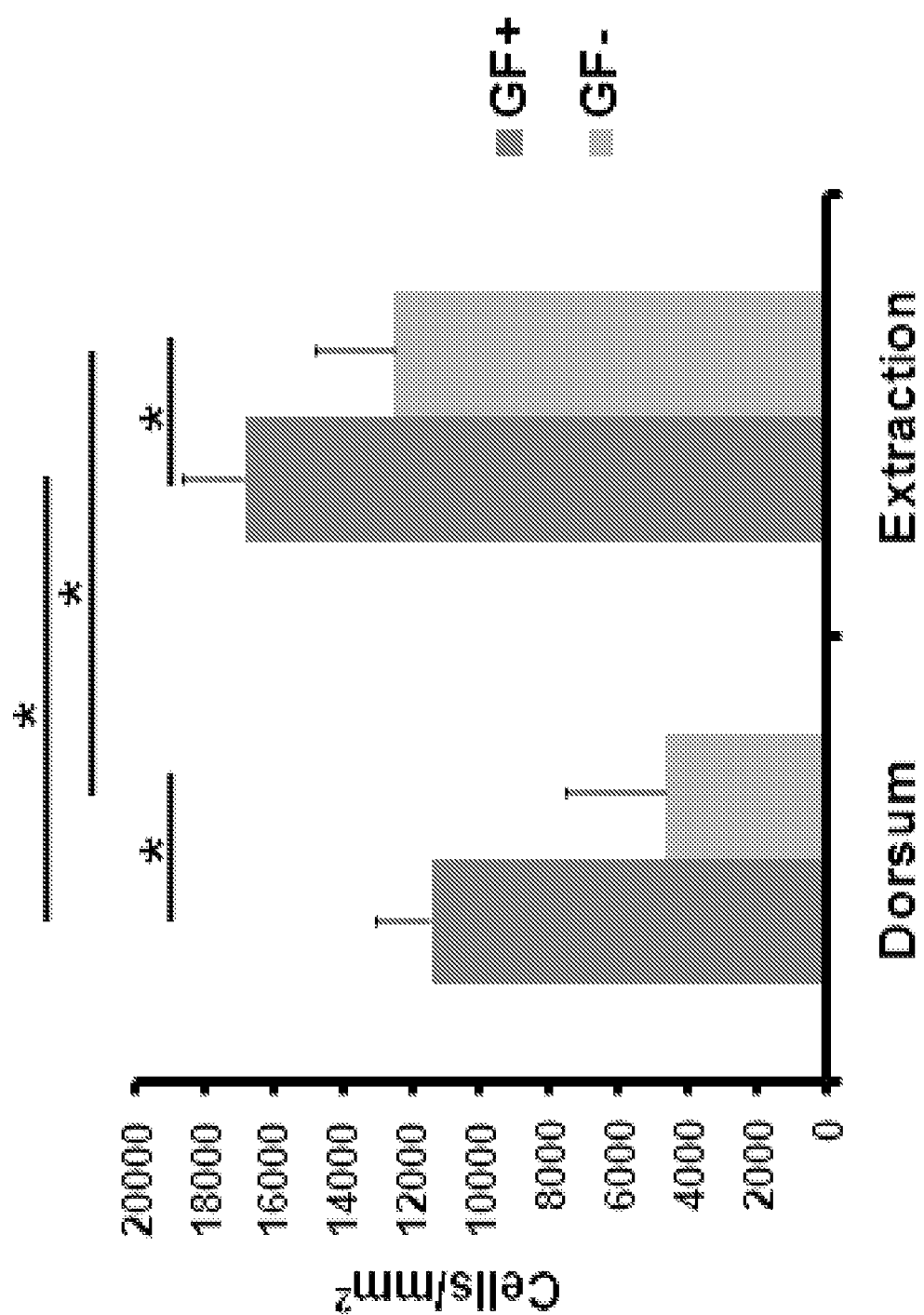
FIG. 13 is a graph showing differences in cellular density between experimental groups and implantation sites. GF+: test; GF−: control. "*": $p<0.05$.

Previous studies utilizing PCL-HA scaffolds have demonstrated cellular penetration and proliferation around strands comprising the PCL-HA scaffold (Heo 2007). As shown in FIGS. 11 and 12, there was a noticeable difference in cell density (cells/$mm^2$) levels between the test and control groups of each implantation site. FIG. 11 depicts representative regions of the scaffolds retrieved from the extraction sockets while FIG. 12 represents the regions from the dorsum site scaffolds, test and control groups, respectively. The cellular density observed from the test group scaffolds was far greater than the one from the control group—p=0.049 and p=0.001, extraction socket site and dorsum site, respectively. The scaffolds retrieved from the extraction sockets had denser cellular populations than the ones from the dorsum sites—p=0.016 and p=0.002, test and control groups, respectively (FIG. 13).

Angiogenesis.

Figure 14:
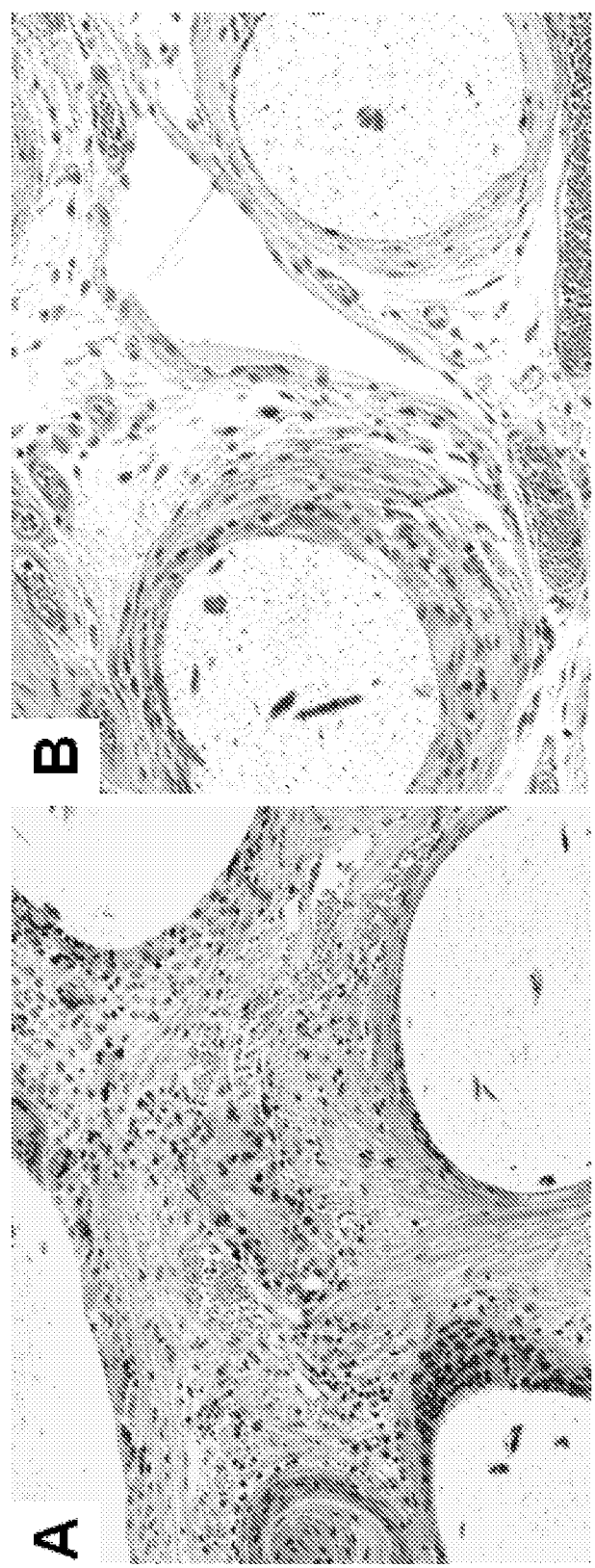
FIG. 14 is micrographs of stained scaffold sections showing representative views of scaffolds from extraction sockets showing differences in vessel density of a test scaffold (Panel A) vs. a control scaffold without growth factors (Panel B).
Figure 15:
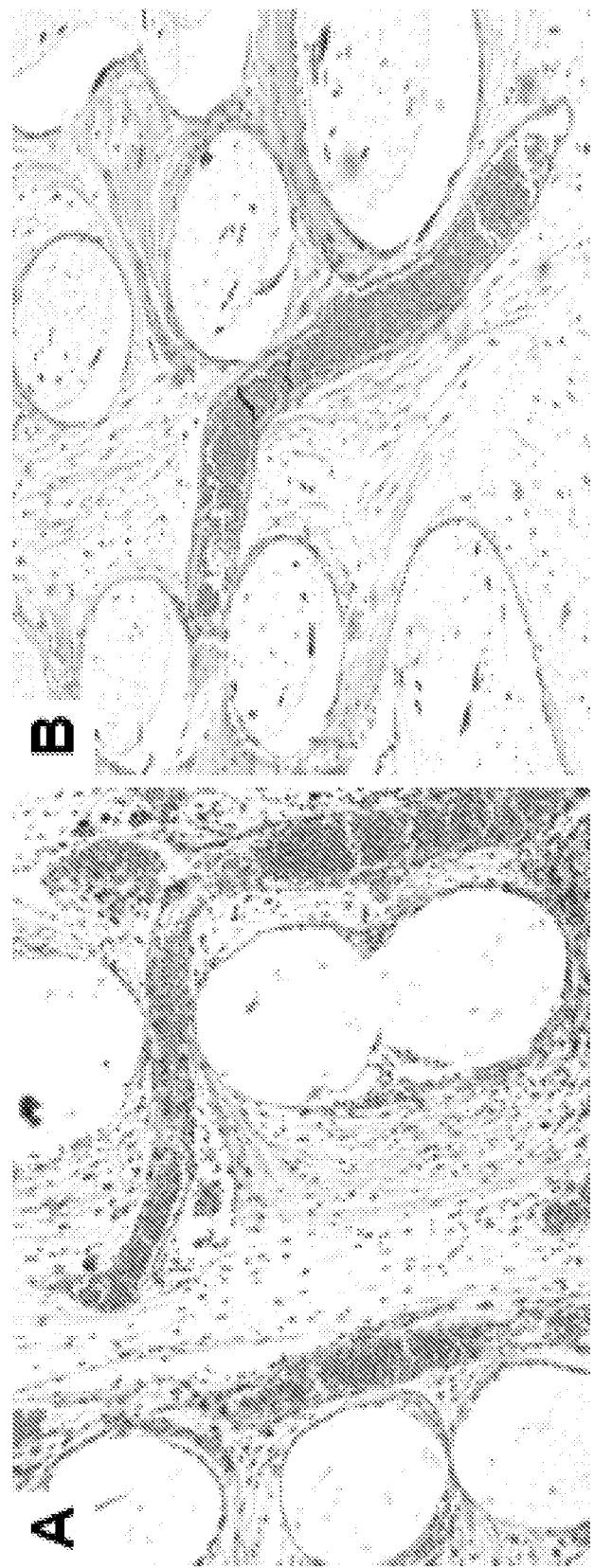
FIG. 15 is micrographs of stained scaffold sections showing representative views of scaffolds from dorsum sites showing differences in cellular density of a test scaffold (Panel A) vs. a control scaffold without growth factors (Panel B).
Figure 16:
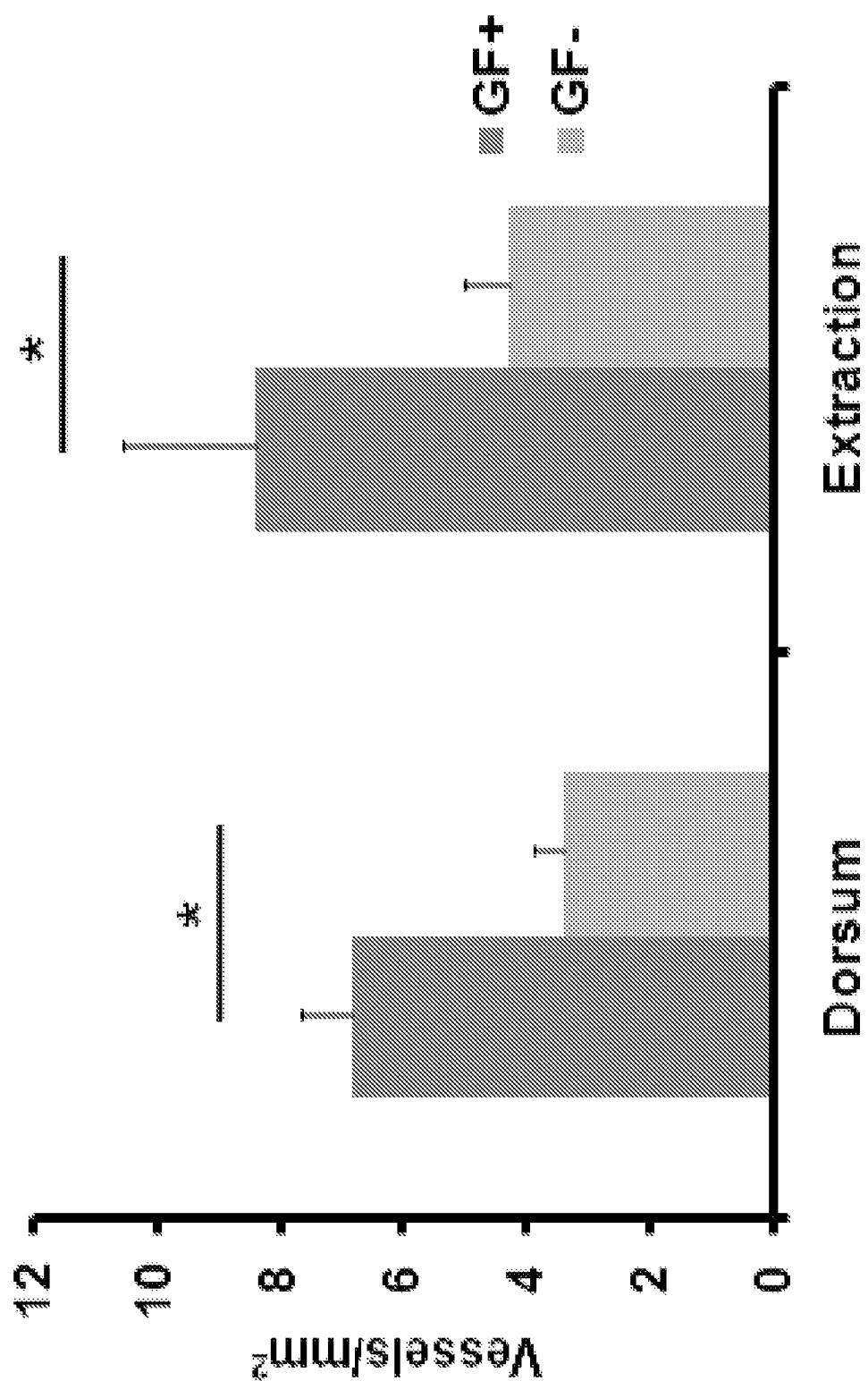
FIG. 16 is a graph showing differences in vessel density between experimental groups and implantation sites. GF+: test; GF−: control. "*": $p<0.05$.

Angiogenesis was evident within all of the harvested scaffolds from the both experimental groups (FIG. 14, 15). In general, there was a greater extent of angiogenesis observed (vessels/mm$^2$) in the test group scaffolds than in the control, regardless of the implantation sites—p=0.011 and p=0.002, extraction socket and dorsum site, respectively (FIG. 16). However, the density observed in the scaffolds from the extraction sockets was seemingly greater overall despite of its statistical insignificance between the groups—p=0.222 and p=0.095, test and control groups, respectively (FIG. 16).

Figure 17:
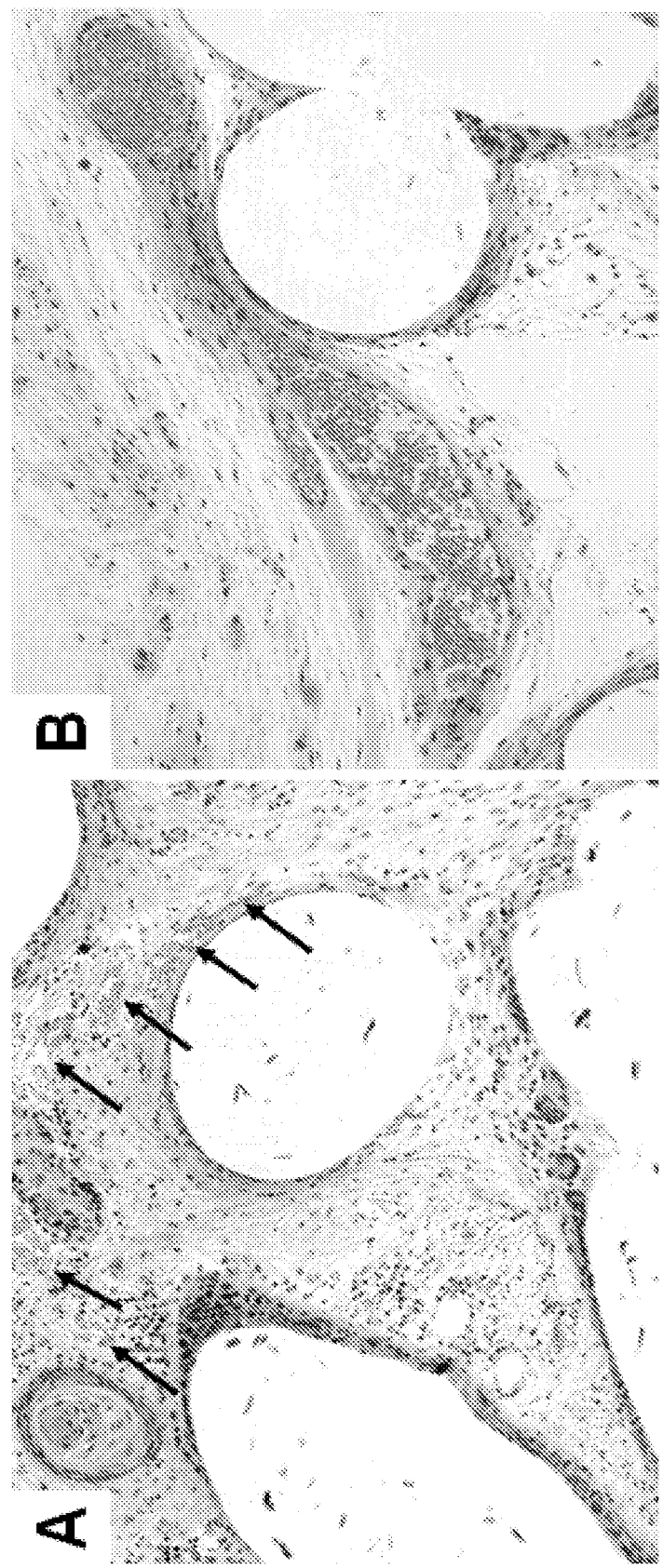
FIG. 17 is micrographs of stained scaffold sections showing representative views showing differences in vessel diameter of scaffolds from an extraction socket (Panel A) vs. a dorsum site (Panel B).
Figure 18:
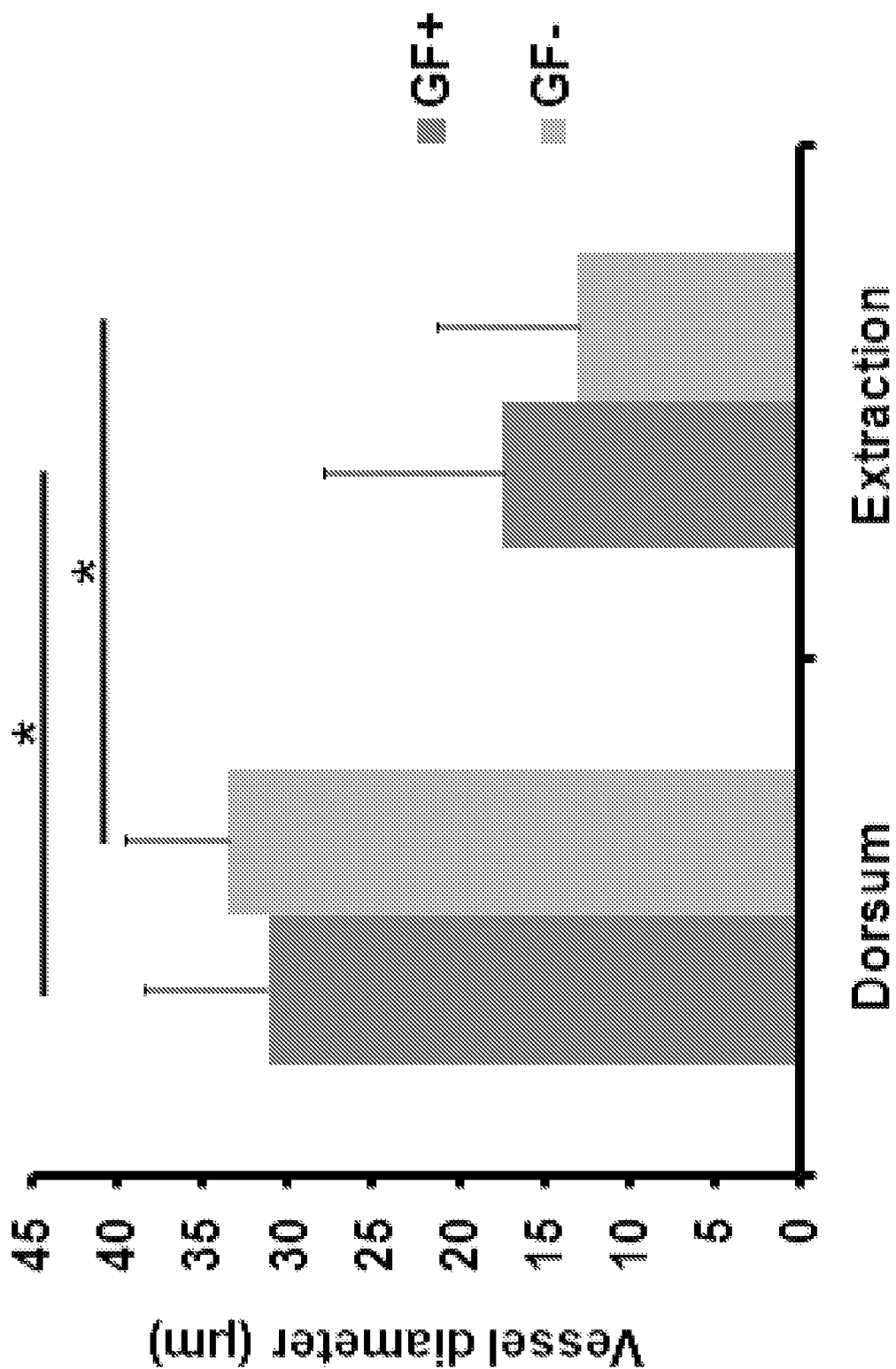
FIG. 18 is a graph showing differences in vessel diameter between experimental groups and implantation sites. GF+: test; GF−: control. "*": $p<0.05$.

The blood vessel diameter (μm) in the dorsum implantation site was greater than in the extraction socket—p=0.028 and p=0.022, test and control groups, respectively (FIG. 18). However, there was no statistical difference between the experimental groups—p=0.426 and p=0.732, extraction socket and dorsum site, respectively (FIG. 18). The representative photos of the slides showed that the vessel diameter appeared much greater in the scaffolds harvested from the dorsum sites than from the extraction sockets (FIG. 17 A, B). As shown FIG. 18, within the dorsum scaffolds there was an apparent greater mean value of vessel diameter within the control groups, although the difference did not reach statistical significance (p=0.732).

Mineralization.

Figure 19:
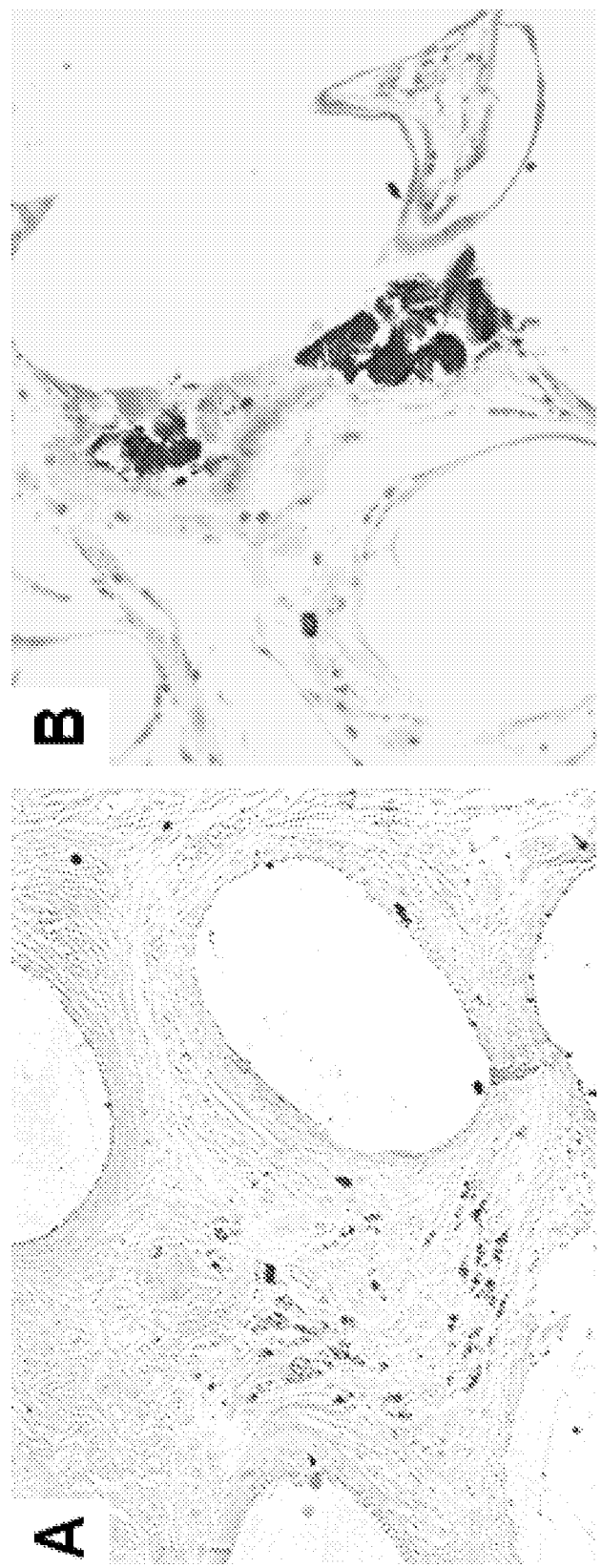
FIG. 19 is micrographs of VK-stained scaffold sections showing representative views of test group scaffolds from the extraction sockets showing mineralization.
Figure 20:
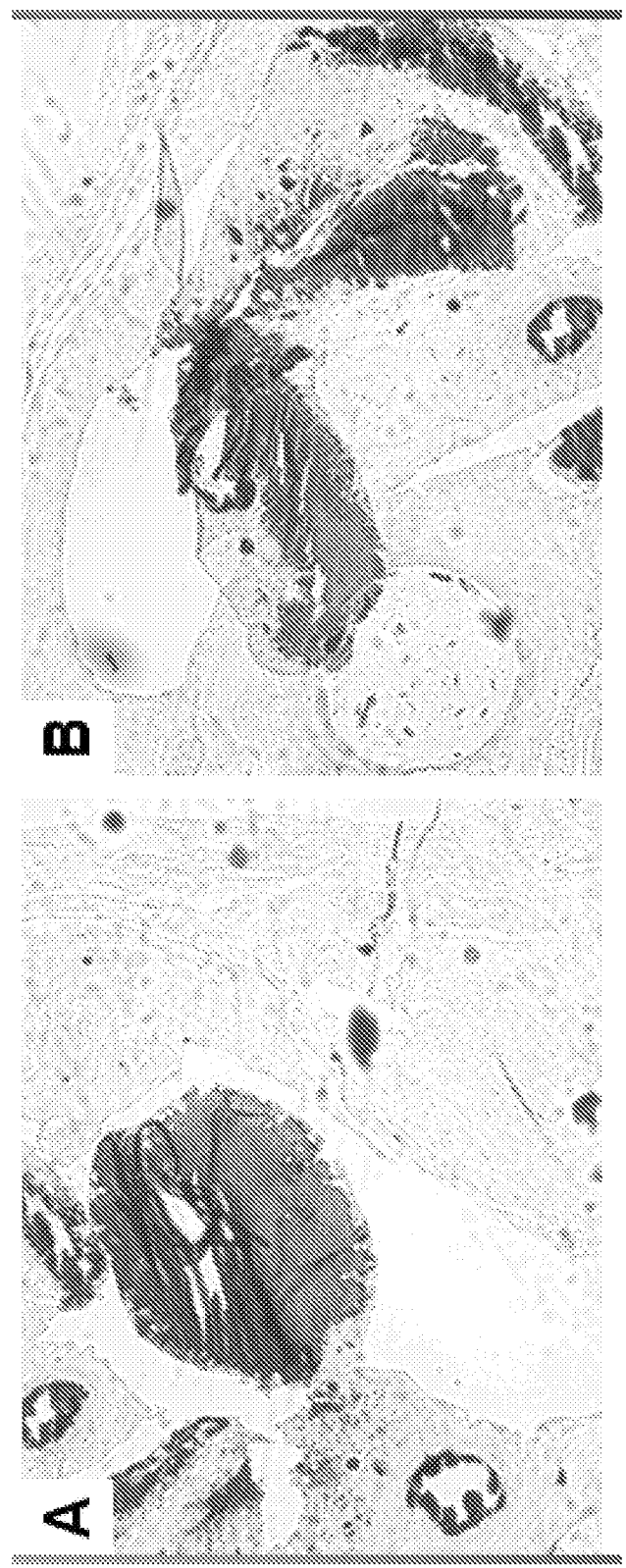
FIG. 20 is micrographs of VK-stained scaffold sections showing representative views of test group scaffolds from dorsum sites showing mineralization.

Mineralization regions were observed in the test group scaffolds only (FIGS. 19, 20). Scaffolds from test group extraction socket and test group dorsum implantation site showed regions of mineralization in the von Kossa (VK) slides. At both implantation sites, mineralization was seen well into the scaffolds, and not at the tissue-to-scaffold interface areas.

Discussion

Cell transplantation is the default strategy of cell based therapies which includes transplantation or injection of culture-expanded or modified tissue progenitors, or fully formed tissue (Mooney 1996). However, therapeutic transplantation of culture-expanded adult cells has several critical barriers, including limited life-span, slow proliferation, and loss of cell phenotype during elongated culture period (Muschler et al. 2004). Accordingly, technological and economic viability of cell delivery approaches, especially for those require substantial cell manipulation ex vivo, has been questioned (Muschler et al. 2004). Recently, there has been a growing interest to regenerate tissues by cell homing, often followed by orchestrating the morphogenesis of the innate cells (Stosich et al. 2007). Cell homing is defined as active recruitment of endogenous cells into predetermined anatomic compartment, and represents an under-studied approach in tissue regeneration (Quesenberry 1998). Schantz, similarly, termed this strategy "cell homing", and defined it as "site-directed homing of native stem cells to induce tissue formation within cytokine-loaded scaffolds" (Schantz 2007). In many adult tissues, stem cells homing and migration are critical for the ongoing replacement of mature cells and regeneration of damaged cells (Laird et al. 2008).

The instant results suggest the internal architecture of interconnected microchannels (200 μm dia.) created by the layer-by-layer deposition of PCL-HA (200 μm dia.) contributed to the intimate tissue-to-scaffold adaptation at the interface areas, followed by the successful homing of host cellular and vascular ingrowth into the large scale (~17 mm) scaffolds. The scaffolds with SDF1 and BMP-7 promoted host cell penetration.

Stromal cell-derived factor-1 (SDF-1), which is secreted by stromal cells in the bone marrow microenvironment, plays an essential role in promoting cell homing by recruitment of progenitor cells that express its cognate receptor, CXC chemokine receptor 4 (CXCR4) (Vandervelde 2005). CXCR4+ positive cells include CD34+ hematopoietic stem cells (HSCs) and mesenchymal stem cells (MSCs) in bone marrow (Brenner et al. 2004; Wynn et al. 2004; Honczarenko et al. 2006; Cheng et al. 2008). Since these cells are essential for vascularization and bone regeneration, we speculate that SDF-1 incorporated in the 3D scaffolds recruited not only local cells but also hematopoetic stem cells and MSCs.

In addition to SDF1, BMP-7 was delivered with the scaffold. Since BMP-7 plays a central role in the transformation of mesenchymal cells into osteoblasts, it is speculated that the ectopic or orthotopic mineralization observed in our cell-free scaffolds was achieved by BMP-7-mediated osteogenic differentiation of stem/progenitor cells, which were recruited by SDF1. However, the results show that there has been little and inconsistent mineralization evident in scaffolds with SDF1 and BMP-7, in both implantation sites. Suboptimal osteogenesis may be because of rapid release of BMP-7, for collagen degrades in vivo quickly.

Interestingly, less mineralized area was observed in the extraction socket implantation site compared to the dorsum, despite of abundance of the blood and the bone marrow cells. This may be because the healing in the extraction socket after removal of a mandibular central incisor possibly was delayed due to the implantation of the scaffold. Extended surgical duration may have also led the paper-thin labial wall more prone to post-operative resorption. The atraumatic extraction procedure of the rat mandibular incisor is known to be extremely technically demanding as the tooth and the surrounding tissues are both extremely fragile. The handling of small rat mandible further complicates the procedure as well.

The histological evaluation confirms in this study that many of the sockets have lost their labial bony plates. This may be due to the extreme thinness of the remaining labial walls. During this process of labial resorption and simultaneous socket remodeling, we raise the possibility that there could have been increased osteoclastic activities. It has been established previously that the healing process of the rat molar extraction sockets is divided into three phases: an early phase (1-5 days) during which organization of the blood clot is completed and the socket is partially covered by epithelium; a bone formation phase (5-20 days); and a bone remodeling phase (20-60 days) when the young bone matures and the alveolar ridge is remodeled (Pietrokovski 1967). Histomorphometric analysis has shown that the edentulous mandible undergoes a significant reduction in size as a result of reduction in both height and width up to 112 days post-extraction (Elsubeihi 2004). Considering the fact that the harvesting procedures took place at the 9$^{th}$ week post-implantation, it might be possible that the remodeling and shrinkage had been actively taking place at the time of the harvest.

In summary, the present findings demonstrated in the in vivo rat model that innate cells could be induced to migrate into the PCL-HA scaffold with simultaneous angiogenesis and vascularization. This study underscored the exaggerated cellular penetration and angiogenesis in the PCL-HA scaffolds impregnated with SDF1 and BMP-7 than in the scaffolds of the control group. The greater extent of cellular ingrowth and angiogenesis was demonstrated in the extraction socket sites compared to the subcutaneous dorsum sites. These findings confirmed the hypothesis that the scaffolds impregnated with SDF1 and BMP-7 in the extraction socket sites would exhibit the greatest proliferative potential. Thus, by demonstrating the rich cellular and vascular density observed in the extraction socket in presence of SDF1 and BMP-7, the potential for the orthotopic regeneration of a tooth using the cell homing techniques has been shown.

Example 2

Regeneration by Chemotaxis; PDGF Induced Recruitment of Alveolar Stem/Progenitor Cells Stem/progenitor cells have been isolated from numerous tissues. Bone marrow is known as one of rich sources of stem/progenitor cells including both hematopoietic stem cells (HSCs) and mesenchymal stem/stromal cells (MSCs). Whereas fibroblast-like MSCs were first discovered in the marrow of long bones in 1970s, marrow of alveolar bone of the face was later found to contain cells analogous to long-bone MSCs, but perhaps with greater potency towards at least osteogenic differentiation. Since alveolar MSCs derive from neural crest/mesenchymal cells, different in embryonic origin from mesoderm-derived appendicular MSCs, the present example explored a novel model for tissue regeneration by chemotaxis of MSCs. Dental pulp is the only soft tissue of a tooth and maintains homeostasis of tooth as an organ. Root canal therapy is one of the most common dental treatments in which viable dental pulp tissue is extirpated and replaced with a bioinert thermoplastic material. Post-root canal teeth are deprived of biological viability and therefore susceptible to re-infection, fracture and trauma. Since dental pulp connects to alveolar bone marrow, it was thought by the inventors that alveolar MSCs can be recruited to regenerate dental pulp tissue.

Small alveolar bone samples were obtained from multiple healthy patients who underwent medically necessary tooth extraction. Mononucleated and adherent cells were slightly culture-expanded. Early-passage MSCs (p3) were first screened and found to express Stro-1, CD105, CD73, CD44 and CD90, but negative to CD34 by immunocytochemistry and flow cytometry. Alveolar MSCs differentiated into osteogenic, adipogenic, chondrogenic and myogenic cells in respective, chemically defined media. Migration of alveolar MSCs was studied in transwell insert system under the influence of multiple cytokines and growth factors.

PDGFββ at 50 ng/ml was most significant in elaborating cell migration at multiple time points. Receptor expression was confirmed.

Together, these findings demonstrate inducing the recruitment of endogenous and/or transplanted stem/progenitor cells towards tissue regeneration.

REFERENCES

Alberektsson T and Johansson C 2001 Osteoinduction, osteoconduction and osseointegration Eur. Spine J. 10 Suppl. 2 S96-101.
Alhadlaq, A. and Mao, J. (2004). "Mesenchymal stem cells: isolation and therapeutics." Stem Cells Dev 13(4): 436-48.
Alhadlaq, A. and Mao, J. (2005). "Tissue-engineered osteochondral constructs in the shape of an articular condyle." J Bone Joint Surg Am 87(5): 936-44.
Alhadlaq, A. and Mao, J. (2004). "Adult stem cell driven genesis of human-shaped articular condyle." Ann Biomed Eng 32(7):911-23.
Astrand P, Carlsson G, Changes in the alveolar process after extractions in the white rat. A histologic and fluorescence microscopic study. Acta Odontol. Scand. 27 1 (1969), pp. 113-127.
Alpaslan C, Irie K, Takahashi K, Ohashi N, Sakai H, Nakajima T, Ozawa H (1996) Long-term evaluation of recombinant human bone morphogenetic protein-2 induced bone formation with a biologic and synthetic delivery system. Br J of Oral Maxillofac Surg 34, 414-418.
Amar S, Han X. The impact of periodontal infection on systemic diseases. Med Sci Monit 2003; 9: RA291-RA299.
Amar S. Implications of cellular and molecular biology advances in periodontal regeneration. Anat Rec 1996: 245: 361-373.
Aoki H, Fujii M, Imamura T, Yagi K, Takehara K, Kato M and Miyazono K 2001 Synergistic effects of different bone morphogenetic protein type I receptors on alkaline phosphatase induction J. Cell. Sci. 114 1483-9.
Aono A, Hazama M, Notoya K, Taketomi S, Yamasaki H, Tsukuda R, Sasaki S and Fujisawa Y 1995 Potent ectopic bone-inducing activity of bone morphogenetic protein-4/7 heterodimer Biochem. Biophys. Res. Commun. 210 670-7.
Arceo N, Saulk J J, Moehring J, Foster R A, Somerman M J. Human periodontal cells initiate mineral like nodules in vitro. J Periodontol 1991: 62: 499-503.
Artico M, Ferrante L, Pastore F S, Ramundo E O, Cantarelli D, Scopelliti D and Iannetti G 2003 Bone autografting of the calvaria and craniofacial skeleton: historical background, surgical results in a series of 15 patients, and review of the literature Surg. Neurol 60 71-9.
Arzate H, Chimal-Monroy J, Hernandez-Iagunas L, Diaz de Leon L. Human cementum protein extract promotes chondrogenesis and mineralization in mesenchymal cells. J Periodontal Res 1996: 31: 144-148.
Arzate H, Olsen S W, Page R C, Goan A M, Narayanan A S. Production of a monoclonal antibody to an attachment protein derived from human cementum. FASEB J 1992: 6: 2990-2996.
Ashman A, LoPinto J, Rosenlicht J. Ridge augmentation for immediate postextraction implants: eight year retrospective study. Pract Periodontics Aesthet Dent 1995: 7: 85-94.
Astrand P, Carlsson G, Changes in the alveolar process after extractions in the white rat. A histologic and fluorescence microscopic study. Acta Odontol. Scand. 27 1 (1969), pp. 113-127.
Atala A, Bauer S B, Soker S, Yoo J J, Retik A B. Tissue engineered autologous bladders for patients needing cystoplasty. Lancet 2006; 367: 1241-6.
Balic A, Mina M. Analysis of developmental potentials of dental pulp in vitro using GFP transgenes. Orthod Craniofac Res 2005: 8: 252-258.
Bartold P M, McCulloch C A, Narayanan A S, Pitaru S. Tissue engineering: a new paradigm for periodontal regeneration based on molecular and cell biology. Periodontol 2000 2000: 24: 253-269.
Bartold P M, Narayanan A S. Molecular and cell biology of healthy and diseased periodontal tissues. Periodontol 2000 2006: 40: 29-49.
Bartold P M, Narayanan A S. Periodontal regeneration. In: Biology of the periodontal connective tissues, Chapter 11. Chicago: Quintessence Publishing, 1998.
Bax B E, Wozney J M, Ashhurst D E (1999) Bone morphogenetic protein-2 increases the rate of callus formation after fracture of the rabbit tibia. Calcif Tissue Int 65, 83-89
Becker W, Becker B E. Periodontal regeneration: a contemporary evaluation. Periodontol 2000 1999: 19: 104-114.
Berkovitz B K B, Holland G R, Moxham B J. Microscopic anatomy of oro-dental tissues. In: Berkovitz B K B, Holland G R, Moxham B J, eds. Color Atlas and Textbook of Oral Anatomy, Histology and Embryology. London: Mosby-Wolfe, 1992; 109-228.

Berry J E, Zhao M, Jin Q, Foster B L, Viswanathan H, Somerman M J. Exploring the origins of cementoblasts and their trigger factors. Connect Tissue Res 2003: 44 (Suppl. 1): 97-102.

Bleul et al. A highly efficacious lymphocyte chemoattractant, stromal cell-derived factor 1 (SDF-1). J. Exp. Med. 184: 1101-1109, 1996.

Bohl K S, Shon J, Rutherford B, Mooney D J. Role of synthetic extracellular matrix in development of engineered dental pulp. Biomater Sci Polymer Ed 1998: 9: 749-764.

Bosshardt D D, Zalzal S, McKee M D, Nanci A. Developmental appearance and distribution of bone sialoprotein and osteopontin in human and rat cementum. Anat Rec 1988: 250: 13-33.

Bosshardt D D. Are cementoblasts a subpopulation of osteoblasts or a unique phenotype? J Dent Res 2005: 84: 390-406.

Boyne P J 2001 Application of bone morphogenetic proteins in the treatment of clinical oral and maxillofacial osseous defects J. Bone Joint Surg. Am. 83A S146-50.

Braut A, Kollar E J, Mina M. Analysis of the odontogenic and osteogenic potentials of dental pulp in vivo using a collal-2.3-GFP transgene. Int J Dev Biol 2003: 47: 281-292.

Brown A, Stock G, Patel A A, Okafor C and Vaccaro A 2006 Osteogenic protein-1: a review of its utility in spinal applications Biodrugs 20 243-51.

Burns J S, Abdallah B M, Guldberg P, Rygaard J, Schroder H D, Kassem M. Tumorigenic heterogeneity in cancer stem cells evolved from long-term cultures of telomeraseimmortalized human mesenchymal stem cells. Cancer Res 2005: 65: 3126-3135.

Carlisle E and Fischgrund J S 2005 Bone morphogenetic proteins for spinal fusion Spine J. 55 240-9.

Carlson N E, Roach R B. Platelet-rich plasma: clinical applications in dentistry. J Am Dent Assoc 2002: 133: 1383-1386.

Castro-Malaspina H, Gay R E, Resnick G, Kapoor N, Meyers P, Chiarieri D, McKenzie S, Broxmeyer H E, Moore M A. Characterization of human bone marrow fibroblast colonyforming cells (CFU-F) and their progeny. Blood 1980: 56: 289-301.

Castro-Malaspina H, Rabellino E M, Yen A, Nachman R L, Moore M A. Human megakaryocyte stimulation of proliferation of bone marrow fibroblasts. Blood 1981: 57: 781-787.

Causa F, Netti P A, Ambrosio G, Ciapetti G, Baldini N, Pagani S, Martini D, Giunti A. Poly-ε-caprolactone/hydroxyapatite composites for bone regeneration: In vitro characterization and human osteoblast response, 2005, Journal of Biomedical Materials Research Part A 76A(1): 151-162.

Chai Y, Jiang X, Ito Y et al. Fate of the mammalian cranial neural crest during tooth and mandibular morphogenesis. Development 2000; 127: 1671-9.

Chai Y, Slavkin H C. Prospects for tooth regeneration in the 21st century: a perspective. Microsc Res Tech 2003; 60: 469-79.

Chen D, Harris M A, Rossini G, Dunstan C R, Dallas S L, Feng J Q, Mundy G R and Harris S E 1997 Bone morphogenetic protein 2 (BMP-2) enhances BMP-3, BMP-4, and bone cell differentiation marker gene expression during the induction of mineralized bone matrix formation in cultures of fetal rat calvarial osteoblasts Calcif. Tissue Int. 60 283-90.

Chen D, Zhao M, Mundy G R (December 2004), Bone morphogenetic proteins, Growth Factors 22 (4): 233-4.

Cheng, H., Jiang, W., Phillips, F. M., Haydon, R. C., Peng, Y., Zhou, L., Luu, H. H., An, N., Breyer, B., Vanichakarn, P., Szatkowski, J. P., Park, J. Y., and He, T. C. Osteogenic activity of the fourteen types of human bone morphogenetic proteins (BMPs). J. Bone. Joint. Surg. Am. 85A, 1544, 2003.

Chim, H., and Schantz, J. T. Human circulating peripheral blood mononuclear cells for calvarial bone tissue engineering. Plast. Reconstr. Surg. 116, 1726, 2006.

Chim, H., Hutmacher, D. W., Chou, A. M., Oliveira, A. L., Reis, R. L., Lim, T. C., and Schantz, J. T. A comparative analysis of scaffold material modifications for load-bearing applications in bone tissue engineering. Int. J. Oral Maxillofac. Surg. 35, 923, 2006.

Chim, H., Ong, J. L., Schantz, J. T., Hutmacher, D. W., and Agrawal, C. M. Efficacy of glow discharge gas plasma treatment as a surface modification process for three-dimensional poly (D/L-lactide) scaffolds. J. Biomed. Mater. Res. A 65, 327, 2003.

Cho M I, Matsuda N, Lin W L, Moshier A, Ramakrishnan P R. In vitro formation of mineralized nodules by periodontal ligament cells from the rat. Calcif Tissue Int 1992: 50: 459-467.

Choi R S, Riegler M, Pothoulakis C, Kim B S, Mooney D, Vacanti M, Vacanti J P. Studies Studies of brush border enzymes, basement membrane components, and electrophysiology of tissue-engineered neointestine, J. of Ped. Surg. 33(7):991-996.

Chopp M, Zhang X H, Li Y, Wang L, Chen J, Lu D, Lu M, Rosenblum M. Spinal cord injury in rat: treatment with bone marrow stromal cell transplantation. Neuroreport 2000: 11: 3001-3005.

Claveau I, Mostefaoui Y and Rouabhia M 2004 Basement membrane protein and matrix metalloproteinase deregulation in engineered human oral mucosa following infection with Candida albicans Matrix Biol. 23 477-86.

Crane, G. M., Ishaug, S. L., and Mikos, A. G. Bone tissue engineering. Nat. Med. 12, 1322, 1995.

D'Errico J A, Ouyang H, Berry J E, MacNeil R L, Strayhorn C, Imperiale M J, Harris N L, Goldberg H, Somerman M J. Immortalized cementoblasts and periodontal ligament cells in culture. Bone 1999: 25: 39-47.

Deans R J, Moseley A B. Mesenchymal stem cells: biology and potential clinical uses. Exp Hematol 2000: 28: 875-884.

Denizot F and Lang R 1986 Rapid colorimetric assay for cell growth and survival. Modifications to the tetrazolium dye procedure giving improved sensitivity and reliability J. Immunol. Methods 89 271-7.

Desbois C and Karsenty G 1995 Osteocalcin cluster: implications for functional studies J. Cell. Biochem. 57 379-83.

De Wynter E A, Emmerson A J, Testa N G. Properties of peripheral blood and cord blood stem cells. Baillieres Best Pract Res Clin Haematol 1999: 12: 1-17.

Dua H S, Azuara-Blanco A. Limbal stem cells of the corneal epithelium. Surv Ophthalmol 2000: 44: 415-425.

Duailibi et al. Long-term case history reports. J Oral Implantol 2000: 26: 276-290.

Duailibi M T, Duailibi S E, Young C S, Bartlett J D, Vacanti J P, Yelick P C. Bioengineered teeth from cultured rat tooth bud cells. J Dent Res 2004: 83: 523-528.

Duailibi S E, Duailibi M T, Vacanti J P, Yelick P C. Prospects for tooth regeneration. Periodontology 2000. 2006; 41:177-87.

Elsubeihi E, Heersche J, Quantitative assessment of post-extraction healing and alveolar ridge remodelling of the mandible in female rats, Archives of Oral Biology 2004, 49:5, p 401-412.

Eppley B L, Pietrzak W S and Blanton M W 2005 Allograft and alloplastic bone substitutes: a review of science and technology for the craniomaxillofacial surgeon. J. Craniofac. Surg. 16 981-9.

Fenton A H, Zarb G A, MacKay HF. Overdenture oversights. Dent Clin North Am 1979: 23: 117-130.

Fibbe, W. E., Pruijt, J. F., van Kooyk, Y., Figdor, C. G., Opdenakker, G., and Wille, R. The role of metalloproteinases and adhesion molecules in interlukin-8-induced stem cell mobilization. Semin. Hematol. 37, 19, 2000.

Fiedler, J., Leucht, F., Waltenberger, J., Dehio, C., and Brenner, R. E. VEGF-A and P1GF-1 stimulate chemotactic migration of human mesenchymal progenitor cells. Biochem. Biophys. Res. Commun. 334, 561, 2005.

Fong H K, Foster B L, Popowics T E, Somerman M J. The crowning achievement: getting to the root of the problem. J Dent Educ 2005; 69: 555-70.

Friedenstein A J, Ivanov-Smolenski A A, Chajlakjan R K, Gorskaya U F, Kuralesova A I, Latzinik N W, Geraswimow U W. Origin of bone marrow stromal mechanocytes in radiochimeras and heterotopic transplants. Exp Hematol 1978: 6: 440-444.

Friedenstein A J. Precursor cells of mechanocytes. Int Rev Cytol 1976: 47: 327-359.

Fuchs J R, Hannouche D, Terada S, Vacanti J P, Fauza D O. Fetal tracheal augmentation with cartilage engineered from bone marrow-derived mesenchymal progenitor cells. J Pediatr Surg 2003: 38: 984-987.

Fujiwara N, Tabata M J, Endoh M, Ishizeki K, Nawa T. Insulin-like growth factor-I stimulates cell proliferation in the outer layer of Hertwig's epithelial root sheath and elongation of the tooth root in mouse molars in vitro. Cell Tissue Res 2005; 320: 69-75.

Gazdag A R, Lane J M, Glaser D. Alternatives to autogenous bone graft: Efficacy and indication. J Am Acad Orthop Surg 1995; 3:1-8.

Gazzerro E, Rydziel S and Canalis E 1999 Skeletal bone morphogenetic proteins suppress the expression of collagenase-3 by rat osteoblasts Endocrinology 140 562-7.

Geiger M, Li R H and Friess W 2003 Collagen sponges for bone regeneration with rhBMP-2 Adv. Drug Deliv. Rev. 55 1613-29.

Giannobile W V, Lee C S, Tomala M P, Tejeda K M, Zhu Z. Platelet-derived growth factor (PDGF) gene delivery for application in periodontal tissue engineering. J Periodontol 2001: 72: 815-823.

Giannobile W V. Periodontal tissue engineering by growth factors. Bone 1996: 19: 23S-37S.

Giannoudis P V and Tzioupis C 2005 Clinical applications of BMP-7: the UK perspective Injury 36 Suppl. 3 S47-50.

Giannoudis P V, Dinopoulos H and Tsiridis E 2005 Bone substitutes: an update Injury 36 Suppl. 3 S20-7.

Gojo S, Gojo N, Takeda Y, Mori T, Abe H, Kyo S, Hata J, Umezawa A. In vivo cardiovasculogenesis by direct injection of isolated adult mesenchymal stem cells. Exp Cell Res 2003: 288: 51-59.

Griffith, L. G., and Naughton, G. Tissue engineering—current challenges and expanding opportunities. Science 295, 1009, 2002.

Groeneveld E H and Burger E H 2000 Bone morphogenetic proteins in human bone regeneration Eur. J. Endocrinol. 142 9-21.

Gronthos S, Chen S, Wang C Y, Robey P G, Shi S. Telomerase accelerates osteogenesis of bone marrow stromal stem cells by upregulation of CBFA1, osterix, and osteocalcin. J Bone Miner Res 2003: 18: 716-722.

Gronthos S, Graves S E, Ohta S, Simmons P J. The STRO-1+ fraction of adult human bone marrow contains the osteogenic precursors. Blood 1994: 84: 4164-4173.

Gronthos S, Mankani M, Brahim J, Gehron Robey P, Shi S. Postnatal human dental pulp stem cells (DPSCs) in vitro and in vivo. Proc Natl Acad Sci USA 2000: 97: 13625-13630.

Gronthos S, Zannettino A C, Graves S E, Ohta S, Hay S J, Simmons P J. Differential cell surface expression of the STRO-1 and alkaline phosphatase antigens on discrete developmental stages in primary cultures of human bone cells. J Bone Miner Res 1999: 14: 47-56.

Gronthos S, Zannettino A C, Hay S J, Shi S, Graves S E, Kaortesidis A, Simmons P J. Molecular and cellular characterization of highly purified stromal stem cells derived from human bone marrow. J Cell Sci 2003: 116: 1827-1835.

Guglielmotti M, Cabrini R, Alveolar wound healing and ridge remodeling after tooth extraction in the rat: a histologic, radiographic, and histometric study. J. Oral Maxillofac. Surg. 43 5 (1985), pp. 359-364.

Harada H, Mitsuyasu T, Toyono T, Toyoshima K. Epithelial stem cells in teeth. Odontology 2002; 90: 1-6.

Harada H, Ohshima H. New perspectives on tooth development and the dental stem cell niche. Arch Histol Cytol 2004: 67: 1-11.

Hawkins N, Garriga G. Asymmetric cell division: from a toz. Genes Dev 1998: 12: 3625-3638.

Heijl L, Heden G, Svärdström G, Östgren A. Enamel matrix derivative (EMDOGAIN) in the treatment of intrabony periodontal pockets. J Clin Periodontol 1997: 24: 705-714.

Heo S J, Kim S E. Fabrication of porous scaffolds for bone tissue engineering using a 3-D robotic system: Comparison with conventional scaffolds fabricated by particulate leaching. Mol Cell Biol 2007; 3:179-180.

Herodin, F., Bourin, P., Mayol, J. F., Lataillade, J. J., and Drouet, M. Short-term injection of antiapoptotic cytokine combinations soon after lethal gamma-irradiation promotes survival. Blood. 101: 2609-2616.

Hirooka H. The biologic concept for the use of enamel matrix protein: true periodontal regeneration. Quintessence Int 1998: 9: 621-630.

Hogan B L 1996 Bone morphogenetic proteins: multifunctional regulators of vertebrate development. Genes Dev. 10 1580-94.

Hollinger J O, Uludag J O and Winn S R 1998 Sustained release emphasizing recombinant human bone morphogenetic protein-2 Adv. Drug Deliv. Rev. 31 303-18.

Honda M J, Sumita Y, Kagami H, Ueda M. Histological and immunohistochemical studies of tissue engineered odontogenesis. Arch Histol Cytol 2005: 68: 89-101.

Horwitz E M, Gorden P L, Koo W K, Marx J C, Neel M D, McNall R Y, et al. Isolated allogenic bone marrow-derived messenchymal cells engraft and stimulate growth in children with osteogenesis imperfect: implications for cell therapy of bone. Proc Natl Acad Sci USA 2002; 99; 8932-7.

Horwitz E M, Prockop D J, Gordon P L, Fitzpatrick L A, Neel M D, McCarville M E, et al. Clinical responses to bone marrow transplantation in children with severe osteogenesis imperfect. Blood 2001; 97:1227-31.

Howell T H, Fiorellini J P, Paquette D W, Offenbacher S, Giannobile W V, Lynch S E, A phase I/II clinical trial to evaluate a combination of recombinant human platelet derived growth factor-BB and recombinant insulin-like growth factor in patients with periodontal disease. J Periodontol 1997: 68: 1186-1193.

Hu B, Nadiri A, Bopp-Kuchler S, Perrin-Schmitt F, Lesot H. Dental epithelial histomorphogenesis in vitro. J Dent Res 2005; 84: 521-5.

Hu B, Nadiri A, Kuchler-Bopp S, Perrin-Schmitt F, Peters H, Lesot H. Tissue engineering of tooth crown, root, and periodontium. Tissue Eng 2006; 12: 2069-75.

Hu B, Unda F, Bopp-Kuchler S et al. Bone marrow cells can give rise to ameloblast-like cells. J Dent Res 2006; 85: 416-21.

Hutmacher D W, Goh J C H, Tech S H. An introduction to biodegradable materials for tissue engineering applications. Ann Acad Med Singapore 2001: 30: 183-191.

Hutmacher D W, Schantz J T, Zein I, Ng K W, Tan K C, Teoh S H Mechanical Properties and Cell Cultural Response of Polycaprolactone Scaffolds Designed and Fabricated via Fused Deposition Modeling. J Biomed Mat Res 2001, 55:203-216.

Huysseune A, Van der heyden C, Sire J Y. Early development of the zebrafish (Danio rerio) pharyngeal dentition (Teleostei, Cyprinidae). Anat Embryol (Berl) 1998: 198: 289-305.

Ikada Y. Tissue engineering research trends at Kyoto University. In: Ikada Y, ed. Tissue Engineering for Therapeutic Use 1. Tokyo: Elsevier, 1998; 1-14.

Isobe M, Yamazaki Y, Mori M, Amagasa T (1999) Bone regeneration produced in rat femur defects by polymer capsules containing recombinant human bone morphogenetic protein-2. J Oral Maxillofac Surg 57, 695-8.

Israel D I, Nove J, Kerns K M, Kaufman R J, Rosen V, Cox K A and Wozney J M 1996 Heterodimeric bone morphogenetic proteins show enhanced activity in vitro and in vivo Growth Factors 13 291-300.

Ivanovski S, Haase H R, Bartold P M. Expression of bone matrix protein mRNAs by primary and cloned cultures of the regenerative phenotype of human periodontal fibroblasts. J Dent Res 2001: 80: 1665-1671.

Jackman W R, Draper B W, Stock D W. Fgf signaling is required for zebrafish tooth development. Dev Biol 2004: 274: 139-157.

Jernvall J, Thesleff I. Reiterative signaling and patterning during mammalian tooth morphogenesis. Mech Dev 2000: 92: 19-29.

Jin Q M, Anusaksathien O, Webb S A, Printz M A, Giannobile W V. Engineering of tooth supporting structures by delivery of PDGF gene therapy vectors. Mol Ther 2004: 9: 519-526.

Jin Q M, Anusaksathien O, Webb S A, Rutherford R B, Giannobile W V. Gene therapy of bone morphogenetic protein for periodontal tissue engineering. J Periodontol 2003: 74: 202-213.

Jin Q M, Zhao M, Webb S A, Berry J E, Somerman M J, Giannobile W V. Cementum engineering with three-dimensional polymer scaffolds. J Biomed Mater Res A 2003: 67: 54-60.

Jorgensen C, Gordeladze J, Noel D. Tissue engineering through autologous mesenchymal stem cells. Current Opin Biotechnol 2004: 15: 406-410.

Kaigler D, Mooney D J. Tissue engineering impact on dentistry. J Dent Educ 2001: 65: 456-462.

Kang Q et al 2004 Characterization of the distinct orthotopic bone-forming activity of 14 BMPs using recombinant adenovirus-mediated gene delivery Gene Ther. 11 1312-20.

Karring T, Nyman S, Gottlow J, Laurell L. Development of the biological concept of guided tissue regeneration animal and human studies. Periodontol 2000 1993: 1: 26-35.

Katchburian E, Arana V. Histologia e Embriologia Oral, $2^{nd}$ edn. Brazil: Editorial Medica Panamericana. Guanabara Koogan, 2005: 151-179.

Kato M, Toyoda H, Namikawa T, Hoshino M, Terai H, Miyamoto S and Takaoka K 2006 Optimized use of a biodegradable polymer as a carrier material for the local delivery of recombinant human bone morphogenetic protein-2 (rh-BMP-2) Biomaterials 27 2035-41.

Kawano S, Saito M, Handa K, Morotomi T, Toyono T, Seta Y, Nakamura N, Uchida T, Toyoshima K, Ohishi M, Harada H. Characterization of dental epithelial progenitor cells derived from cervical-loop epithelium in a rat lower incisor. J Dent Res 2004: 83: 129-133.

Kenley R A, Yim K, Abrams J, Ron E, Turek T, Marden L J and Hollinger J O 1993 Biotechnology and bone graft substitutes Pharm. Res 10 1393-401.

Kim B S. Development of biocompatible synthetic extracellular matrices for tissue engineering. Trends Biotechnol 2001; 16: 224-230.

Kim, C. H., and Broxmeyer, H. E. In vitro behavior of hematopoietic progenitor cells under the influence of chemoattractants: stromal cell-derived factor-1, steel factor, and the bone marrow environment. Blood 91, 100, 1998.

Kim H W, Jonathan C. Hydroxyapatite/PCL composite coatings on hydroxyapatite porous bone scaffold for drug delivery. Biomaterials 2004; 25:1279-1287.

Kim J, Amar S. Periodontal disease and systemic conditions: a bidirectional relationship. Odontology 2006; 94: 10-21.

Kim S S, Utsunomiya H, Koski J A, Wu B M, Cima M J, Sohn J, Mukai K, Griffith L G, Vacanti J P. Survival and function of hepatocytes on a novel three dimensional synthetic biodegradable polymer scaffold with an intrinsic network of channels. Ann Surg 1998: 28: 8-13.

Kim S S, Vacanti J P. The current status of tissue engineering as potential therapy. Semin Pediatr Surg 1999: 8: 119-123.

Koempel J A, Patt B S, O'Grady K, Wozney J, Toriumi D M (1998) The effect of recombinant human bone morphogenetic protein-2 on the integration of porous hydroxyapatite implants with bone. J Biomed Mater Res 41, 359-363.

Koh Y H, Jun I K, Kim H E. Fabrication of poly ε-caprolactone/hydroxyapatite scaffold using rapid direct deposition. Materials Letters 2006: Vol. 60: Issues 9-10: 1184-1187.

Kollet, O., Shivtiel, S., Chen, Y. Q., Suriawinata, J., Thung, S. N., Dabeva, M. D., Kahn, J., Spiegel, A., Dar, A., Samira, S., Goichberg, P., Kalinkovich, A., Arenzana-Seisdedos, F., Nagler, A., Hardan, I., Revel, M., Shafritz, D. A., and Lapidot, T. HGF, SDF-1 and MMP-9 are involved in stress-induced CD34b stem cell recruitment to the liver. J. Clin. Invest. 112, 160, 2003.

Kortesidis, A., Zannettino, A., Isenmann, S., Shi, S., Lapidot, T., and Gronthos, S. Stromal-derived factor-1 promotes the growth, survival, and development of human bone marrow stromal stem cells. Blood 105, 3793, 2005.

Krebsbach P H, Mankani M H, Satomura K, Kuznetsov S A, Robey P G. Repair of craniotomy defects using bone marrow stromal cells. Transplantation 1998: 66: 1272-1278.

Kuboki Y, Saito T, Murata M, Takita H, Mizuno M, Inoue M, Nagai N, Poole A R (1995) Two distinctive BMP-carriers induce zonal chondrogenesis and membranous ossification, respectively; geometrical factors of matrices for cell-differentiation. Connect Tissue Res 32, 219-226

Kucia, M., Reca, R., Miekus, K., Wanzeck, J., Wojakowski, W., Janowska-Wieczorek, A., Ratajczak, J., and Ratajczak, M. Z. Trafficking of normal stem cells and metastasis of cancer stem cells involve similar mechanisms: pivotal role of the SDF-1-CXCR4 axis. Stem Cells 23, 879, 2005.

Laflamme C., Mahmoud R. Effect of BMP-2 and BMP-7 homodimers and a mixture of BMP-2/BMP-7 homodimers on osteoblast adhesion and growth following culture on a collagen scaffold, 2008 Biomed. Mater. 3 015008 (10 pp)

Landers, R., Pfister, A. (2005). Rapid prototyping in medicine. Internal Report, EnvisionTec, Germany.

Landers, R., U. Hubner, et al. (2002). "Rapid prototyping of scaffolds derived from thermoreversible hydrogels and tailored for applications in tissue engineering." Biomaterials 23(23): 4437-47.

Lang H, Schüler N, Nolden R. Attachment formation following replantation of cultured cells into periodontal defects. J Dent Res 1998: 77: 393-405.

Langer R, Vacanti J P. Tissue engineering. Science 1993: 260: 920-926.

Lapidot, T., and Petit, I. Current understanding of stem cell mobilization: the roles of chemokines, proteolytic enzymes, adhesion molecules, cytokines, and stromal cells. Exp. Hematol. 30, 973, 2002.

Laurell L, Gottlow J. Guided tissue regeneration update. Int J Dent 1998: 48: 386-398.

Lekic P, McCulloch C A. Periodontal ligament cell population: the central role of fibroblasts in creating a unique tissue. Anat Rec 1996: 245: 327-341.

Leong K F. Solid freeform fabrication of three-dimensional scaffolds for engineering replacement tissues and organs. Biomaterials 2003; 24:2363-2378.

Lijun K, Yuan G, Guangyuan L. A study on the bioactivity of chitosan/nano-hydroxyapatite composite scaffolds for bone tissue engineering. Eur Polym J 2006; 42:3171-3179.

Lin H. The self-renewing mechanism of stem cells in the germ line. Curr Opin Cell Biol 1998: 10: 687-693.

Lindskog S. Formation of intermediate cementum. I. Early mineralization of aprismatic enamel and intermediate cementum in monkey. J Craniofac Genet Dev Biol 1982: 2: 147-160.

Liu H W, Chen C H, Tsai C L and Hsiue G H 2006 Targeted delivery system for juxtacrine signaling growth factor based on rhBMP-2-mediated carrier-protein conjugation Bone 39 825-36.

Lu, L. and A. G. Mikos (1996). "The importance of new processing techniques in tissue engineering." MRS Bull 21(11): 28-32.

Lu L., Stamatas G., Mikos A, Controlled release of transforming growth factor β1 from biodegradable polymer microparticles, J. of Biomedical Materials Res. Part A., Volume 50 Issue 3, Pages 440-451.

Lynch S E, Genco R J, Marx R E., eds. Tissue engineering. Applications in maxillofacial surgery and periodontics, 1st edn. Carol Stream, Ill.: Quintessence Publishing, 1999.

Lyons K M, Hogan B L and Robertson E J 1995 Colocalization of BMP-7 and BMP-2 RNAs suggests that these factors cooperatively mediate tissue interactions during murine development Mech. Dev. 50 71-83.

Ma P X, Choi J W. (AQ) Biodegradable polymer scaffolds with well defined interconnected spherical pore network. Tissue Eng 2001: 7: 23-33.

Malekzeh R, Hollinger J O, Buck D, Adams D F, McAllister B S. Isolation of human osteoblast-like cells and in vitro amplification for tissue engineering. J Periodontol 1998: 69: 1256-1262.

Mano J F, Sousa R A, Boesel L F. Bioinert biodegradable and injectable polymeric matrix composites for hard tissue replacement: State of the art and recent developments. Compos Sci Technol 2004; 64:789-817.

Manolagas S C 1998 The role of IL-6 type cytokines and their receptors in bone Ann. NY Acad. Sci. 840 194-204.

Marion, N. W. and J. J. Mao (2006). "Mesenchymal stem cells and tissue engineering." Methods Enzymol 420: 339-61.

Mayer H, Scutt A M and Ankenbauer T 1996 Subtle differences in the mitogenic effects of recombinant human bone morphogenetic proteins -2 to -7 on DNA synthesis on primary bone-forming cells and identification of BMP-2/4 receptor Calcif. Tissue Int. 58 249-55.

McCulloch C A, Nemeth E, Lowenberg B, Melcher A H. Paravascular cells in endosteal spaces of alveolar bone contribute to periodontal ligament cell populations. Anat Rec 1987: 219: 233-242.

McCulloch C A. Origins and functions of cells essential for periodontal repair: the role of fibroblasts in tissue homeostasis. Oral Dis 1995: 1: 271-278.

McCulloch C A. Progenitor cell populations in the periodontal ligament of mice. Anat Rec 1985: 211: 258-262.

Meinel L, Fajardo R, Hofmann S, Langer R, Chen J, Snyder B, Vunjak-Novakovic G, Kaplan D. Silk implants for the healing of critical size bone defects. Bone 2005: 37: 688-698.

Melcher A H. Cells of periodontium: their role in the healing of wounds Ann R Coll Surg Engl 1985: 67: 130-131.

Mikos A G, Lyman M D, Freed L E, Langer R. Wetting of poly (L-lactic acid) and poly (DL-lactic-co-glycolic acid) foams for tissue culture. Biomaterials 1993: 15: 55-58.

Mikos A G, Sarakinos G, Leite S M, Vacanti J P, Langer R. Laminated three-dimensional biodegradable foams for use in tissue engineering. Biomaterials 1993: 14: 323-330.

Mikos K F. Preparation and characterization of poly L-lactic acid foam. Polymer 1994; 35:1068-1077.

Miletich I, Sharpe P T. Neural crest contribution to mammalian tooth formation. Birth Defects Res C Embryo Today 2004; 72: 200-12.

Mina M, Braut A. New insight into progenitor/stem cells in dental pulp using Col1a1-GFP transgenes. Cells Tissues Organs 2004: 176: 120-133.

Miura M, Gronthos S, Zhao M, Lu B, Fisher L W, Robey P G, Shi S. SHED: stem cells from human exfoliated deciduous teeth. Proc Natl Acad Sci USA 2003: 100: 5807-5812.

Modino S A, Sharpe P T. Tissue engineering of teeth using adult stem cells. Arch Oral Biol 2005: 50: 255-258.

Moioli E K, Mao J J. Chondrogenesis of mesenchymal stem cells by controlled delivery of transforming growth factor-beta3. Conf Proc IEEE Eng Med Biol Soc. 2006; 1:2647-50

Mooney D J, Mikos A G. Growing new organs. Sci Am 1999: 280: 60-65.

Mooney D J, Powell C, Piana J, Rutherford B. Engineering dental pulp-like tissue in vitro. Biomaterials 1996: 12: 865-868.

Mooney D J. Novel approach to fabrication porous sponge of poly D,L-lactic-co-glycolic acid without the use of organic solvents. Biomaterials 1996; 17:1417-1422.

Moradian-Oldak J. Amelogenins: assembly, processing and control of crystal morphology. Matrix Biol 2001: 20: 293-305.

Moroni L, de Wijn J R, van Blitterswijk C A. 3D fiber-deposited scaffolds for tissue engineering: Influence of pores geometry and architecture on dynamic mechanical properties. Biomaterials 2006; 27:974-985.

Murphy W, Simmons C, Kaigler D, Mooney D, Bone Regeneration via a Mineral Substrate and Induced Angiogenesis, Journal of Dental Research 2004 83: 204-210.

Moss M L. Studies on dentin. I. Mantle dentin. Acta Anat (Basel) 1999: 87: 481-507.

Moule A J, Li H, Bartold P M. Donor variability in the proliferation of human dental pulp fibroblasts. Aust Dent J 1995: 40: 110-114.

Murata M, Inoue M, Arisue M, Kuboki Y, Nagai N (1998) Carrier-dependency of cellular differentiation induced by bone morphogenetic protein in ectopic sites. Int J Oral Maxillofac Surg 27, 391-396.

Murphy W L, Mooney D J. Controlled delivery of inductive proteins, plasmid DNA and cells from tissue engineering matrices. J Periodontal Res 1999: 34: 413-419.

Muschler G F, Nakamoto C, Griffith L G., Engineering principles of clinical cell-based tissue engineering. J Bone Joint Surg Am. 2004 July; 86-A(7):1541-58

Nakagawa T and Tagawa T 2000 Ultrastructural study of direct bone formation induced by BMPs-collagen complex implanted into an ectopic site Oral Dis. 6 172-9.

Nakahara T, Nakamura T, Kobayashi E et al. In situ tissue engineering of periodontal tissues by seeding with periodontal ligament-derived cells. Tissue Eng 2004; 10: 537-44.

Nakahara T, Nakamura T, Kobayashi E et al. Novel approach to regeneration of periodontal tissues based on in situ tissue engineering: effects of controlled release of basic fibroblast growth factor from a sandwich membrane. Tissue Eng 2003; 9: 153-62.

Nakahara T. A review of new developments in tissue engineering therapy for periodontitis. Dent Clin North Am 2006; 50: 265-76, ix-x.

Nakao K, Morita R, Saji Y et al. The development of a bioengineered organ germ method. Nat Meth 2007; 4: 227-30.

Nakashima M, Akamine A. The application of tissue engineering to regeneration of pulp and dentin in endodontics. J. Endod 2005: 31: 711-718.

Nakashima M, Bone morphogenetic proteins in dentin regeneration for potential use in endodontic therapy. Cytokine & Growth Factor Reviews 2005: Vol. 16: Issue 3: 369-376.

Nakashima M, Iohara K, Ishikawa M, Ito M, Tomokiyo A, Tanaka T, Akamine A. Stimulation of reparative dentin formation by ex vivo gene therapy using dental pulp stem cells electrotransfected with growth/differentiation factor 11 (Gdf11). Hum Gene Ther 2004: 15: 1045-1053.

Nakashima The application of bone morphogenic proteins to dental tissue engineering. Nature Biotechnology, Vol 21 Number 9 2003 Pg 1025-1032.

Nakatomi M, Morita I, Eto K, Ota M S. Sonic hedgehog signaling is important in tooth root development. J Dent Res 2006; 85: 427-31.

Nakatsu M, Sainson R, Pérez-del-Pulgar S, Aoto J, Aitkenhead M, Taylor K, Carpenter P, Hughes C, VEGF121 and VEGF165 Regulate Blood Vessel Diameter Through Vascular Endothelial Growth Factor Receptor 2 in an In Vitro Angiogenesis Model, Lab Invest 2003, 83:12, p 1873.

National Institute for Dental and Craniofacial Research. Strategic Plan-2003-2008. J Am Coll Dent 2003: 70: 43-55.

Nebahat D, Dilhan M K, Elvan B. Biocomposites of nanohydroxyapatite with collagen and poly vinyl alcohol. Coll Surf B 2006; 48:42-49.

Ohazama A, Modino S A, Miletich I, Sharpe P T. Stem-cell based tissue engineering of murine teeth. J Dent Res 2004: 83: 518-522.

Onishi T, Ishidou Y, Nagamine T, Yone K, Imamura T, Kato M, Sampath T K, ten Dijke P and Sakou T 1998 Distinct and overlapping patterns of localization of bone morphogenetic protein (BMP) family members and a BMP type II receptor during fracture healing in rats Bone 22 605-12.

Owen M, Friedenstein A J. Stromal stem cells: marrow derived osteogenic precursors. Ciba Found Symp 1988: 136: 42-60.

Owen M E, Cave J, Joyner C J. Clonal analysis in vitro of osteogenic differentiation of marrow CFU-F. J Cell Sci 1987: 87: 731-738.

Payne T L, Skobe Z, Yelick P C. Regulation of tooth development by the novel type I TGFβ family member receptor Alk8. J Dent Res 2001: 80: 1968-1973.

Peled, A., Grabovsky, V., Habler, L., Sandbank, J., Arenzana-Seisdedos, F., Petit, I., Ben-Hur, H., Lapidot, T., and Alon, R. The chemokine SDF-1 stimulates integrin-mediated arrest of CD34 cells on vascular endothelium under shear flow. J. Clin. Invest. 104, 1199, 1999.

Peled, A., Petit, I., Kollet, O., Magid, M., Ponomaryov, T., Byk, T., Nagler, A., Ben-Hur, H., Many, A., Shultz, L., Lider, O., Alon, R., Zipori, D., and Lapidot, T. Dependence of human stem cell engraftment and repopulation of NOD/SCID mice on CXCR4. Science 283, 845, 1999.

Peng Y, Kang Q, Cheng H, Li X, Sun M H, Jiang W, Luu H H, Park J Y, Haydon R C and He T C 2003 Transcriptional characterization of bone morphogenetic proteins (BMPs)-mediated osteogenic signalling J. Cell. Biochem. 90 1149-65.

Perez M A A, Pitaru S, Fregoso A O, Gasga J R, Arzate H. Anticementoblastoma-derived protein antibody partially inhibits mineralization on a cementoblastic cell line. J Struct Biol 2003: 143: 1-13.

Perkins S, Fleischman R A. Stromal cell progeny of murin bone marrow fibroblast colony-forming units are clonal endothelial-like cells that express collagen IV and laminin. Blood 1990: 75: 620-625.

Perrino M A, Yelick P C. Immunolocalization of Alk8 during replacement tooth development in zebrafish. Cells Tissues Organs 2004: 176: 17-27.

Persidis A. Tissue engineering. Nature Biotechnol 1999: 17: 508-510.

Pietrokovski J, Massler M. Ridge remodeling after tooth extraction in rats. J. Dent. Res. 46 1 (1967), pp. 222-231

Pihlstrom B L, Michalowicz B S, Johnson N W. Periodontal diseases. Lancet 2005; 366: 1809-20.

Pitaru S, McCulloch C A G, Naryanan A S. Cellular origins and differentiation control mechanisms during periodontal development and wound healing. J Periodontal Res 1994: 29: 81-94.

Plikus M V, Zeichner-David M, Mayer J A et al. Morphoregulation of teeth: modulating the number, size, shape and differentiation by tuning Bmp activity. Evol Dev 2005; 7: 440-57.

Polson A M. Periodontal regeneration. Chicago: Quintessence Publishing Co., 1994.

Quesenberry P J, Becker P, Stewart F M. Phenotype of the engrafting stem cell in mice. Stem Cells. 1998; 16 Suppl 1:33-5

Qing C, Jian Y, Jianzhong B, Shenguo W. A novel porous cells scaffold made of polylactide-dextran blend by combining phase-separation and particle leaching techniques. Biomaterials 2002; 23:4483-4492.

Quinones C R, Caffesse R G. Current status of guided tissue regeneration. Periodontol 2000 1995: 9: 55-68.

Rahaman M N, Mao J J. Stem cell-based composite tissue constructs for regenerative medicine. Biotechnol Bioeng 2005; 91: 261-84.

Rao M S. Multipotent and restricted precursors in the central nervous system. Anat Rec 1999: 257: 137-148.

Rezwan K, Chen Q, Blaker J. Biodegradable and bio active porous polymer/inorganic composite scaffolds for bone tissue engineering. Biomaterials 2006; 27:3413-3431.

Rich J, Jaakkola T, Tirri T. In vitro evaluation of poly e-caprolactone-co-DL-lactide/bioactive glass composites. Biomaterials 2002; 23:2143-2150.

Ripamonti U, Reddi A H. Tissue engineering, morphogenesis, and regeneration of the periodontal tissues by bone morphogenetic proteins. Crit Rev Oral Biol Med 1997: 8: 154-163.

Rouabhia M, Ross G, Page N and Chakir J 2002 Interleukin-18 and gamma interferon production by oral epithelial cells in response to exposure to Candida albicans or lipopolysaccharide stimulation Infect. Immun. 70 7073-80.

Rubio D, Garcia-Castro J, Martin M C, de la Fuente R, Cigudosa J C, Lloyd A C, Bernad A. Spontaneous human adult stem cell transformation. Cancer Res 2005: 65: 3035-3039 [Erratum in Cancer Res 2005: 65: 4969].

Rutherford R B, Ryan M E, Kennedy J E, Tucker M M, Charette M F. Platelet-derived growth factor and dexamethasone combined with a collagen matrix induce regeneration of the periodontium in monkeys. J Clin Periodontol 1993: 20: 537-544.

Sainio K, Raatikainen-Ahokas A. Mesonephric kidney—stem cell factory? Int J Dev Biol 1999: 43: 435-439.

Saito N and Takaoka K 2003 New synthetic biodegradable polymers as BMP carriers for bone tissue engineering Biomaterials 24 2287-93.

Saito N, Okada T, Toba S, Miyamoto S, Takaoka K (1999) New synthetic absorbable polymers as BMP carriers: plastic properties of poly-D,L-lactic acidpolyethylene glycol block copolymers. J Biomed Mater Res 47, 104-110.

Sampath T K, Coughlin J E, Whetstone R M, Banach D, Corbett C, Ridge R J, Ozkaynak E, Oppermann H and Rueger D C 1990 Bovine osteogenic protein is composed of dimers of OP-1 and BMP-2A, two members of the transforming growth factor-beta superfamily J. Biol. Chem. 265 13198-205.

Santos E, Badin S, Shenker B, Shapiro I, Ducheye P, Si—Ca—P xerogels and bone morphogenetic protein act synergistically on rat stromal marrow cell differentiation in vitro. J Biomed Mater Res 41, 87-94.

Schantz J, Chim H, Whiteman M. Cell Homing in Tissue Engineering: SDF-1 Mediates Site-Directed Homing of Mesenchymal Stem Cells within Three-Dimensional Polycaprolactone Scaffolds, Tissue Engineering 2007: Vol. 13: 11: 2615-2624.

Schantz, J. T., and Ng, K. W. A Manual for Primary Human Cell Culture. New Jersey: World Scientific, 2004.

Schantz, J. T., Hutmacher, D. W., Chim, H., Ng, K. W., Lim, T. C., and Teoh, S. H. Induction of ectopic bone formation by using human periosteal cells in combination with a novel scaffold technology. Cell Transplant. 11, 125, 2002.

Scott, L. J., Clarke, N. W., George, N. J., Shanks, J. H., Testa, N. G., and Lang, S. H. Interactions of human prostatic epithelial cells with bone marrow endothelium: binding and invasion. Br. J. Cancer 84, 1417, 2001.

Seale P, Rudnicki M A. A new look at the origin, function, and stem-cell" status of muscle satellite cells. Dev Biol 2000: 218: 115-124.

Seo B M, Miura M, Gronthos S et al. Investigation of multipotent postnatal stem cells from human periodontal ligament. Lancet 2004: 364: 149-55.

Sharpe P T, Young C S. Test-tube teeth. Sci Am 2005; 293: 34-41.

Shi S, Bartold P M, Miura M, Seo B M, Robey P G, Gronthos S (2005) The efficacy of mesenchymal stem cells to regenerate and repair dental structures. Orthod Craniofac Res 8: 191-199.

Shi S, Gronthos S, Chen S, Reddi A, Counter C M, Robey P G, Wang C Y. Bone formation by human postnatal bone marrow stromal stem cells is enhanced by telomerase expression. Nat Biotechnol. 2002 June; 20(6):587-91.

Shi S, Gronthos S. Perivascular niche of postnatal mesenchymal stem cells in human bone marrow and dental pulp. J Bone Miner Res 2003: 18: 696-704.

Shi S, Robey P G, Gronthos S. Comparison of human dental pulp and bone marrow stromal stem cells by cDNA microarray analysis. Bone 2001: 29: 532-539.

Shieh S J, Vacanti J P. State-of-the-art tissue engineering: from tissue engineering to organ building. Surgery 2005 137: 1-7.

Shimizu Y. Tissue engineering for soft tissues. In: Ikada Y, ed. Tissue Engineering for Therapeutic Use 2. Tokyo: Elsevier, 1998; 119-22.

Shin H, Jo S, Mikos A G. Biomimetic materials for tissue engineering. Biomaterials 2003; 24:4353-4364.

Simmons P J, Torok-Storb B. Identification of stromal cell precursors in human bone marrow by a novel monoclonal antibody, STRO-1. Blood 1991: 78: 55-62.

Simonsen J L, Rosada C, Serakinci N, Justesen J, Stenderup K, Rattan S I, Jensen T G, Kassem M. Telomerase expression extends the proliferative life-span and maintains the osteogenic potential of human bone marrow stromal cells. Nat Biotechnol 2002: 20: 592-596.

Sittinger M, Bujia J, Rotter N, Reitzel D, Minuth W W, Burmester G R. Tissue engineering and autologous transplant formation: practical approaches with resorbable biomaterials and new cell culture techniques. Biomaterials 1996: 17: 237-242.

Slavkin H C, Bringas P Jr, Bessem C, Santos V, Nakamura M, Hsu M Y, Snead M L, Zeichner-David M, Fincham A G. Hertwig's epithelial root sheath differentiation and initial cementum and bone formation during long-term organ culture of mouse mandibular first molars using serumless, chemically defined medium. J Periodontal Res 1989: 24: 28-40.

Smith A J, Murray P E, Sloan A J, Matthews J B, Zhao S. Transdentinal stimulation of tertiary dentinogenesis. Adv Dent Res 2001: 15: 51-54.

Smith A J. Tooth tissue engineering and regeneration—a translational vision! J Dent Res 2004: 83: 517.

Sodek J. A new approach to assessing collagen turnover by using a microassay. A highly efficient and rapid turnover of collagen in rat periodontal tissues. Biochem J 1976: 160:

Sonoyama W, Liu Y, Fang D, Yamaza T, Seo B M, Zhang C, Liu H, Gronthos S, Wang C, Shi S, Wang S, Mesenchymal Stem Cell-Mediated Functional Tooth Regeneration in Swine, PLoS ONE. 2006; 1(1): e79.

Steele-Perkins G, Butz K G, Lyons G E et al. Essential role for NFI-C/CTF transcription-replication factor in tooth root development. Mol Cell Biol 2003; 23: 1075-84.

Sternlicht M D and Werb Z 2001 How matrix metalloproteinases regulate cell behavior Annu Rev. Cell Dev. Biol. 17 463-516.

Stock U A, Vacanti J P. Tissue engineering: current state and prospects Annu Rev Med 2001: 52: 143-151.

Stosich M S, Bastian B, Marion N W, Clark P A, Reilly G, Mao J J, Vascularized adipose tissue grafts from human mesenchymal stem cells with bioactive cues and microchannel conduits. Tissue Eng. 2007 December; 13(12): 2881-90

Sumikawa D A, Marshall G W, Gee L, Marshall S J. Microstructure of primary tooth dentin. Pediatr Dent 1999: 21: 439-444.

Susan Liao, Kazuchika T. Human neutrophils reaction to the biodegraded nano-hydroxyapatite/collagen and nano-hydroxyapatite/collagen/poly L-lactic acid composite. J Biomed Mater Res 2006; 76A:820-825.

Suzuki Y, Tanihara M, Suzuki K, Saitou A, Sufan W and Nishimura Y 2000 Alginate hydrogel linked with synthetic oligopeptide derived from BMP-2 allows ectopic osteoinduction in vivo J. Biomed. Mater. Res. 50 405-9.

Sweeney T M, Opperman L A, Persing J A, Ogle R C (1995) Repair of critical size rat calvarial defects using extracellular matrix protein gels. J Neurosurg 83, 710-715.

Sylvain D, Eduardo S, Antoni P T. Freeze casting of hydroxyapatite scaffolds for bone tissue engineering. Biomaterials 2006; 27:5480-5489.

Taba M Jr, Jin Q, Sugai J V, Giannobile W V. Current concepts in periodontal bioengineering. Orthod Craniofac Res 2005: 8: 292-302.

Tabata Y. Significance of release technology in tissue engineering. Drug Discov Today 2005; 10: 1639-46.

Taguchi Y, Yamamoto M, Yamate T, Lin S C, Mocharla H, DeTogni P, Nakayama N, Boyce B F, Abe E and Manolagas S C 1998 Interleukin-6-type cytokines stimulate mesenchymal progenitor differentiation toward the osteoblastic lineage Proc. Assoc. Am. Physicians 110 559-74.

Tan K H, Chua C K, Leong K F. Scaffold development using selective laser sintering of polyetheretherketone-hydroxyapatite biocomposite blends. Biomaterials 2003; 24:3115-3123.

Tardif F, Ross G and Rouabhia M 2004 Gingival and dermal fibroblasts produce interleukin-1 beta converting enzyme and interleukin-1 beta but not interleukin-18 even after stimulation with lipopolysaccharide J. Cell. Physiol. 198 125-32.

Thesleff I, Aberg T. Molecular regulation of tooth development. Bone 1999: 25: 123-125.

Thesleff I, Keranen S, Jernvall J. Enamel knots as signaling centers linking tooth morphogenesis and odontoblast differentiation. Adv Dent Res 2001: 15: 14-18.

Thesleff I, Sharpe P. Signalling networks regulating dental development. Mech Dev 1997; 67: 111-23.

Thesleff I, Vaahtokari A, Kettunen P, Aberg T. Epithelialmesenchymal signaling during tooth development. Connect Tissue Res 1995: 32: 9-15.

Thesleff I. Epithelial-mesenchymal signalling regulating tooth morphogenesis. J Cell Sci 2003; 116: 1647-8.

Thesleff I. The genetic basis of tooth development and dental defects. Am J Med Genet A 2006; 140: 2530-5.

Thies R S, Bauduy M, Ashton B A, Kurtzberg L, Wozney J M and Rosen V 1992 Recombinant human bone morphogenetic protein-2 induces osteoblastic differentiation in W-20-17 stromal cells Endocrinology 130 1318-24.

Toma C, Pittenger M F, Cahill K S, Byrne B J, Kessler P D. Human mesenchymal stem cells differentiate to a cardiomyocyte phenotype in the adult murine heart. Circulation 2002: 105: 93-98.

Tsuji K, Ito Y and Noda M 1998 Expression of the PEBP2alphaA/AML3/CBFA1 gene is regulated by BMP4/7 heterodimer and its overexpression suppresses type I collagen and osteocalcin gene expression in osteoblastic and nonosteoblastic mesenchymal cells Bone 22 87-92.

Tucker A, Sharpe P. The cutting-edge of mammalian development: how the embryo makes teeth. Nat Rev Genet 2004; 5: 499-508.

Tummers M, Thesleff I (2003) Root or crown: a developmental choice orchestrated by the differential regulation of the epithelial stem cell niche in the tooth of two rodent species. Development 130: 1049-1057.

US Department of Health and Human Services. Oral health in America: a report of the surgeon general. Rockville, Md.: US Department of Health and Human Services, NIDCR, NIH, 2000.

Vacanti M P, Leonard J L, Dore B, Bonassar L J, Cao Y, Stachelek S J, Vacanti J P, O'Connell F, Yu C S, Farwell A P, Vacanti C A. Tissue-engineered spinal cord. Transplant Proc 2001: 33: 592-598.

Varghese S and Canalis E 1997 Regulation of collagenase-3 by bone morphogenetic protein-2 in bone cell cultures Endocrinology 138 1035-40.

Van Dijk L J, Schakenraad J M, van der Voort H M, Busscher H J. Cell seeding of periodontal ligament fibroblasts. A pilot study. J Clin Periodontol 1991: 18: 196-199.

Van der Heyden C, Allizard F, Sire J Y, Huysseune A. Tooth development in vitro in two teleost fish, the cichlid *Hemichromis bimaculatus* and the cyprinid *Danio rerio*. Cell Tissue Res 2005: 321: 375-389.

Van der Heyden C, Huysseune A. Dynamics of tooth formation and replacement in the zebrafish (*Danio rerio*) (Teleostei, Cyprinidae). Dev Dyn 2005: 219: 486-496.

Van der Heyden C, Wautier K, Huysseune A. Tooth succession in the zebrafish (*Danio rerio*). Arch Oral Biol 2001: 46: 1051-1058.

Vandervelde S, van Luyn M J, Tio R A, Harmsen M C Signaling factors in stem cell-mediated repair of infarcted myocardium. J Mol Cell Cardiol. 2005 August; 39(2):363-76.

Vavidovitch Z. Bone metabolism associated with tooth eruption and orthodontic tooth movement. J Periodontol 1979: 50 (4 Spec No): 22-29.

Viljanen V V, Lindholm T C, Gao T J, Lindholm T S (1997) Low dosage of native allogeneic bone morphogenetic protein in repair of sheep calvarial defects. Int J Oral Maxillofac Surg 26, 389-393.

Wei Jie, Li Yubao. A study on nano-composite of hydroxyapatite and polyamide. J Mater Sci 2003; 38:3303-3306.

Woodfield, T. B., C. A. Van Blitterswijk, et al. (2005). "Polymer scaffolds fabricated with pore-size gradients as a model for studying the zonal organization within tissue-engineered cartilage constructs." Tissue Eng 11(9-10): 1297-311.

Woodfield, T. B., J. Malda, et al. (2004). "Design of porous scaffolds for cartilage tissue engineering using a three-dimensional fiber-deposition technique." Biomaterials 25(18): 4149-61.

Wozney J M, Rosen V, Byrne M, Celeste A J, Moutsatsos I, Wang E A. Growth factors influencing bone development. J Cell Sci Suppl. 1990; 13:149-156.

Wynn, R. F., Hart, C. A., Corradi-Perini, C., O'Neill, L., Evans, C. A., Wraith, E., Fairbairn, L. J., and Bellantuono, I. A small proportion of mesenchymal stem cells strongly expresses functionality active CXCR4 receptor capable of promoting migration to bone marrow. Blood 104, 2643, 2004.

Xiao Y, Qian H, Young W G, Bartold P M. Tissue engineering for bone regeneration using differentiated alveolar bone cells in collagen scaffolds. Tissue Eng 2003: 9: 1167-1177.

Yamada S, Murakami S, Matoba R, Ozawa Y, Yokokoji T, Nakahira Y, Ikezawa K, Takayama S, Matsubara K, Okada H. Expression profile of active genes in human periodontal ligament and isolation of PLAP-1, a novel SLRP family gene. Gene 2001: 275: 279-286.

Yamashiro T, Tummers M, Thesleff I. Expression of bone morphogenetic proteins and Msx genes during root formation. J Dent Res 2003; 82: 172-6.

Yelick P C, Schilling T F. Molecular dissection of craniofacial development using zebrafish. Crit Rev Oral Biol Med 2002: 13: 308-322.

Yelick P C, Vacanti J P. Bioengineered teeth from tooth bud cells. Dent Clin North Am 2006; 50: 191-203, viii.

Yeong W-Y, Chua C-K. Rapid prototyping in tissue engineering: Challenges and potential. Trends Biotechnol 2004; 22:643-652.

Young C S, Abukawa H, Asrican R et al. Tissue-engineered hybrid tooth and bone. Tissue Eng 2005; 11: 1599-610.

Young C S, Abukawa H, Asrican R, Ravens M, Troulis M J, Kaban L B, Vacanti J P, Yelick P C (2005) Tissue-engineered hybrid tooth and bone. Tissue Eng 11: 1599-1610.

Young C S, Kim S-W, Taylor R, Vacanti J P, Bartlett J D, Yelick P C. Developmental analysis and three-dimensional computer modeling of tooth crowns grown on biodegradable polymer scaffolds. Arch Oral Biol 2005: 50: 259-265.

Young C S, Terada S, Vacanti J P, Honda M, Bartlett J D, Yelick P C. Tissue engineering of complex tooth structure on biodegradable polymer scaffolds. J Dent Res 2002: 81: 695-700.

Zhang W, Walboomers X F, Wolke J G, Bian Z, Fan M W, Jansen J A. Differentiation ability of rat postnatal dental pulp cells in vitro. Tissue Eng 2005: 11: 357-368.

Zhao J, Guo L Y, Yang X B, Weng J. Preparation of bioactive porous HA/PCL composite scaffolds. Applied Surface Science 2008: Vol. 255: Issue 5: Part 2: 2942-2946.

Zhao L R, Duan W M, Reyes M, Keene C D, Verfaillie C M, Low W C. Human bone marrow stem cells exhibit neural phenotypes and ameliorate neurological deficits after grafting into the ischemic brain of rats. Exp Neurol 2002: 174: 11-20.

Zhao M, Jin Q, Berry J E, Nociti F H Jr, Giannobile W V, Somerman M J. Cementoblast delivery for periodontal tissue engineering. J Periodontol 2004: 75: 154-161.

Zhu W, Rawlins B A, Boachie-Adjei O, Myers E R, Arimizu J, Choi E, Lieberman J R, Crystal R G and Hidaka C 2004 Combined bone morphogenetic protein-2 and -7 gene transfer enhances osteoblastic differentiation and spine fusion in a rodent model J. Bone Miner. Res. 19 2021-32.

In view of the above, it will be seen that the several advantages of the invention are achieved and other advantages attained.

The invention claimed is:

1. An acellular mammalian tooth-shaped scaffold comprising:
 a matrix material;
 a composition comprising stromal cell-derived factor-1 (SDF-1) and a bone morphogenetic protein-7 (BMP-7);
 microchannels having a diameter of about 200 μm; and
 a nonporous cap;
 wherein
  the composition is chemotactic, osteogenic, dentinogenic, amelogenic, or cementogenic;
  the composition induces migration of progenitor cells when the scaffold is in contact with a dental tissue of a mammalian subject;
  the composition is distributed throughout the tooth-shaped scaffold; and
  the scaffold does not comprise a living cell prior to implantation;
  BMP-7 is imbedded in the microchannels in a collagen gel at a concentration of about 100 ng/ml gel;
  SDF1 is imbedded in the microchannels in a collagen gel at a concentration of about 100 ng/ml gel; and
  the scaffold is fabricated from the matrix material.

2. The scaffold of claim 1, having the shape of a human incisor, a human cuspid, a human bicuspid or a human molar.

3. The scaffold of claim 1, wherein the composition further comprises platelet-derived growth factor (PDGF), endothelial cell growth factor (ECGF), transforming growth factor-β1 (TGF-β1), epidermal growth factor (EGF), hepatocyte growth factor (HGF), a bone morphogenetic protein (BMP) other than BMP-7, a TGF-β, a growth and differentiation factor (GDF), insulin-like growth factor-1 (IGF1), vascular endothelial growth factor (VEGF), fibroblast growth factor (FGF), a dentin matrix protein, a dentin sialoprotein, a bone sialoprotein, amelogenin, or an integrin.

4. The scaffold of claim 1, fabricated from a composition that comprises an osteoconductive material.

5. The scaffold of claim 4, wherein the osteoconductive material is hydroxyapatite.

6. The scaffold of claim 5, comprising at least one feature selected from the group consisting of:
 (i) the composition is a mixture of ε-polycaprolactone and hydroxyapatite; or
 (ii) the composition is a mixture of about 80 wt % ε-polycaprolactone and about 20 wt % hydroxyapatite.

7. The scaffold of claim 1, wherein the composition comprises a slow-release formulation.

8. The scaffold of claim 1, comprising:
 a slow release formulation composition comprising a chemotactic growth factor of SDF1 and an osteogenic, dentinogenic, amelogenic, or cementogenic growth factor of BMP-7; and
 an osteoconductive material comprising a mixture of about 80 wt % ε-polycaprolactone and about 20 wt % hydroxyapatite;
 wherein the scaffold has the shape of a human incisor, a human cuspid, a human bicuspid or a human molar.

9. A method of making a scaffold of claim 1, the method comprising:
 fabricating the scaffold from the matrix material in the shape of a mammalian tooth;
 embedding the collagen gel, BMP-7 at a concentration of about 100 ng/ml, and SDF-1 at a concentration of about 100 ng/ml in the microchannels of the scaffold.

10. The method of claim 9, comprising at least one feature selected from the group consisting of:
 (i) the tooth is shaped like a tooth that is absent in a mammal, and the method further comprises making a model of an absent tooth using computer aided design (CAD), and synthesizing the scaffold with a bioplotter;
 (ii) the absent tooth is a first molar from a human mouth and a CT scan is made of a second molar analogous to the first molar but on the other side of the mouth, the CAD utilizing CT scan data of the second molar to design the scaffold;
 (iii) the scaffold is fabricated from a matrix material that comprises an osteoconductive material;
 (iv) the scaffold is fabricated from a matrix material that comprises an osteoconductive material and the osteoconductive material is hydroxyapatite; and
 (v) the scaffold is fabricated from a matrix material that comprises an osteoconductive material and the composition is a mixture of ε-polycaprolactone and hydroxyapatite.

11. The scaffold of claim 1, wherein the composition is encapsulated in a microsphere or liposome located in the scaffold.

12. A method of replacing a tooth in the mouth of a mammal, wherein the tooth is absent and a tooth socket is present in the mouth at the position of the absent tooth, the method comprising:

implanting an acellular mammalian tooth-shaped scaffold into the tooth socket;

wherein the scaffold has the shape of the missing tooth;

the scaffold comprises (i) a matrix material and (ii) a composition comprising stromal cell-derived factor-1 (SDF-1) and a bone morphogenetic protein-7 (BMP-7);

the scaffold is fabricated from the matrix material;

the composition is chemotactic, osteogenic, dentinogenic, amelogenic, or cementogenic;

the composition induces migration of progenitor cells when the scaffold is in contact with a dental tissue of a mammalian subject;

the composition is distributed throughout the tooth-shaped scaffold; and the scaffold does not comprise a living cell prior to implantation.

13. The method of claim 12, comprising at least one feature selected from the group consisting of:

(i) the method further comprising making a model of the absent tooth using computer aided design (CAD) and synthesizing the scaffold with a bioplotter;

(ii) the absent tooth is a first molar from a human mouth and a CT scan is made of a second molar analogous to the first molar but on the other side of the mouth, the CAD utilizing CT scan data of the second molar to design the scaffold;

(iii) the matrix material comprises an osteoconductive material;

(iv) the matrix material comprises an osteoconductive material, and the osteoconductive material is hydroxyapatite;

(v) the matrix material comprises an osteoconductive material and the composition is a mixture of $\epsilon$-polycaprolactone and hydroxyapatite;

(vi) the matrix material comprises an osteoconductive material and the composition is a mixture of about 80 wt % $\epsilon$-polycaprolactone and about 20 wt % hydroxyapatite;

(vii) the scaffold comprises microchannels having a diameter of between about 50 and about 500 μm;

(viii) the scaffold comprises microchannels having a diameter of about 200 μm;

(ix) the composition is imbedded in microchannels in a collagen gel;

(x) the composition is imbedded in microchannels in a collagen gel and the compound is SDF1 at a concentration of about 100 ng/ml gel, and the gel further comprises BMP-7 at a concentration of about 100 ng/ml gel; and (xi) the scaffold comprises a nonporous cap.

14. The method of claim 12, wherein BMP-7 is in the scaffold at about 10 ng/g to 1000 μg/g scaffold and SDF1 is in the scaffold at about 10 ng/g to 1000 μg/g scaffold.

15. The method of claim 12, wherein BMP-7 is in the scaffold at about 100 μg/g scaffold and SDF1 is in the scaffold at about 100 μg/g scaffold.

* * * * *